(12) United States Patent
Schneider et al.

(10) Patent No.: US 9,404,919 B2
(45) Date of Patent: *Aug. 2, 2016

(54) MULTIPLEXED ANALYSES OF TEST SAMPLES

(71) Applicant: SomaLogic, Inc., Boulder, CO (US)

(72) Inventors: Daniel J. Schneider, Arvada, CO (US); Dan Nieuwlandt, Longmont, CO (US); Bruce Eaton, Longmont, CO (US); Martin Stanton, Boulder, CO (US); Shashi Gupta, Louisville, CO (US); Stephan Kraemer, Boulder, CO (US); Dominic Zichi, Boulder, CO (US); Larry Gold, Boulder, CO (US)

(73) Assignee: SOMALOGIC, INC., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/176,933

(22) Filed: Feb. 10, 2014

(65) Prior Publication Data
US 2014/0249043 A1    Sep. 4, 2014

Related U.S. Application Data

(63) Continuation of application No. 12/958,620, filed on Dec. 2, 2010, now abandoned, which is a continuation-in-part of application No. 12/175,446, filed on Jul. 17, 2008, now Pat. No. 7,855,054, and a
(Continued)

(51) Int. Cl.
*G01N 33/53* (2006.01)
*G01N 33/543* (2006.01)
(Continued)

(52) U.S. Cl.
CPC ...... *G01N 33/5308* (2013.01); *G01N 33/54306* (2013.01); *G01N 33/6863* (2013.01); *G01N 33/74* (2013.01)

(58) Field of Classification Search
CPC .................... G01N 33/5308; G01N 33/54306; G01N 33/6863; G01N 33/74
See application file for complete search history.

(56) References Cited

U.S. PATENT DOCUMENTS

| | | |
|---|---|---|
| 4,587,044 A | 5/1986 | Miller |
| 4,737,453 A | 4/1988 | Primus et al. |

(Continued)

FOREIGN PATENT DOCUMENTS

| | | |
|---|---|---|
| EP | 0310251 | 4/1989 |
| GB | 2 183 661 | 6/1987 |

(Continued)

OTHER PUBLICATIONS

Hicke, B.J. et al., J. Clin. Invest., vol. 106, pp. 923-928 (2000).*

(Continued)

*Primary Examiner* — Teresa E Strzelecka
(74) *Attorney, Agent, or Firm* — Swanson & Bratschun, L.L.C.

(57) ABSTRACT

The present disclosure describes methods, devices, reagents, and kits for the detection of one or more target molecules that may be present in a test sample. The described methods, devices, kits, and reagents facilitate the detection and quantification of a non-nucleic acid target (e.g., a protein target) in a test sample by detecting and quantifying a nucleic acid (i.e., an aptamer). The methods described create a nucleic acid surrogate for a non-nucleic acid target, thus allowing the wide variety of nucleic acid technologies, including amplification, to be applied to a broader range of desired targets, especially protein targets. The disclosure further describes aptamer constructs that facilitate the use of aptamers in a variety of analytical detection applications.

20 Claims, 30 Drawing Sheets

Related U.S. Application Data continuation-in-part of application No. 11/623,580, filed on Jan. 16, 2007, now abandoned, and a continuation-in-part of application No. 11/623,535, filed on Jan. 16, 2007, now abandoned.

(60) Provisional application No. 61/051,594, filed on May 8, 2008, provisional application No. 61/031,420, filed on Feb. 26, 2008, provisional application No. 60/950,293, filed on Jul. 17, 2007, provisional application No. 60/950,281, filed on Jul. 17, 2007, provisional application No. 60/950,283, filed on Jul. 17, 2007.

(51) Int. Cl.
*G01N 33/68* (2006.01)
*G01N 33/74* (2006.01)

(56) References Cited

U.S. PATENT DOCUMENTS

| | | | |
|---|---|---|---|
| 4,752,566 A | 6/1988 | Collins et al. |
| 5,124,246 A | 6/1992 | Urdea et al. |
| 5,270,163 A | 12/1993 | Gold et al. |
| 5,412,087 A | 5/1995 | McGall et al. |
| 5,432,099 A | 7/1995 | Ekins et al. |
| 5,445,934 A | 8/1995 | Fodor et al. |
| 5,475,096 A | 12/1995 | Gold et al. |
| 5,476,766 A | 12/1995 | Gold et al. |
| 5,510,270 A | 4/1996 | Fodor et al. |
| 5,527,894 A | 6/1996 | Gold et al. |
| 5,556,752 A | 9/1996 | Lockhart et al. |
| 5,567,588 A | 10/1996 | Gold et al. |
| 5,580,737 A | 12/1996 | Polisky |
| 5,582,981 A | 12/1996 | Toole et al. |
| 5,595,877 A | 1/1997 | Gold et al. |
| 5,639,868 A | 6/1997 | Janjic et al. |
| 5,645,985 A | 7/1997 | Froehler |
| 5,654,151 A | 8/1997 | Allen et al. |
| 5,658,738 A | 8/1997 | Nadeau et al. |
| 5,681,697 A | 10/1997 | Urdea et al. |
| 5,744,305 A | 4/1998 | Fodor et al. |
| 5,756,291 A | 5/1998 | Griffin et al. |
| 5,801,154 A | 9/1998 | Baracchini et al. |
| 5,817,785 A | 10/1998 | Gold et al. |
| 5,840,867 A | 11/1998 | Toole et al. |
| 5,843,653 A | 12/1998 | Gold et al. |
| 5,861,254 A | 1/1999 | Schneider et al. |
| 5,874,218 A | 2/1999 | Drolet et al. |
| 5,955,268 A | 9/1999 | Granados et al. |
| 5,958,691 A | 9/1999 | Pieken |
| 6,030,776 A | 2/2000 | Eaton et al. |
| 6,114,120 A | 9/2000 | Jensen et al. |
| 6,184,364 B1 | 2/2001 | Pieken et al. |
| 6,207,446 B1 | 3/2001 | Szostak et al. |
| 6,232,462 B1 | 5/2001 | Collins et al. |
| 6,242,246 B1 | 6/2001 | Gold et al. |
| 6,344,318 B1 | 2/2002 | Gold et al. |
| 6,346,611 B1 | 2/2002 | Pagratis et al. |
| 6,458,539 B1 | 10/2002 | Gold et al. |
| 6,458,543 B1 | 10/2002 | Gold et al. |
| 6,503,715 B1 | 1/2003 | Gold et al. |
| 6,544,776 B1 | 4/2003 | Gold et al. |
| 6,716,583 B2 | 4/2004 | Gold et al. |
| 7,074,586 B1 | 7/2006 | Cheronis et al. |
| 7,368,236 B2 | 5/2008 | Gold et al. |
| 7,855,054 B2 | 12/2010 | Schneider et al. |
| 7,947,447 B2 | 5/2011 | Zichi et al. |
| 7,964,356 B2 | 6/2011 | Zichi et al. |
| 2002/0037506 A1 | 3/2002 | Lin et al. |
| 2002/0119473 A1 | 8/2002 | Lupold et al. |
| 2003/0219801 A1 | 11/2003 | Lipshutz |
| 2003/0228603 A1 | 12/2003 | Cload et al. |
| 2004/0018508 A1 | 1/2004 | Friedman |
| 2004/0142384 A1 | 7/2004 | Cohen et al. |
| 2004/0209261 A1 | 10/2004 | Keys et al. |
| 2004/0219526 A1 | 11/2004 | Reddy et al. |
| 2004/0235053 A1 | 11/2004 | Lam et al. |
| 2005/0130195 A1 | 6/2005 | Fujihara et al. |
| 2005/0142582 A1 | 6/2005 | Doyle et al. |
| 2005/0158780 A1 | 7/2005 | Lupold et al. |
| 2005/0227225 A1 | 10/2005 | Krevolin |
| 2005/0250147 A1 | 11/2005 | Macevicz |
| 2005/0288244 A1 | 12/2005 | Manoharan et al. |
| 2006/0057573 A1 | 3/2006 | Gold et al. |
| 2006/0105341 A1 | 5/2006 | Krause et al. |
| 2006/0105378 A1 | 5/2006 | Hicke et al. |
| 2007/0003950 A1 | 1/2007 | Shen et al. |
| 2007/0161015 A1 | 7/2007 | Zheng et al. |
| 2007/0161020 A1 | 7/2007 | Luo et al. |
| 2007/0166741 A1 | 7/2007 | Heil et al. |
| 2007/0166742 A1 | 7/2007 | Gold et al. |
| 2008/0160535 A1 | 7/2008 | Gold et al. |
| 2009/0004667 A1 | 1/2009 | Zichi et al. |
| 2009/0306461 A1 | 12/2009 | Oksenberg et al. |
| 2010/0055695 A1 | 3/2010 | Zichi et al. |
| 2010/0317120 A1 | 12/2010 | Heil et al. |
| 2011/0082286 A1 | 4/2011 | Zichi |
| 2011/0245479 A1 | 10/2011 | Zichi et al. |
| 2011/0275794 A1 | 11/2011 | Rohloff et al. |
| 2012/0115752 A1 | 5/2012 | Zichi et al. |
| 2012/0264117 A1 | 10/2012 | Sanders et al. |
| 2014/0058076 A1 | 2/2014 | Rohloff et al. |

FOREIGN PATENT DOCUMENTS

| | | |
|---|---|---|
| WO | WO 92/14842 | 3/1992 |
| WO | WO 92/14843 | 9/1992 |
| WO | WO 95/18377 | 7/1995 |
| WO | WO 95/21265 | 8/1995 |
| WO | WO 96/34874 | 11/1996 |
| WO | WO 96/41019 | 12/1996 |
| WO | WO 98/33941 | 8/1998 |
| WO | WO 99/31275 | 6/1999 |
| WO | WO 01/09156 | 2/2001 |
| WO | WO 01/09159 | 2/2001 |
| WO | WO 01/61037 | 8/2001 |
| WO | WO 02/44726 | 6/2002 |
| WO | WO 02/083953 | 10/2002 |
| WO | WO 03/070984 | 8/2003 |
| WO | WO 2004/043996 | 5/2004 |
| WO | WO 2005/108609 | 11/2005 |
| WO | WO 2006/096754 | 9/2006 |
| WO | WO 2013/185078 | 12/2013 |

OTHER PUBLICATIONS

Murphy, M.B. et al., Nucl. Acids Res., vol. 31, e110, pp. 1-8 (2003).*
Baldrich et al. (2004) Analytical Chemistry 76(23):7053-7063, "Aptasensor Development: Elucidation of Critical Parameters for Optimal Aptamer Performance".
Bock et al. (Mar. 2004) Proteomics 4(3):609-618, "Photoaptmaer arrays applied to multiplexed proteomic analysis".
Bock et al., (1992) Nature 355:564-565 "Selection of Single-Stranded DNA Molecules That Bind and Inhibit Human Thrombin".
Brodsky (2002) Mol. Cell. Proteomics 1(12):922-929, "A Microbead-based System for Identifying and Characterizing RNA-Protein Interactions by Flow Cytometry".
Bullock et al. (2001) Nature 414:611-616, "Conserved signals and machinery for RNA transport in Drosophila oogenesis and embryogenesis".
Cho et al. (2004) Electrophoresis 25:3730-3739, "Microbead-based affinity chromatography chip using RNA aptamer modified with photocleavable linker".
Daniels et al. (Dec. 23, 2003) PNAS 100(26):15416-15421, "A tenascin-C aptamer identified by tumor cell SELEX: Systematic evolution of ligands by exponential enrichment".
Davis et al. (Sep. 3, 2002) PNAS, 99(18):11616-11621, "Isolation of high-affinity GTP aptamers from partially structured RNA libraries".
Dewey et al. (1995) J. Am. Chem. Soc. 117: 8474-8475, "New Uridine Derivatives for Systematic Evolution of RNA Ligands by Exponential Enrichment".

(56) References Cited

OTHER PUBLICATIONS

DiDonato (2006) "Disseration. Part II. Synthesis and Evaluation of Modified Nucleotides for DNA Aptamer Selection" University of North Carolina, Raleigh 30-53.
Drabovich et al. (May 1, 2006) Analytical Chemistry 78(9):3171-3178, "Selection of smart aptamers by methods of kinetic capillary electrophoresis".
Drolet et al. (Aug. 1996) Nature Biotechnology 14(8):1021-1025, "An enzyme-linked oligonucleotide assay".
Ekins and Chu (Sep. 1997) JIFCC 9(3):100-109, "Immunoassay and Other Ligand Assays: Present Status and Future Trends".
Ellington & Szostak (1990) "Selection of RNAs with ligand-specific binding activity from pools of random sequence molecules" RNA Processing meeting abstract, p. 84.
EP Extended Search Report issued Dec. 9, 2010 in EP application serial No. 10176907.3.
EP Search report issued Dec. 1, 2009 in EP application serial No. 08782010.6.
European Office Action issued Feb. 16, 2011 in European Application Serial No. 08782010.6.
EP Office Action issued Feb. 28, 2011 in European application serial No. 07718147.7.
European Search Report issued Oct. 25, 2012 in EP 08782013.0.
Extended European Search Report issued Sep. 13, 2013 in EP 13164719.0.
Famulok and Szostak (1992) Angew. Chem. Int. Ed. Engl. 31(8): 979-988, "In Vitro Selection of Specific Ligand-binding Nucleic Acids".
Ferguson et al., (Dec. 1996) Nature Biotechnology, 14:1681-1684, "A fiber-optic DNA biosensor microarray for the analysis of gene expression".
Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Gold et al. (Jan. 1, 1995) Harvey Lectures 91:47-57, "The SELEX Process: A Surprising Source of Therapeutic and Diagnostic Compounds".
Gold et al. (Jan. 1995) Annual Review of Biochemistry 64:763-797, "Diversity of Oligonucleotide Functions".
Gold et al. (Dec. 7, 2010) Plos One 5(12):e15004, "Aptamer-Based Multiplexed Proteomic Technology for Biomarker Discovery".
IPRP issued Jan. 19, 2010 in PCT/US2008/070386.
ISR and Written Opinion mailed Oct. 16, 2008 in PCT/US2008/070386.
Ito et al. (2003) Nucleic Acids Research 31(10):2514-2523, "Synthesis, thermal stability and resistance to enzymatic hydrolysis of the oligonucleotides containing 5-(N-aminohexyl)carbamoyl-2'-O-methylurindines".
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kang et al. (May 29, 2007) FEBS Letters, 581(13):2497-2502, "Combinatorial selection of a RNA thioaptamer that binds to Venezuelan equine encephalitis virus capsid protein".
Kawakami et al. (1997) Nucleic Acids Symposium Series No. 37:201-202, "Evolution of a phosphorothioate RNA library during in vitro selection".
Kinzler and Vogelstein (1989) Nucleic Acids Research 17(10): 3645-3653, "Whole genome PCR: application to the identification of sequences bound by gene regulatory proteins".
Kirby et al. (2004) Anal. Chem. 76(14):4066-4075, "Aptamer-Based Sensor Arrays for the Detection and Quantitation of Proteins".
Kramer et al. (1974) J. Mol. Biol. 89: 719-736, "Evolution in vitro: sequence and phenotype of a mutant RNA resistant to ethidium bromide".
Knill et al. (Oct. 1997) J. Chromatology. B, 699:173-208, "Labeling reactions applicable to chromatography and electrophoresis of minute amounts of proteins".
Langer et al. (Nov. 1981) Proc. Natl. Acad. Sci. USA,78(11):6633-6637, "Enzymatic synthesis of biotin-labeled polynucleotides: Novel nucleic acid affinity probes".
Latham et al. (1994)Nucleic Acids Research 22(14):2817-2822, "The application of a modified nucleotide in aptamer selection: novel thrombin aptamers containing 5-(1-pentynyl)-2' -deoxyuridine".
Lavitrano et al. (1992) Molecular Reproduction and Development 31:161-169, "The Interaction between Exogenous DNA and Sperm Cells".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
Lipshutz et al. (1995) BioTechniques 19:442-447, "Using Oligonucleotide Probe Arrays to Access Genetic Diversity".
Liu et al. (May 2012) Plos One 7(5):1-10, "Selection of aptamers specific for adipose tissue".
McGregor et al. (1996) Nucl. Acids. Res. 24:3173-3180, "Preparation of oligoribonucleotides containing 4-thiouridine using Fpmp chemistry. Photo-crosslinking to RNA binding proteins using 350 nm irradiation".
Molecular Probes Handbook, 8th Edition, Section 8.2 (2001) "Labeling Oligonucleotides and Nucleic Acids".
Niemeyer et al. (Jan. 1, 1994) Nucleic Acid Research 22(25):4430-5539, "Oligonucleotide-Directed Self-Assembly of Proteins: Semisynthetic DNA-Streptavidin Hybrid Molecules as Connectors for the Generation of Macroscopic Arranys and the Construction of Supramolecular Bioconjugates".
Nomura et al. (1997) Nucleic Acids Research 25(14):2784-2791, "Site-specific introduction of functional groups into phosphodiester oligodeoxynucleotides and their thermal stability and nuclease-resistance properties".
Office Action issued Apr. 27, 2009 in U.S. Appl. No. 11/623,580.
Office Action issued Feb. 22, 2010 in U.S. Appl. No. 11/623,580.
Office Action issued Jan. 10, 2011 in U.S. Appl. No. 12/771,895.
Office Action issued Jun. 24, 2010 in U.S. Appl. No. 12/499,967.
Office Action issued Jun. 25, 2010 in U.S. Appl. No. 12/175,434.
Office Action issued Jun. 9, 2010 in U.S. Appl. No. 12/175,446.
Office Action issued Feb. 23, 2011 in U.S. Appl. No. 12/859,930.
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of *E. coli* promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Osborne et al. (1997) Current Opinion in Chemical Biology 1:5-9, "Aptamers as Therapeutic and Diagnostic Reagents: Problems and Prospects".
Partial European Search Report issued Jul. 11, 2013 in EP 13164719.0.
Pinkel et al. (Dec. 1988) Proc. Natl. Acad. Sci. USA 85:9138-9142, "Fluorescence in situ hybridization with human chromosome-specific libraries: Detection of trisomy 21 and translocations of chromosome 4".
Potyrailo et al. (Aug. 1998) Anal. Chem. 70(16):3419-3425, "Adapting Selected Nucleic Acid Ligands (Aptamers) to Biosensors".
Puig et al. (Jul. 2001) Methods: A Companion to Methods in Ezymology 24(3):218-229, "The tandem affinity purificaiton (TAP) method: A general procedure of protein complex purification".
Robertson and Joyce (Mar. 1990) Nature 344: 467-468, "Selection in vitro of an RNA enzyme that specifically cleaves single-stranded DNA".

(56) References Cited

OTHER PUBLICATIONS

Saitoh et al. (2002) Nucleic Acids Research Supplement 2:215-216 "Modified DNA aptamers against sweet agent aspartame".

Sakthivel et al. (1998) Angew Chem Int Ed 37(20):2872-2875 "Expanding the Potential of DNA for Binding and Catalysis: Highly Functionalized dUTP Derivatives That are Substrates for Thermostable DNA Polymerases".

Schoetzau et al. (2003) Bioconjugate Chemistry 14:919-926, "Aminomodified Nucleobases: Functionalized Nucleoside Triphosphates Applicable for SELEX".

Shaohua et al. (2009) Journal of Pathology 218:327-336, "Identification of an aptamer targeting nhRNP A1 by tissue slide-based SELEX".

Srisawat et al. (2001) Nucleic Acids Research 29(2):1-5 "Sephadex-binding RNA ligands: rapid affinity purification of RNA from complex RNA mixtures".

Syvanen et al. (1986) Nucleic Acid Research, 14(12):5037-5048, "Fast quantification of nucleic acid hybrids by affinity-based hybrid collection".

Szostak (1988) Redesigning the Molecules of Life, (S.A. Benner ed.) Springer-Verlag Berlin Heidelberg, pp. 87-113.

Terpetschnig et al. (1994) Anal. Biochem. 217:197-204, "Synthesis of Squaraine-N-Hydroxysuccinimide Esters and Their Biological Application as Long-Wavelength Flurorescent Labels".

Thiesen and Bach (Jun. 1990) Nucleic Acids Res. 18(11): 3203-3209, "Target detection assay (TDA): a versatile procedure to determine DNA binding sites as demonstrated on SP1 protein".

Tuerk and Gold (Aug. 1990) Science 249: 505-510, "Systematic evolution of ligands by exponential enrichment: RNA ligands to bacteriophage T4 DNA polymerase".

Uddin et al. (1997) Nucleic Acids Research, 25(20):4139-4146, "A fiber optic biosensor for fluorimetric detection of triple-helical DNA".

Ueno et al. (1997) Nucleic Acids Research 25(19):3777-3782, "Effects of 5-(N-aminohexyl)carbamoyl-2'-deoxyuridine on endonuclease stability and the ability of oligodeoxynucleotide to activate RNase H".

Vaught, Jonathan David, Thesis Oct. 2008, "Enhancing the Functionality of Nucleic Acids".

\* cited by examiner

One Catch Constructs
Affinity           Photocrosslink
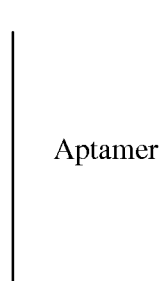
Aptamer
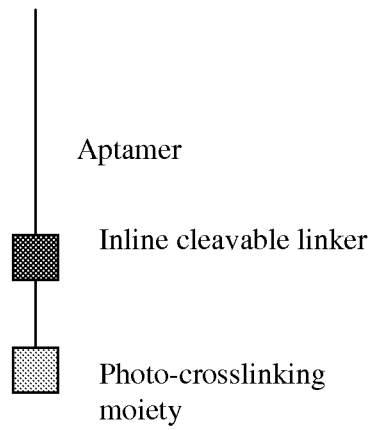
Aptamer
Inline cleavable linker
Photo-crosslinking moiety
FIG. 3A          FIG. 3B
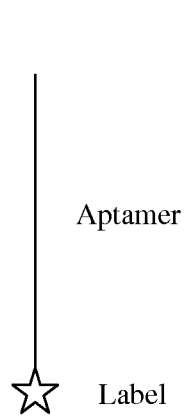
Aptamer
Label
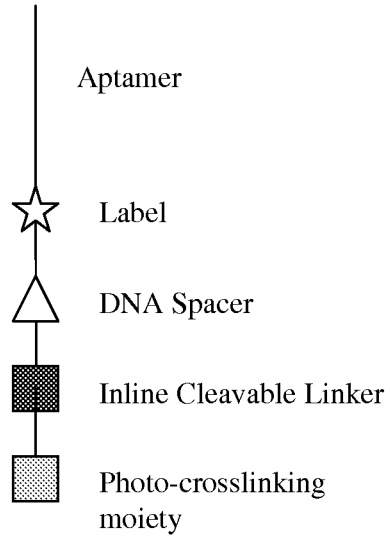
Aptamer
Label
DNA Spacer
Inline Cleavable Linker
Photo-crosslinking moiety
FIG. 3C          FIG. 3D

Two Catch Constructs

Affinity

Photocrosslink

Two Catch Constructs

Affinity

Photocrosslink

Figure 4

| | | | |
|---|---|---|---|
| 4-1BB | C4 | Cytochrome P450 3A4 | GAS1 |
| 4-1BB ligand | C4b | DAN | GASP-2 |
| 6Ckine | C5 | DARPP-32 | G-CSF-R |
| a1-Antichymotrypsin | C5a | DC-SIGN | GDF-9 |
| a2-Antiplasmin | C5b, 6 Complex | DC-SIGNR | GDF-11 |
| ACE2 | C6 | D-dimer | GDNF |
| Activated Protein C | C7 | DEAD-box protein 19B | GFAP |
| Activin A | C8 | Desmoglein-1 | GFRa-1 |
| Activin RIA | C9 | DKK1 | GFRa-2 |
| Activin RIB | Cadherin E | DLL4 | GFRa-3 |
| ADAMTS-4 | Cadherin-5 | Dopa decarboxylase | GIB |
| ADAMTS-5 | Calcineurin B a | DRG-1 | GIIE |
| Aggrecan | Calpain I | DRR1 | GITR |
| AIF1 | Calpastatin | Dtk | Glucocorticoid receptor |
| ALCAM | Carbonic Anhydrase IV | EDA (A2) | Glutamate carboxypeptidase |
| ALK-1 | Cardiotrophin-1 | EDAR | Glutathione S-transferase Pi |
| Alkaline phosphatase, bone | Caspase-3 (pro) | EG-VEGF | Glypican 3 |
| AMPM2 | Catalase | eIF-5 | gp130, soluble |
| Amyloid precursor protein | Cathepsin A | Elastase | GPC2 |
| Angiogenin | Cathepsin B | EMAP-2 | GPVI |
| Angiopoietin-1 | Cathepsin D | ENA-78 | Granulysin |
| Angiopoietin-2 | Cathepsin G | Endostatin | Granzyme B |
| Angiopoietin-4 | Cathepsin S | Eotaxin | Gro-a |
| ANGL3 | Cathepsin V | Eotaxin-2 | Gro-g |
| ANGL4 | CCL28 | Eotaxin-3 | Growth hormone receptor |
| Apo A-I | CD5L | Ephrin-A4 | GSK-3 beta |
| Apo B | CD22 | Ephrin-A5 | GV |
| Apo E | CD23 | Ephrin-B3 | GX |
| Apo E2 | CD30 | Epithelial cell kinase | HAI-1 |
| Apo E3 | CD30 Ligand | EPO-R | Haptoglobin, Mixed type |
| Apo E4 | CD36 ANTIGEN | ER | Hat1 |
| APRIL | CD39 | ERBB1 | HB-EGF |
| AREG | CD97 | ERBB2 | HCC-1 |
| ARGI1 | CD109 | ERBB3 | HCC-4 |
| ARSB | Ceruloplasmin | ERBB4 | HDAC8 |
| ART | CFC1 | ERK-1 | Hemopexin |
| Artemin | Chk1 | ESAM | Heparin cofactor II |
| ASAH2 | Ck-b-8-1 | Factor B | HGF |
| ASAHL | CK-BB | Factor D | Histone H1.2 |
| ATS1 | CK-MM | Factor H | HIV-2 Rev |
| ATS13 | CLF-1/CLC Complex | Factor I | HMG-1 |
| Aurora kinase A | CMP-Sialic Acid Synthetase | Fas ligand, soluble | HO-2 |
| Azurocidin | CNTF | Fas, soluble | HPLN1 |
| B7 | CNTFR alpha | FCG2A | HPV E7 Type 16 |
| B7-2 | CNTN2 | FCG2B | HPV E7 Type18 |
| BAFF | Coagulation Factor a-XIIa | FCG3B | HSP 60 |
| BCAM | Coagulation Factor IX | FCGR1 | HSP 70 |
| b-Catenin | Coagulation Factor IXab | Ferritin | HSP 90a |
| Bcl-2 | Coagulation Factor V | FGF-4 | HSP 90b |
| BCMA | Coagulation Factor VII | FGF-5 | HTRA2 |
| BDNF | Coagulation Factor X | FGF-6 | HVEM |
| b-Endorphin | Coagulation Factor Xa | FGF7 | I11RA |
| bFGF | Coagulation Factor XI | FGF-8B | I12R2 |
| bFGF-R | Coagulation Factor XIa | FGF9 | I-309 |
| BGH3 | Coagulation factor XIII | FGF-10 | iC3b |
| b-Glucosidase | Collagen Type I | FGF-16 | ICOS |
| BGN | COLEC12 | FGF-17 | IDE |
| BLC | COMMD7 | FGF-18 | IDS |
| BMP-7 | Contactin-1 | FGF-19 | IDUA |
| BMP-14 | Contactin-4 | FGF-20 | IFN-g |
| BMPER | COX-2 | FGFR-2 | IFN-g R1 |
| BMPR1A | Cripto | Fibrinogen | IFN-lambda 1 |
| BMP RII | CRIS3 | Fibronectin | IFN-lambda 2 |
| b-NGF | CRP | Flt-3 | IgE |
| Bone proteoglycan II | CTACK | Flt-3 ligand | IGFBP-1 |
| BPI | CTGF | Fractalkine/CX3CL-1 | IGFBP-2 |
| C1q | CTLA-4 | FSH | IGFBP-3 |
| C1r | CXCL16, soluble | FST | IGFBP-4 |
| C2 | Cystatin C | FYN | IGFBP-5 |
| C3 | Cystatin M | GA733-1 protein | IGFBP-6 |
| C3a | CYTD | Galectin-2 | IGFBP-7 |
| C3adesArg | CYTF | Galectin-3 | IGF-I |
| C3b | CYTN | Galectin-4 | IGF-I sR |
| C3d | Cytochrome c | Galectin-7 | IGF-II receptor |

Figure 4 cont'd

| | | | |
|---|---|---|---|
| IgM | Lysozyme | P-Cadherin | SPINT2 |
| IL-1b | LYVE1 | PCNA | Spondin-1 |
| IL-1 R AcP | Macrophage mannose receptor | PDGF Rb | sRAGE |
| IL-1 R4 | MAPK14 | PDGF-AA | sRANKL |
| IL-1 sRI | MATN2 | PDGF-BB | sTie-1 |
| IL-1F7 | MATN3 | PD-L2 | sTie-2 |
| IL-1Rrp2 | MBL | PDPK1 | sTREM-1 |
| IL-2 | MCP-1 | PECAM-1 | STX1a |
| IL-2 sRg | MCP-2 | Persephin | Sulfotransferase, Nod Factor |
| IL-4 | MCP-3 | PF-4 | suPAR |
| IL-4 sR | MCP-4 | PGRP-S | TACI |
| IL-6 | M-CSF R | PIGR | TARC |
| IL-6 sRa | MDC | PKB | tau |
| IL-7 | MEK1 | PKC-A | TBP |
| IL-7 R alpha | MEPE | PKC-B-II | TECK |
| IL-8 | MER | PKC-D | Tenascin |
| IL-10 | Met | PKC-Z | Testican-2 |
| IL-10 Rb | METAP1 | Plasmin | TF |
| IL-11 | MIA | Plasminogen | TFPI |
| IL-12 | MICA | PIGF | TGF-b1 |
| IL-12 Rb1 | Midkine | Prekallikrein | TGF-b2 |
| IL-13 | Mif4gd, Mouse | PRL | TGF-b RIII |
| IL-13 Ra1 | MIG | Properdin | Thrombin |
| IL-15 Ra | Miox, Rat | Prostatic acid phosphatase | Thyroxine-Binding Globulin |
| IL-16 | MIP-1a | Protease nexin I | TIG2 |
| IL-17 sR | MIP-1b | Protein C | TIMP-1 |
| IL-17B | MIP-3a | Protein S | TIMP-2 |
| IL-17D | MIP-3b | Prothrombin | TIMP-3 |
| IL-17E | MK01 | PSA | TNF sR-I |
| IL-17F | MMP-1 | PSA-ACT | TNF sR-II |
| IL-18 Bpa | MMP-2 | P-Selectin | TNFSF15 |
| IL-18 Ra | MMP-3 | PSMA | TNFSF18 |
| IL-18 Rb | MMP-7 | PTHrP | Tom34 |
| IL-19 | MMP-8 | PTN | Topoisomerase I |
| IL-20 | MMP-9 | PTP-1B | tPA |
| IL-21 sR | MMP-13 | Rab GDP dissociation inhibitor beta | Tpo |
| IL-22 | MMP-14 | Rac1 | TRAIL |
| IL-27 | MMP-17 | RAD51 | TRAIL R2 |
| Inosine triphosphatase | MOZ | RANTES | TRAIL R4 |
| IP-10 | MP112 | RAP | Transferrin |
| IR | MPIF-1 | RELT | TrATPase |
| I-TAC | MSP R | Resistin | TrkB |
| JAM-B | Myeloperoxidase | RET | TrkC |
| JAM-C | Myosin regulatory light chain 2 | RGMB | Troponin I |
| Kallikrein 4 | NADPH-P450 Oxidoreductase | RGM-C | Troponin T |
| Kallikrein 5 | NANOG | S100A4 | Trypsin |
| Kallikrein 8 | NAP-2 | SAP | Trypsin 2 |
| Kallikrein 11 | NCAM-L1 | SARP-2 | TSLP |
| Kallikrein 12 | NET4 | sCD14 | TSLP R |
| Kallikrein 13 | NEUREGULIN-1 | SCF sR | TSP2 |
| Karyopherin-a2 | Neurotrophin-3 | SCGF-alpha | TSP4 |
| Kininogen, HMW, Single Chain | Neurotrophin-5 | SCGF-beta | TWEAK |
| Kininogen, HMW, Two Chain | NG36 | SDF-1a | UBC9 |
| KLH | Nidogen | SDF-1b | Ubiquitin+1 |
| KREM2 | NKG2D | Semaphorin 3A | ULBP-1 |
| Ku70 | NKp30 | sE-Selectin | ULBP-2 |
| Lactoferrin | NKp44 | SET9 | ULBP-3 |
| LAG-1 | Noggin | sFRP-3 | uPA |
| Laminin | Nogo Receptor | sICAM-2 | URB |
| Layilin | NovH | sICAM-3 | VCAM-1 |
| LBP | NPS-PLA2 | SIGIRR | VEGF |
| LD78-beta | NRP1 | Siglec-6 | VEGF sR2 |
| Leptin | OLR1 | Siglec-7 | VEGF sR3 |
| Lipocalin 2 | ON | Siglec-9 | VEGF-C |
| LKHA4 | OPG | SLAMF8 | VEGF-D |
| LRIG3 | OSM | sLeptin R | Vitronectin |
| LRP8 | OX40 Ligand | SLPI | vWF |
| LSAMP | PAFAH beta subunit | sL-Selectin | WFKN2 |
| Luteinizing hormone | PAI-1 | SMAC | WIF-1 |
| LY86 | PAPP-A | sn-1,2-Diacylglycerol Kinase | WISP-3 |
| LY9 | PARC | SOD | XEDAR |
| Lymphotactin | Partner protein A | Soggy-1 | Yes |
| Lymphotoxin b R | Partner protein B | Sonic Hedgehog | |

Figure 6

A         5' - CY3 – APTAMER – 3'

B         5' – B- PC- SPACER- CY3- APTAMER

C         5' - ANA – PC – SPACER - CY3 – APTAMER

D         5' - ANA – PC – SPACER - CY3 – APTAMER – HYB/HYB'-(T)$_8$-(AB)$_2$

1 Plasma Sample

Split into 68 Samples

Run the assay on each samples

Combine 34 of the samples

Split again

Detect using Hybridization

Base = Uridine (U) or Cytidine(C) (attachment is to the 5-position)
K = R' group plus $(CH_2)_n$ connecting group, where n = 0-3

Figure 16 continued wherein

R"" is selected from the group consisting of a branched or linear lower alkyl (C1-C20); halogen (F, Cl, Br, I); nitrile (CN); boronic acid ($BO_2H_2$); carboxylic acid (COOH); carboxylic acid ester (COOR"); primary amide ($CONH_2$); secondary amide (CONHR"); tertiary amide (CONR"R'"); sulfonamide ($SO_2NH_2$); N-alkylsulfonamide (SONHR").

wherein

R", R'" are independently selected from a group consisting of a branched or linear lower alkyl (C1-C2)); phenyl ($C_6H_5$); an R"" substituted phenyl ring (R""$C_6H_4$); wherein R"" is defined above; a carboxylic acid (COOH); a carboxylic acid ester (COOR""); wherein R"" is a branched or linear lower alkyl (C1-C20); and cycloalkyl; wherein R" = R'" = $(CH_2)_n$; wherein n =2-10.

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
gagtgtgtga cgagtgtgga g                                               21

<210> SEQ ID NO 2
<211> LENGTH: 19
<212> TYPE: DNA
<213> ORGANISM: Artificial
<220> FEATURE:
<223> OTHER INFORMATION: Synthetic

<400> SEQUENCE: 2
tcggttgtgg tgacgcccg                                                  19
```

MULTIPLEXED ANALYSES OF TEST SAMPLES

RELATED APPLICATIONS

This application is a continuation of U.S. application Ser. No. 12/958,620, filed Dec. 2, 2010, entitled "Multiplexed Analyses of Test Samples", which is a continuation-in-part application of U.S. application Ser. No. 12/175,446, filed Jul. 17, 2008, entitled "Multiplexed Analyses of Test Samples". U.S. application Ser. No. 12/175,446 claims the benefit of U.S. Provisional Application Ser. No. 60/950,281, filed Jul. 17, 2007, U.S. Provisional Application Ser. No. 60/950,293, filed Jul. 17, 2007, U.S. Provisional Application Ser. No. 60/950,283, filed Jul. 17, 2007, U.S. Provisional Application Ser. No. 61/031,420, filed Feb. 26, 2008 and U.S. Provisional Application Ser. No. 61/051,594, filed May 8, 2008. U.S. application Ser. No. 12/175,446 is also a continuation in part of U.S. application Ser. No. 11/623,580 and U.S. application Ser. No. 11/623,535, each of which was filed on Jan. 16, 2007. Each of these applications is incorporated herein by reference in its entirety.

FIELD OF THE INVENTION

The present invention relates generally to methods, devices, reagents, and kits for the detection of a target molecule in a sample and, more specifically, to the detection and/or quantification of one or more target molecules that may be contained in a test sample. Such methods have a wide utility in diagnostic applications as well as in biomarker discovery and the design and development of therapeutics.

Incorporated by reference herein in its entirety is the Sequence Listing entitled "Sequence_Listing_ST25.txt", created Nov. 30, 2010, size of one kilobyte.

BACKGROUND

The following description provides a summary of information relevant to the present disclosure and is not a concession that any of the information provided or publications referenced herein is prior art to the presently claimed invention.

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands" see also, e.g., U.S. Pat. No. 6,242,246, U.S. Pat. No. 6,458,543, and U.S. Pat. No. 6,503,715, each of which is entitled "Nucleic Acid Ligand Diagnostic Biochip". Once the microarray is contacted with a sample, the aptamers bind to their respective target molecules present in the sample and thereby enable a determination of the absence, presence, amount, and/or concentration of the target molecules in the sample.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip". These photoreactive aptamers are also referred to as photoaptamers. See, e.g., U.S. Pat. No. 5,763,177, U.S. Pat. No. 6,001,577, and U.S. Pat. No. 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables a determination of the absence, presence, amount, and/or concentration of the target molecules in the test sample.

In both of these assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Accordingly, a need exists for methods, devices, reagents, and kits that provide high sensitivity assays for the detection and/or quantification of target molecules in a test sample by optimizing conditions that affect one or more of the following: (1) the activity of aptamers, (2) the efficiency of achieving binding equilibria for aptamer-target molecule complexes, (3) the formation of covalent bond(s) between an aptamer and its target molecule, (4) removal of extraneous sample components and excess aptamers, (5) dissociation of the affinity complex formed through the use of slow off-rate aptamers, and (6) the detection of aptamer-target molecule complexes.

SUMMARY

The present disclosure includes methods, devices, reagents, and kits for the detection and/or quantification of one or more target molecules that may be present in a test sample. More specifically, the disclosure provides methods for the purification of aptamer affinity complexes (or aptamer covalent complexes), by removing both free target and free aptamers from the aptamer affinity complexes (or aptamer covalent complexes), thereby removing potential sources of noise in the assay. The present disclosure also provides aptamer- and photoaptamer-based assays for the quantification of target molecule wherein the aptamer (or photoaptamer) can be separated from the aptamer affinity complex (or photoaptamer covalent complex) for final detection using any suitable nucleic acid detection method. The disclosure also describes aptamer constructs that facilitate the separation of the assay components from the aptamer affinity complex (or photoaptamer covalent complex) and permit isolation of the aptamer for detection and/or quantification. The disclosure also describes methods, devices, kits, and reagents that offer improved sensitivity and specificity by employing aptamers that have slow off-rates from their targets and improved binding efficiencies. The present disclosure also provides methods, devices, kits, and reagents for the multiplexed analysis of a test sample, wherein multiple targets in the test sample may be simultaneously detected and/or quantified. Ultimately these methods and reagents allow for the conversion of a target concentration (for example a protein target concentration in a test sample) to a nucleic acid concentration that can be detected and quantified by any of a wide variety of nucleic acid detection and quantification methods. Further, once the target concentration has been effectively converted to a corresponding nucleic acid concentration, standard nucleic acid amplification and detection steps can then be employed to increase the signal. Methods according to the present disclosure may be conducted in vitro.

Single Catch Affinity Assay. In one embodiment, a test sample is contacted with an aptamer that has a specific affinity for a target molecule. If the test sample contains the target molecule, an aptamer affinity complex will form in the mixture with the test sample. In one embodiment, a tag is attached to the target molecule of the aptamer affinity complex. (Note that the tag is designed such that it can be attached to the target in a manner that does not disrupt the aptamer affinity complex.) In another embodiment, the tag is attached to the target prior to the formation of the aptamer affinity complex. In another embodiment, the tag is added to the target at any point prior to exposing the mixture to the capture element on the solid support. The tagged aptamer affinity complex is next captured on a solid support by exposing the mixture to the solid support. The attachment is accomplished by contacting the solid support with the aptamer affinity complex and allowing the tag to associate either, directly or indirectly, with an appropriate capture agent that is attached to the solid support. The aptamer affinity complex that has associated with the capture agent on the solid support is partitioned from the remainder of the test sample mixture, thereby removing any free aptamer. The aptamers that are complexed with the target in the aptamer affinity complex can be released from the solid support by dissociation of the aptamer affinity complex. Finally, the released aptamers can be detected and/or quantified using any of a variety of suitable nucleic acid detection methods, including but not limited to mass spectrometry, the Invader assay method, a nucleic acid chip, quantitative polymerase chain reaction (Q-PCR), and the like. In some embodiments, depending upon the particular nucleic acid detection methods used, the aptamers may be detected while still a part of the aptamer affinity complex.

Dual Catch Affinity Assay. In another embodiment, a test sample is contacted with an aptamer that includes a releasable first tag and has a specific affinity for a target molecule. If the test sample contains the target molecule, an aptamer affinity complex will form in the mixture with the test sample. The aptamer affinity complex is captured on a first solid support by exposing the mixture to the first solid support. The attachment is accomplished by contacting a first solid support with the aptamer affinity complex and allowing the releasable first tag included on the aptamer to associate, either directly or indirectly, with an appropriate first capture agent that is attached to the first solid support. Note that in addition to aptamer affinity complexes, uncomplexed aptamer will also attach to the first solid support. The aptamer affinity complex and uncomplexed aptamer that has associated with the probe on the solid support is then partitioned from the remainder of the mixture, thereby removing free target and all other uncomplexed matter in the test sample (sample matrix); i.e., components of the mixture not associated with the first solid support. Following partitioning the aptamer affinity complex, along with any uncomplexed aptamer, is released from the first solid support using a method appropriate to the particular releasable first tag being employed. A second tag (which may be the same or different from the releasable first tag) is attached to the target molecule of the aptamer affinity complex. The second tag is designed such that it can be attached to the target in a manner that does not disrupt the aptamer affinity complex. The aptamer affinity complex is captured on a second solid support by allowing the second tag to associate either, directly or indirectly, with an appropriate second capture agent that is attached to a second solid support by exposing the released aptamer affinity complex to the second solid support. The aptamer affinity complex that has associated with the probe on the solid support is partitioned from the remainder of the mixture, thereby removing any free, uncomplexed, aptamer. The aptamers that are complexed with the target in the aptamer affinity complex can be released from the solid support by dissociation of the aptamer affinity complex. Finally, the aptamers that have been released from the aptamer affinity complex can be detected and/or quantified using any of a variety of suitable nucleic acid methods, including but not limited to mass spectrometry, the Invader assay method, a DNA chip, quantitative polymerase chain reaction (Q-PCR), and the like. In some embodiments, the target may be reacted with the second tag while the aptamer affinity complex is still immobilized to the first solid support. Adding the second tag after the partitioning step eliminates the labeling of target molecules that are not part of an aptamer affinity complex. In some embodiments, where a nucleic acid detection method is used, the aptamers may be detected while still a part of the aptamer affinity complex.

Single Catch Photocrosslink Assay. In another embodiment, a test sample is contacted with a photoaptamer that has a specific affinity for a target molecule. If the test sample contains the target molecule, a photoaptamer affinity complex will form in the mixture with the test sample. The aptamer affinity complex is converted to an aptamer covalent complex by the appropriate excitation of the photocrosslinking group. A tag is attached to the target molecule of the aptamer covalent complex. The tag is designed such that it can be attached to the target in a manner that does not disrupt the aptamer covalent complex. The aptamer covalent complex is captured on a solid support by exposing the mixture to the solid support. The attachment is accomplished by contacting the solid support with the aptamer covalent complex and allowing the tag to associate either, directly or indirectly, with an appropriate capture agent that is attached to the solid support. The aptamer covalent complex that has associated with the capture agent on the solid support is partitioned from the remainder of the test sample mixture, thereby removing any free photoaptamer. The photoaptamer that is part of the aptamer covalent complex can be detected and/or quantified (while still attached to the solid support) using any of a variety of methods, including but not limited to the Invader assay method, mass spectroscopy, a DNA chip, quantitative polymerase chain reaction (Q-PCR), and the like.

In another embodiment, the Single Catch Photocrosslink Assay described above is modified such that, prior to detection of the photoaptamer, a nucleic acid amplification step, such as, for example, polymerase chain reaction, is used to create one or more copies of the photoaptamers that are a part of the aptamer covalent complexes that are bound to the solid support. These copies of the photoaptamers can then be released and subsequently detected and/or quantified using any of a variety of suitable methods, including but not limited to mass spectrometry, the Invader assay method, a DNA chip, quantitative polymerase chain reaction (Q-PCR), and the like.

In another embodiment of the Single Catch Photocrosslink Assay, the photocrosslinking group of the photoaptamer is attached to the aptamer via a cleavable linker. In one embodiment, this cleavable linker is a photocleavable linker, but may be a chemically cleavable linker or any other cleavable linker that can be cleaved to release the target molecule from the tag at any desirable point in the assay. In this embodiment, the Single Catch Photocrosslink Assay described above is modified such that, prior to detection of the photoaptamer, the cleavable linker is used to release the photoaptamer from the photoaptamer covalent complex that is bound to the solid support. The released aptamers can be detected and/or quantified using any of a variety of suitable methods, including but not limited to mass spectrometry, the Invader assay method, a DNA chip, quantitative polymerase chain reaction (Q-PCR), and the like.

In yet another embodiment of the Single Catch Photocrosslink Assay, the tag that is attached to the target molecule is attached via a cleavable linker. In one embodiment, this cleavable linker is a photocleavable linker. In other embodiments of this assay, the tag is attached via a chemically cleavable linker or any other suitable cleavable linker that can be cleaved to release the target molecule from the tag at any desirable point in the assay. In this embodiment, the Single Catch Photocrosslink Assay described above is modified such that, prior to detection of the photoaptamer, the cleavable linker is used to release the aptamer covalent complex from the solid support. The released aptamer covalent complex can be detected and/or quantified using any of a variety of suitable methods, including but not limited to mass spectrometry, the Invader assay method, a DNA chip, quantitative polymerase chain reaction (Q-PCR), and the like.

Dual Catch Photocrosslink Assay. In another embodiment, a test sample is contacted with a photoaptamer that contains a first releasable tag and that has a specific affinity for a target molecule. If the test sample contains the target molecule, a photoaptamer affinity complex will form in the mixture with the test sample. The photoaptamer affinity complex is converted to an aptamer covalent complex by the appropriate excitation of the photocrosslinking group. The aptamer covalent complex is captured on a first solid support by exposing the mixture to the first solid support. The attachment is accomplished by contacting a first solid support with the aptamer covalent complex and allowing the releasable first tag included on the photoaptamer to associate either, directly or indirectly, with an appropriate first capture agent attached to the first solid support. Note that in addition to photoaptamer covalent complexes, uncomplexed photoaptamers may also attach to the solid support. The aptamer covalent complex and uncomplexed aptamer that has associated with the probe on the solid support is partitioned from the remainder of the mixture, thereby removing free target and all other uncomplexed matter in the test sample (sample matrix). Following partitioning the photoaptamer covalent complex, along with any uncomplexed photoaptamer, is released from the solid support using a method appropriate to the particular releasable first tag being employed. A second tag is attached to the target molecule of the aptamer covalent complex. The second tag is designed such that it can be attached to the target in a manner that does not disrupt the aptamer covalent complex. The aptamer covalent complex is captured on a second solid support by exposing the released aptamer covalent complex to the second solid support. The attachment is accomplished by contacting the second solid support with the aptamer covalent complex and allowing the second tag to associate either, directly or indirectly, with an appropriate second capture agent attached to the second solid support. The aptamer covalent complex that has associated with the second capture agent on the solid support is partitioned from the remainder of the mixture, thereby removing any free photoaptamer. The photoaptamer that is part of the aptamer covalent complex can be detected and/or quantified (while still attached to the solid support) using any of a variety of suitable methods, including but not limited to the Invader assay method, mass spectroscopy, a DNA chip, quantitative polymerase chain reaction (Q-PCR), and the like.

In another embodiment, the Dual Catch Photocrosslink Assay described above is modified such that, prior to detection, a nucleic acid amplification step such as, for example, polymerase chain reaction, is used to create one or more copies of the photoaptamers that are a part of the aptamer covalent complex that is bound to the solid support. These copies of the photoaptamer can be released and subsequently detected and/or quantified using any of a variety of suitable methods, including but not limited to mass spectrometry, the Invader assay method, a DNA chip, quantitative polymerase chain reaction (Q-PCR), and the like.

In another embodiment, the Dual Catch Photocrosslink Assay described above is modified such that the photocrosslinking group of the photoaptamer is attached to the aptamer via a cleavable linker. In one embodiment, this cleavable linker is a photocleavable linker. In other embodiments of this assay, the photocrosslinking group of the photoaptamer is attached to the aptamer via a chemically cleavable linker or any other suitable cleavable linker that can be cleaved to release the photocrosslinking group from the photoaptamer covalent complex at any desirable point in the assay. In this embodiment, the Dual Catch Photocrosslink Assay described above is modified such that, prior to detection of the photoaptamer, the cleavable linker is used to release the photoaptamer from the photoaptamer covalent complex that is bound to the solid support. The released photoaptamers can be detected and/or quantified using any of a variety of suitable methods, including but not limited to mass spectrometry, the Invader assay method, a DNA chip, quantitative polymerase chain reaction (Q-PCR), and the like.

In yet another embodiment, in the Dual Catch Photocrosslink Assay the tag that is attached to the target molecule is attached via a cleavable linker. In one embodiment, this cleavable linker is a photocleavable linker. In other embodiments of this assay, the tag is attached via a chemically cleavable linker or any other suitable cleavable linker that can be cleaved to release the target molecule from the tag at any desirable point in the assay. In this embodiment, the Dual Catch Photocrosslink Assay described above is modified such that, prior to detection of the photoaptamer, the cleavable linker is used to release the photoaptamer covalent complex from the solid support. The released photoaptamer covalent complex can be detected and/or quantified using any of a variety of suitable methods, including but not limited to mass spectrometry, the Invader assay method, a DNA chip, quantitative polymerase chain reaction (Q-PCR), and the like.

Kinetic Challenge. In another embodiment, a kinetic challenge may be used to increase the specificity and sensitivity of the assays disclosed herein. The kinetic challenge, first described in U.S. application Ser. No. 11/623,580 and U.S. application Ser. No. 11/623,535, each of which was filed on Jan. 16, 2007 and the contents of both of which are incorporated by reference herein in their entireties, provides for using the relatively long off-rates of specific aptamer target complexes relative to non-specific complexes to increase the specificity of certain assays. Furthermore, U.S. application Ser. No. 12/175,434, filed Jul. 17, 2008 entitled "Method for Generating Aptamers with Improved Off-Rates", which is incorporated herein by reference in its entirety, discloses that slow off-rate aptamers can be identified by employing a slow off-rate enrichment process during the SELEX process and/or by using certain modified nucleotides. (See, U.S. application Ser. No. 12/175,388, filed Jul. 17, 2008 entitled "Improved SELEX and PhotoSELEX" which is incorporated herein by reference in its entirety).

The above described assays (the Single Catch Affinity Assays, the Dual Catch Affinity Assays, the Single Catch Photocrosslink Assay, and the Dual Catch Photocrosslink Assay) can each be improved through the incorporation of a kinetic challenge. For purposes of illustration only, the following describes how a kinetic challenge can be added to selected embodiments of the Dual Catch Affinity Assay and the Dual Catch Photocrosslink Assay. It should be understood that a kinetic challenge can be added to the any of other assays and methods described herein in a similar manner. It should be further understood that the kinetic challenge can be added at any suitable point in any of the described assays and methods in addition to the places (steps) noted in the various embodiments described herein.

In one embodiment, a kinetic challenge is inserted into the Dual Capture Affinity Assay after the step in which the aptamer affinity complex and uncomplexed aptamer that has associated with the probe on the first solid support is partitioned from the remainder of the mixture and before the step in which the aptamer in the aptamer affinity complex is either released or is directly detected or quantified. In one embodiment, the kinetic challenge is performed after the aptamer affinity complex is released from the first solid support. In this embodiment, the kinetic challenge is performed by releasing the aptamer affinity complex into a buffer that contains a high concentration of a competitor and subsequently incubating the aptamer affinity complexes in the competitor solution for a time less than or equal to the dissociation half life of the aptamer affinity complex.

In another embodiment, a kinetic challenge is inserted into the Dual Capture Photocrosslink Assay after the formation of the aptamer affinity complex and before the crosslinking step. In one embodiment, the kinetic challenge is performed by adding a competitor to the mixture containing the aptamer affinity complex and subsequently incubating the aptamer affinity complexes in the competitor solution for a time less than or equal to the dissociation half life of the aptamer affinity complex.

Detection and Quantification Methods. As mentioned above, it is possible to detect the aptamer affinity complex (or aptamer covalent complex in the case of the photocrosslink assays) by employing a number of different nucleic acid detection techniques, including mass spectrometry, the Invader assay, DNA chips, quantitative PCR methods, and the like.

In one embodiment, the aptamer affinity complex (or aptamer covalent complex) is detected and/or quantified using a DNA chip. In this embodiment, the aptamer affinity complex (or aptamer covalent complex) that has associated with the solid support is eluted and is hybridized to a complementary probe sequence that has been printed on a DNA chip. In one embodiment, the complementary probe sequence is complementary to the entire aptamer. In another embodiment, the complementary probe sequence is complementary to only a portion of the aptamer. In another embodiment, the probe is complementary to a sequence added to the aptamer for the purpose of hybridization. In order to detect the hybridized aptamer (or photoaptamer) on the DNA chip, a label can be introduced. In one embodiment, the label is incorporated into the aptamer at the time the aptamer (or photoaptamer) is synthesized. For example, a fluorescent dye can be incorporated into a chemically (or enzymatically) synthesized aptamer. In one embodiment, a label is added to the aptamer during synthesis of the aptamer. In other embodiments, a label is added to the aptamer at any time before, during or after the assay. In another embodiment, nucleic acid amplification techniques such as PCR can be used to amplify the aptamer (or photoaptamer) population. In this case, a label can also be incorporated as a part of the amplification step.

In another embodiment, the aptamer affinity complex (or aptamer covalent complex) is detected and/or quantified using mass spectrometry. In this embodiment, the aptamer affinity complex (or aptamer covalent complex) that has associated with the solid support is eluted and analyzed using mass spectrometry, which produces a spectrum of peaks that can be used to identify, and therefore detect, the target molecule. Once the target molecule has been detected, optionally it can also be quantified by any number of suitable techniques. In one embodiment, where the target molecule is a protein or polypeptide, prior to using mass spectrometry to analyze the aptamer affinity complex (or aptamer covalent complex), the aptamer affinity complex (or aptamer covalent complex) can be digested with protease enzymes, such as, for example, proteinase K or trypsin, to produce fragments of the bound target molecule that can be used to identify the target molecule, and thereby enable detection and optional quantification of the target molecule.

In another embodiment, the aptamer affinity complex (or aptamer covalent complex) is detected and/or quantified using Q-PCR. As mentioned above, this can be done either while the aptamer affinity complex (or aptamer covalent complex) is attached to the solid support or after release from the solid support. The aptamer affinity complex (or aptamer covalent complex) is quantified by performing PCR and determining, either directly or indirectly, the amount or concentration of aptamer that had bound to its target molecule in the test sample. The amount or concentration of the target molecule in the test sample is generally directly proportional to the amount or concentration of the aptamer quantified by using Q-PCR. An exemplary method that may be employed to quantify an aptamer affinity complex (or aptamer covalent complex) in this manner is the TaqMan® assay (PE Biosystems, Foster City, Calif.; see also U.S. Pat. No. 5,210,015).

In another embodiment, the aptamer is optionally dissociated from its corresponding target molecule, prior to detection and/or quantification. The free aptamer can be detected and measured using any known suitable method for the detection and/or quantification of nucleic acids.

Multiplexed Assays. In another embodiment, the assays and methods described above are used to detect and/or quantify two or more targets. In one embodiment, multiple aptamers are used in the Dual Capture Affinity Assay to quantify and/or detect multiple targets. After final release of the aptamers from the aptamer affinity complexes, each of the aptamers can then be detected using suitable methods for the multiplexed detection of nucleic acids. In one method, a multiplexed DNA chip is used to detect and/or quantify the aptamers. Any of the assays disclosed herein can be performed in a multiplexed fashion to detect multiple targets. Because there are no inherent limits to the scale of the multiplexing, these multiplexed assays can be used to detect, for example, 2 or more targets, 10 or more targets, 25 or more targets, 50 or more targets, 100 or more targets, 250 or more targets, 500 or more targets, or 1000 or more targets.

Reagents and Kits. In one embodiment, kits for various detection applications, including without limitation diagnostic kits, biomarker discovery kits, environmental testing kits, biohazard or bioweapons detection kits and kits for detecting targets in life science and analytical chemistry applications, can be prepared based on the methods disclosed herein.

BRIEF DESCRIPTION OF THE FIGURES

FIGS. 3A-3L illustrate exemplary aptamer constructs for use with the assays described herein.

FIG. 4 presents a list of over 500 targets for which aptamers have been produced. Many of these aptamers have been designed to have slow dissociation rates from their respective target.

FIG. 6 illustrates the aptamer and primer constructs used in the assay methods described in this disclosure. Cy3 represents a Cyanine 3 dye, B a biotin, PC a photocleavable linker, ANA a photoreactive crosslinking group, $(AB)_2$ a pair of biotin residues separated by dA residues, and $(T)_8$ a poly dT linker. Primer constructs are complementary to the complete 3' fixed region of the aptamer constructs.

FIG. 6A. Aptamer construct used in the Single Catch Affinity Assay Protocol.

FIG. 6B. Aptamer construct used in the Dual Catch Affinity Assay Protocol.

FIG. 6C. Aptamer construct used in the Single Catch Crosslinking Assay Protocol.

FIG. 6D. Aptamer construct used in the Dual Catch Crosslinking Assay Protocol.

FIG. 7A. bFGF target protein. FIG. 7B. FGF7 target protein. FIG. 7C. Lymphotactin target protein.

DETAILED DESCRIPTION

Figure 1A:
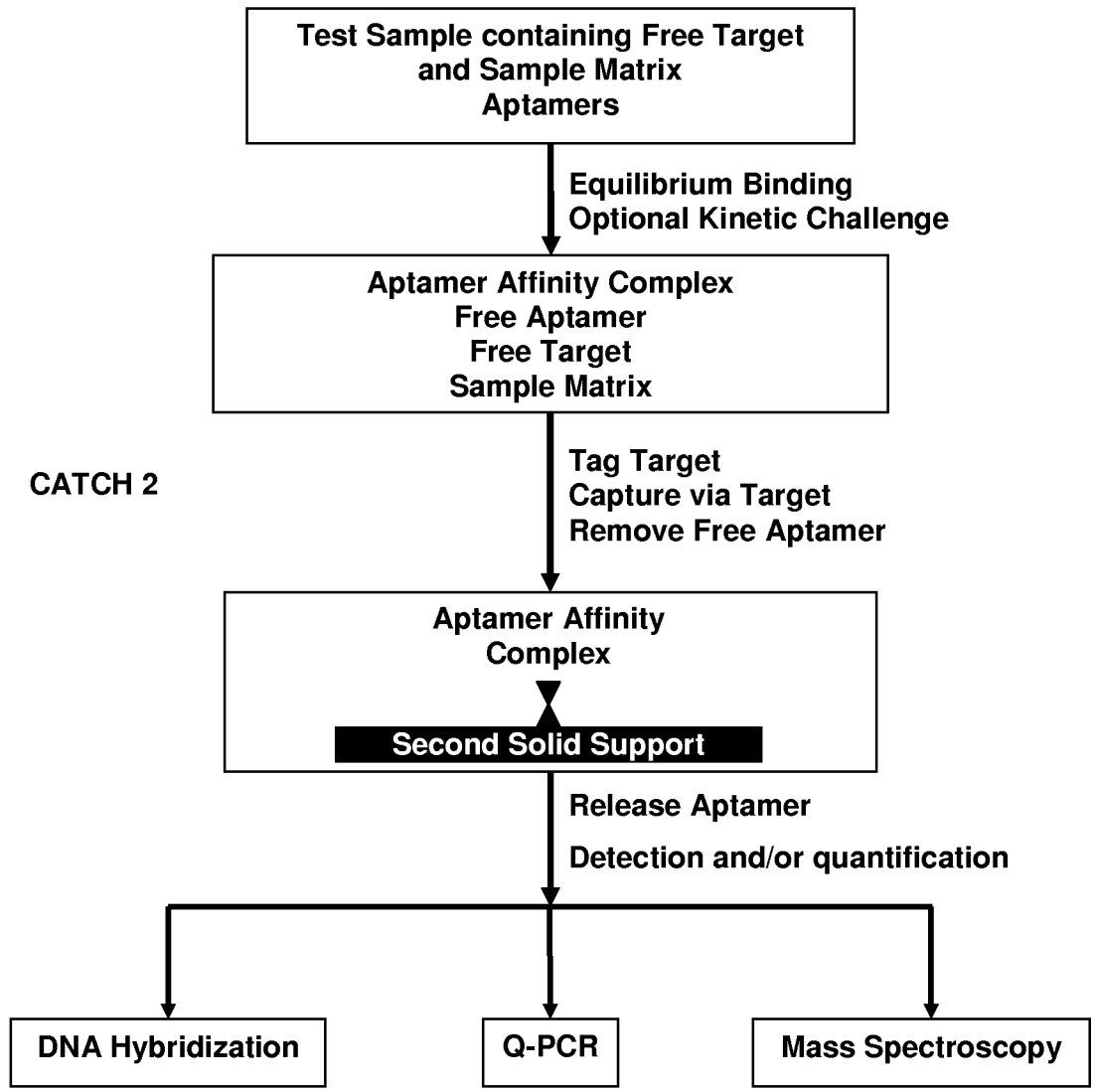
FIGS. 1A and 1B illustrate exemplary methods for the detection and/or quantification of one or more target molecules that may be present in a test sample.

The practice of the current invention employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

The present disclosure includes improved methods, devices, reagents, and kits for the detection and/or quantification of one or more target molecules that may be present in a test sample. The disclosed methods, devices, reagents, and kits provide high sensitivity assays for the detection and/or quantification of target molecules in a test sample by optimizing conditions that affect one or more of (1) the activity of aptamers, (2) the efficiency of achieving binding equilibria for aptamer-target molecule complexes, (3) the formation of covalent bond(s) between an aptamer and its target molecule, (4) the removal of excess reagents and sample components, (5) the use of slow off rate aptamers, (6) desirable aptamer constructions, and (7) the detection of aptamer-target molecule complexes.

It is noteworthy that, unless otherwise specified in a particular embodiment, the methods for the detection and/or quantification of a target molecule described herein are independent of the specific order in which the steps are described. For purposes of illustration, the methods are described as a specific sequence of steps; however, it is to be understood that any number of permutations of the specified sequence of steps is possible, so long as the objective of the particular assay being described is accomplished. Stated another way, the steps recited in any of the disclosed methods may be performed in any feasible order, and the methods of the invention are not limited to any particular order presented in any of the described embodiments, the examples, or the appended claims. Further, for convenience and ease of presentation, the various methods are described with reference to a single target molecule and a single aptamer. However, it is to be understood that any of the described methods can be performed in a multiplex format that can provide for the simultaneous detection and/or quantification of multiple targets using multiple aptamers, such that, for example, multiple target molecules in a test sample can be detected and/or quantified by contacting the test sample with multiple aptamers, wherein each aptamer has a specific affinity for a particular target molecule (i.e., in a multiplex format).

Figure 1B:
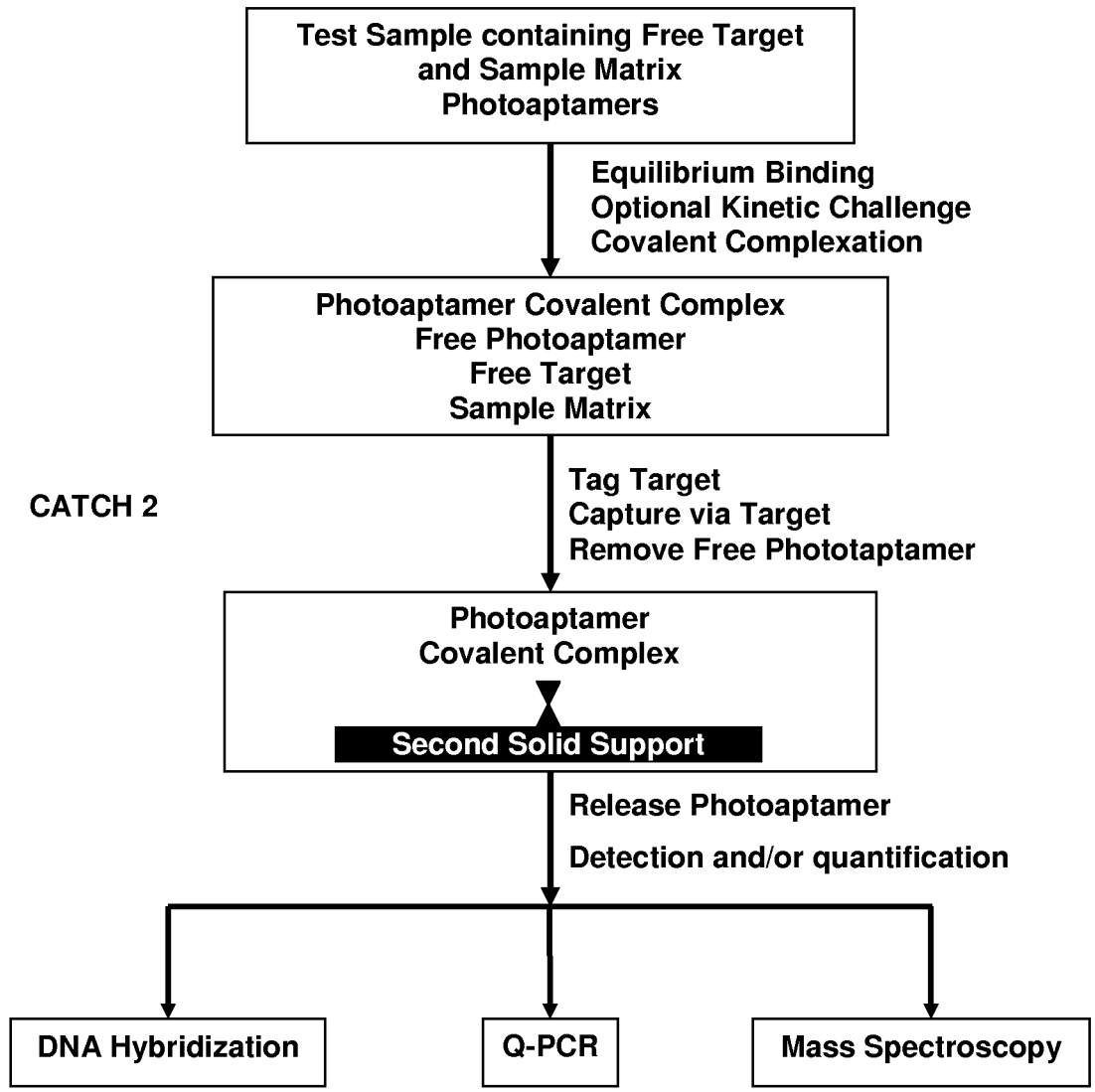

With reference to FIGS. 1A and 1B, the presence of a target molecule in a test sample is detected and/or quantified by first contacting a test sample with an aptamer that has a specific affinity for a target molecule. The method may be applied to the detection and/or quantification of a number of specific targets by use of the corresponding number of specific aptamers, i.e. a multiplex format. A single target discussion is presented only for ease of presentation. An aptamer affinity complex is formed by the aptamer binding to its target molecule if the test sample contains the target molecule. The aptamer affinity complex is optionally converted, using a method appropriate to the aptamer being employed, to an aptamer covalent complex where the aptamer is covalently bound to its target molecule. A partition step is then employed to remove free aptamer. The aptamer affinity complex (or aptamer covalent complex) is detected and/or quantified. A number of different detection methods can be used to detect the aptamer affinity complex, for example, the Invader assay, hybridization assays or DNA chips, mass spectroscopy, or Q-PCR.

As discussed above, the assays described here have been grouped for ease in presentation into 4 assay formats: Single Catch Affinity Assays; Dual Catch Affinity Assays, Single Catch Photocrosslink Assays; and Dual Catch Photocrosslink Assays. However, it should be understood that other groupings, combinations, and ordering of steps are contemplated and all fall within the scope of the disclosure. All four assay formats share a common step in which aptamer-target complexes are separated from free aptamer (or free photoaptamer) by a partitioning step that captures the target, such as, for example, protein. This partitioning step is referred to herein as the "Catch 2" partition. The two "dual-catch" assays share an additional commonality in which aptamer-target complexes are separated from free target by a partitioning step that captures the aptamer. This latter partitioning step is referred to herein as the "Catch 1" partition. Methods for implementing each of these steps are described in detail below.

The use of a kinetic challenge in each of these assay formats is further disclosed. Traditionally, specificity in the detection of a desired target has been improved through the use of a sandwich assay in which two capture reagents are used. It has surprisingly been observed that the application of a kinetic challenge to a detection procedure employing aptamers eliminates the need to enhance specificity by introducing a second capture reagent. If a kinetic challenge is introduced, non-specific complexes between the aptamer and any non-target molecules are unlikely to re-form following their dissociation. Since non-specific complexes generally dissociate more rapidly than an aptamer affinity complex, a kinetic challenge reduces the likelihood that an aptamer will be involved in a non-specific complex with a non-target. An effective kinetic challenge can provide the assay with additional specificity, beyond that of the initial aptamer binding event and any subsequent covalent interaction. Thus, the kinetic challenge offers a second determinant of specificity in these detection methods. Methods for implementing the kinetic challenge are described in detail below.

Figure 2A:
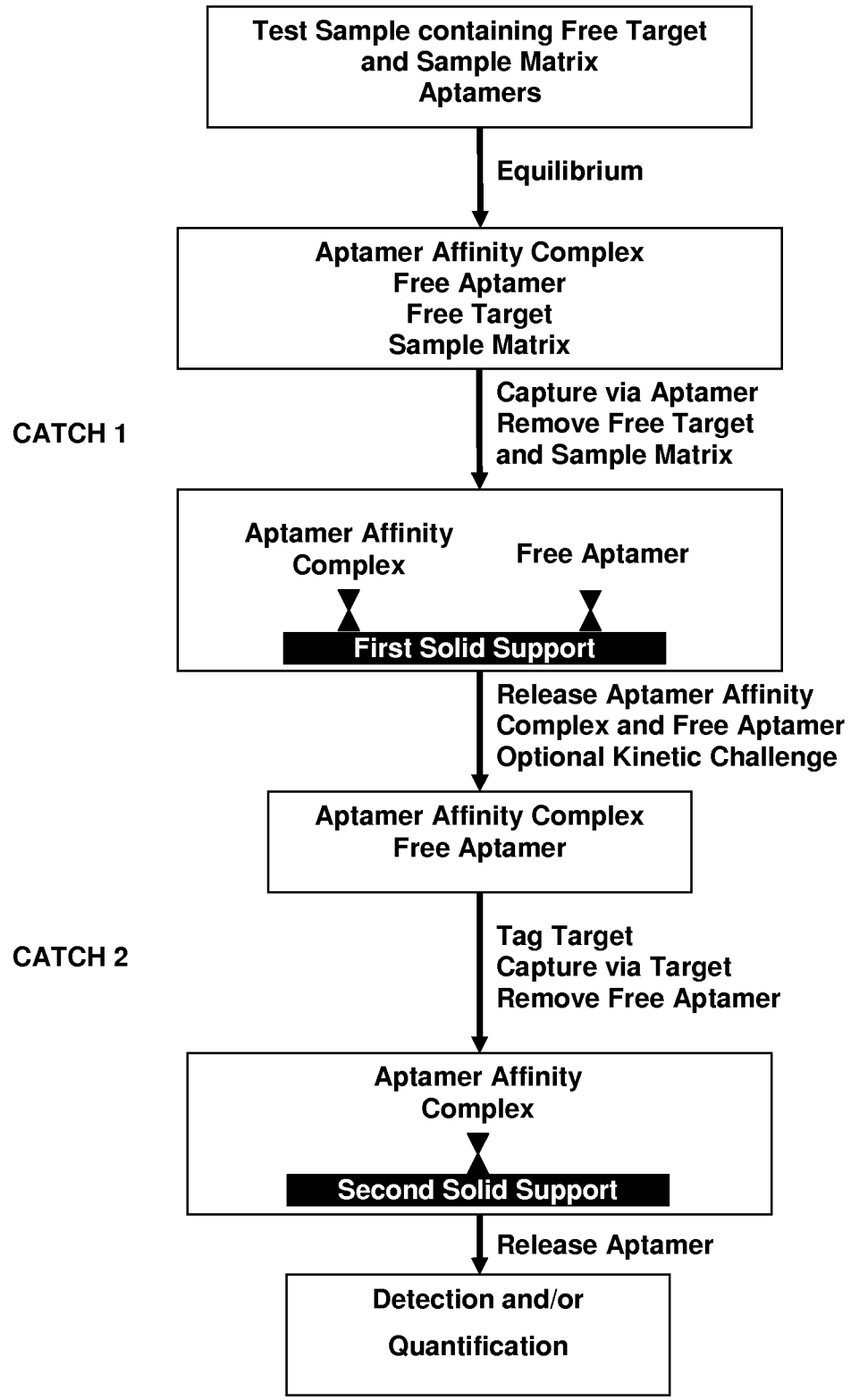
FIGS. 2A and 2B illustrate exemplary methods for the detection and/or quantification of one or more target molecules that may be present in a test sample.

With reference to FIGS. 2A (dual step affinity assay) and 2B (dual step crosslinking assay), in an exemplary method for the detection and/or quantification of a target molecule that may be present in a test sample, a test sample is contacted with an aptamer (or photoaptamer) that includes a first tag and has a specific affinity for a target molecule. An aptamer affinity complex that includes an aptamer (or photoaptamer) bound to its target molecule is allowed to form, where the test sample contains the target molecule. In the photocrosslinking example (2B), the aptamer affinity complex is converted, using a method appropriate to the aptamer being employed, to an aptamer covalent complex where the photoaptamer is covalently bound to its target molecule. The aptamer affinity complex (or aptamer covalent complex) is attached to a first solid support via a first capture element. The attachment is accomplished by contacting the first solid support with the aptamer affinity complex (or aptamer covalent complex) and allowing the tag included on the aptamer to associate either, directly or indirectly, with a first capture element that is attached to the first solid support. The aptamer affinity complex (or aptamer covalent complex) that has associated with the first capture element on the first solid support is partitioned from the remainder of the mixture. Following partitioning the aptamer affinity complex (or aptamer covalent complex) is released from the first solid support using a method appropriate to the particular tag being employed. Alternatively, the tag can be attached the aptamer via a cleavable moiety, where such cleavable moiety is now cleaved to release the aptamer affinity (or aptamer covalent complex) from the first solid support. A second tag (which may be the same or different from the first tag) is attached to the target molecule of the aptamer affinity complex (or aptamer covalent complex). Optionally, a kinetic challenge can be performed to increase the assay specificity and decrease the background signal. The aptamer affinity complex (or aptamer covalent complex) is attached to a second solid support. The attachment is accomplished by contacting the second solid support with the aptamer affinity complex (or aptamer covalent complex) and allowing the second tag included on the target to associate either, directly or indirectly, with a second capture element that is attached to the second solid support. The aptamer affinity complex (or aptamer covalent complex) that has associated with the second capture element on the second solid support is partitioned from the remainder of the mixture. The aptamer affinity complex (or aptamer covalent complex) is detected and optionally quantified.

In another embodiment, the aptamer (or photoaptamer) is first dissociated from its respective target molecule and the free aptamer (or photoaptamer) is detected and optionally quantified.

The aptamer affinity complex can be detected by utilizing any suitable nucleic acid detection technique, such as, for example, hybridization or a DNA chip, Q-PCR, mass spectroscopy (MS), the Invader assay, and the like. Depending on which technique is employed, the aptamer may be designed or modified to include a label. This can be accomplished during synthesis (either enzymatically or chemically) or at any time during the assay (i.e., at any time prior to detection).

The methods disclosed herein enable the detection of the presence and amount of a target molecule by detecting free aptamer eluted from the assay. This allows for convenient detection and quantification of the target molecule, due to the relative simplicity of detection, quantification, and amplification of nucleic acids, and provides target detection assays that have a very favorable signal-to-noise ratio.

Single Catch (Catch 2-Only) Affinity Assay

In one embodiment, a single catch affinity assay is performed using a catch 2 partition, see FIG. 1A or 1B. This method works well when the sample matrix is not very complex so that other components in the sample do not compete for the tag. It also works well for samples in which the target is present in high copy number or concentration.

Aptamers having high affinity and specificity for a target molecule are provided. In one embodiment, the aptamer construct illustrated in FIG. 6A is used. In this embodiment, the aptamer is contacted with a sample that may contain a target molecule to form a mixture containing the aptamer, the target molecule, and non-target molecules, or sample matrix. Where the target molecule is present in the sample, aptamer affinity complexes are formed. The mixture may optionally be incubated for a period of time sufficient to achieve equilibrium binding of the aptamer to the target molecule, (e.g., at least about 10 minutes, at least about 20 minutes, at least about 30 minutes).

In one embodiment, the mixture may optionally be subject to a kinetic challenge. The kinetic challenge helps reduce any non-specific binding between the aptamer and any non-target molecules present in the sample. In one embodiment, 10 mM dextran sulfate is added and the mixture is incubated for about 15 minutes.

In one embodiment, the catch-2 partition is performed to remove free aptamer. In one embodiment, the mixture containing aptamer affinity complexes is treated with an agent that introduces a capture tag to the target molecule component of the aptamer affinity complexes. In other embodiments, the tag is introduced before the aptamer is contacted with the text mixture, either before equilibrium binding or before the kinetic challenge. In one embodiment, the target is a protein or peptide, and a biotin tag is attached to the target molecule by treating with NHS-PEO4-biotin. The mixture is then contacted with a solid support, that has a capture element adhered to its surface which is capable of binding to the target capture tag. In this embodiment, the capture element on the solid support is typically selected such that it binds to the target capture tag with high affinity and specificity. In one embodiment, the solid support is magnetic beads (such as DynaBeads MyOne Streptavidin C1) contained within a well of a microtiter plate and the capture element is streptavidin. The magnetic beads provide a convenient method for the separation of partitioned components of the mixture. Aptamer affinity complexes contained in the mixture are thereby bound to the solid support through the binding interaction of the target capture tag and capture element on the solid support. The aptamer affinity complex is then partitioned from the remainder of the mixture, e.g. by washing the support to remove non-complexed aptamers. In one embodiment, aptamer from the aptamer affinity complex can then be released for further processing by one or more of the following treatments: high salt, high pH, low pH or elevated temperature.

In another embodiment, the aptamer released from the catch-2 partition is detected and optionally quantified by any suitable nucleic acid detection methods, such as, for example, DNA chip hybridization, Q-PCR, mass spectroscopy, the Invader assay, and the like. In another embodiment the aptamer in the aptamer affinity complex is detected and optionally quantified while still in contact with the solid support. In one embodiment, the aptamer comprises a detectable moiety to facilitate this detection step. The detectable moiety is chosen based on the detection method to be employed. In one embodiment, the detectable moiety or label is added to the aptamer during synthesis or prior to the assay. In another embodiment, the detectable moiety is added to the aptamer either during the assay or during the detection. The detected aptamer can then be correlated with the amount or concentration of target in the original test sample.

Dual Catch (Catch 1 & 2) Affinity Assay

In one embodiment, a dual catch affinity assay is similar to the single catch affinity assay, but with an additional partitioning step to provide additional sensitivity and specificity. In one embodiment, aptamers having high affinity and specificity for a target molecule and having a first releasable tag are provided. In another embodiment, the first releasable tag is added at any time in the assay prior to the catch 1 partition, see FIGS. 2A and 2B. In one embodiment, this first releasable tag is a photocleavable biotin. In one embodiment, the aptamer construct illustrated in FIG. 6B is used. These and other tags and cleavable moieties and aptamer containing such tags and cleavable moieties are described. The aptamer is contacted with a sample that may contain a target molecule to form a mixture containing the aptamer, the target molecule, and non-target molecules, or sample matrix. Where the target molecule is present in the sample, aptamer-target molecule complexes (aptamer affinity complexes) are formed. The mixture may optionally be incubated for a period of time sufficient to achieve equilibrium binding of the aptamer to the target molecule (e.g., at least about 10 minutes, at least about 20 minutes, at least about 30 minutes).

In one embodiment, the catch 1 partition is performed to remove any free target and sample matrix. The mixture is contacted with a first solid support having a first capture element adhered to its surface which is capable of binding to the aptamer capture tag, preferably with high affinity and specificity. In one embodiment, the first releasable tag is a photocleavable biotin, the first solid support is agarose beads in a column and the capture element is streptavidin. For example, Pierce Immobilized Streptavidin beads may be used. Aptamer affinity complexes contained in the mixture are thereby bound to the first solid support through the binding interaction of the first releasable tag and first capture element. The aptamer affinity complexes are partitioned from the remainder of the mixture, e.g. by washing the first solid support to remove non-bound molecules.

In one embodiment, aptamer affinity complexes bound to the solid support are then treated with an agent that introduces a second tag to the target molecule component of the aptamer affinity complexes. In one embodiment, the target is a protein or a peptide, and the target is biotinylated by treating it with NHS-PEO4-biotin. The second tag introduced to the target molecule may be the same as or different from the aptamer capture tag. If the second tag is the same as the first tag, or the aptamer capture tag, free capture sites on the first solid support may be blocked prior to the initiation of this tagging step. In this exemplary embodiment, the first solid support is washed with free biotin prior to the initiation of target tagging. Tagging methods, and in particular, tagging of targets such as peptides and proteins are described. In other embodiments, tagging of the target is performed at any other point in the assay prior to initiation of the catch 2 partitioning, see FIGS. 2A and 2B. When the first and second tags are the same, the target is tagged after the capture step of the catch 1 partitioning has been performed.

Figure 2B:
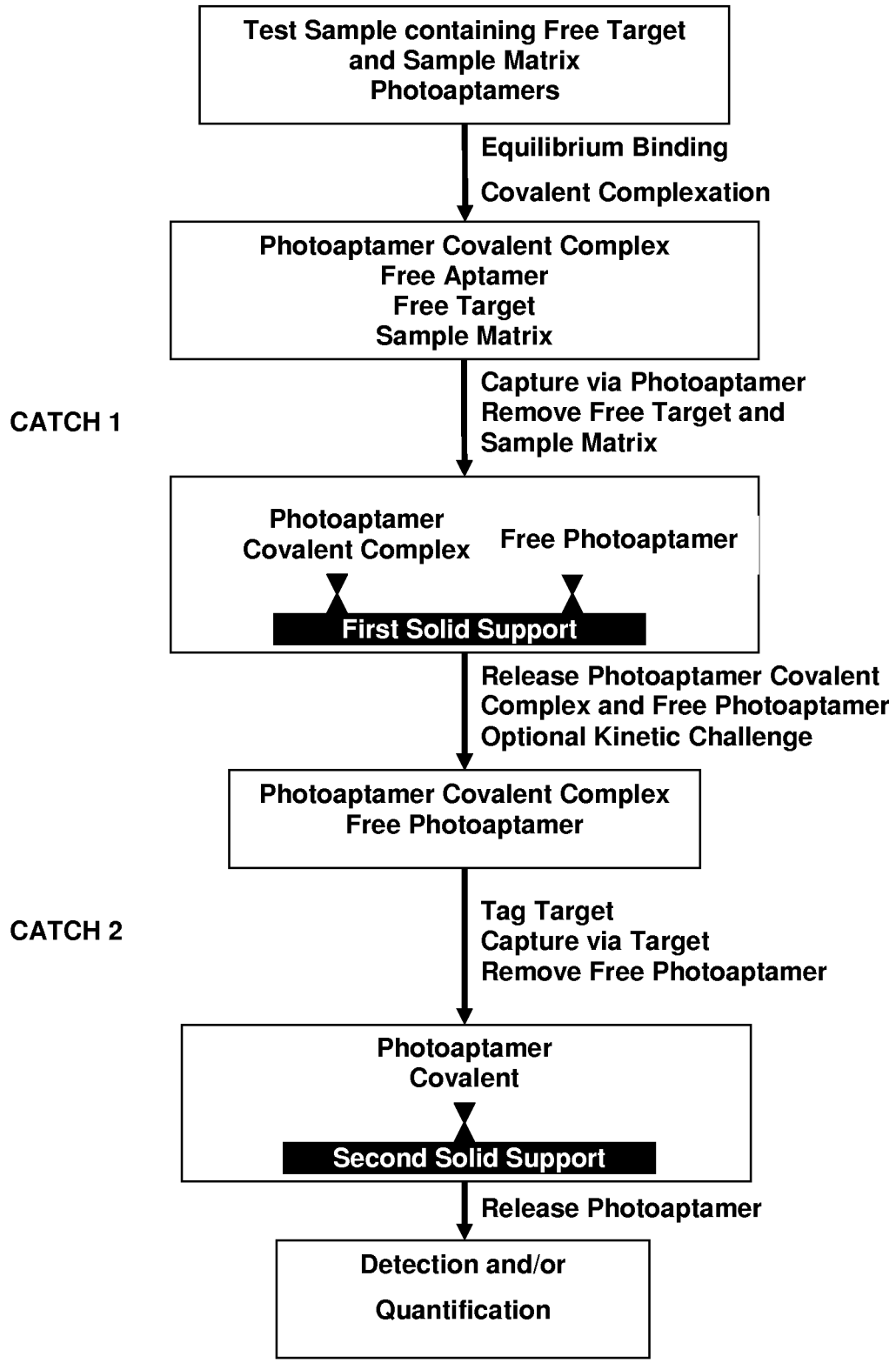

Catch 1 partitioning is completed by releasing of the aptamer affinity complexes from the first solid support. In one embodiment, the first releasable tag is a photocleavable moiety that is cleaved by irradiation with a UV lamp under conditions that cleave ≥ about 90% of the first releasable tag. In other embodiments, the release is accomplished by the method appropriate for the selected releasable moiety in the first releasable tag. Aptamer affinity complexes may be eluted and collected for further use in the assay or may be contacted with another solid support to conduct the remaining steps of the assay (FIGS. 2A and 2B).

In one embodiment, the mixture may optionally be subject to a kinetic challenge. The kinetic challenge helps reduce any non-specific binding between aptamers and non-target molecules. In one embodiment, 10 mM dextran sulfate is added to the aptamer affinity complexes, and the mixture is incubated for about 15 minutes. In another embodiment, the kinetic challenge is initiated by performing the catch 1 elution in the presence of 10 mM dextran sulfate. In other embodiments, the kinetic challenge is performed after the equilibrium binding step and before the catch 2 partitioning.

In one embodiment, the catch-2 partition is performed to remove free aptamer. As described above, in one embodiment, a second tag used in the catch-2 partition may be added to the target while the aptamer affinity complex is still in contact with the solid support used in the catch-1 partition. In other embodiments, the second tag may be added to the target at another point in the assay prior to initiation of catch 2 partitioning. The mixture is contacted with a solid support, the solid support having a capture element (second) adhered to its surface which is capable of binding to the target capture tag (second tag), preferably with high affinity and specificity. In one embodiment, the solid support is magnetic beads (such as DynaBeads MyOne Streptavidin C1) contained within a well of a microtiter plate and the capture element (second capture element) is streptavidin. The magnetic beads provide a convenient method for the separation of partitioned components of the mixture. Aptamer affinity complexes contained in the mixture are thereby bound to the solid support through the binding interaction of the target (second) capture tag and the second capture element on the second solid support. The aptamer affinity complex is then partitioned from the remainder of the mixture, e.g. by washing the support to remove non-complexed aptamers. In one embodiment, aptamer from the aptamer affinity complex can then be released for further processing by one or more of the following treatments: high salt, high pH, low pH or elevated temperature.

In another embodiment, the aptamer released from the catch-2 partition is detected and optionally quantified by any suitable nucleic acid detection methods, such as, for example, DNA chip hybridization, Q-PCR, mass spectroscopy, the Invader assay, and the like. These detection methods are described in further detail below. In another embodiment the aptamer in the aptamer affinity complex is detected and optionally quantified while still in contact with the solid support. In one embodiment, the aptamer comprises a detectable moiety to facilitate this detection step. The detectable moiety is chosen based on the detection method to be employed. In one embodiment, the detectable moiety (label) is added to the aptamer during synthesis or any time prior to the assay. In another embodiment, the detectable moiety is added to the aptamer either during the assay or during the detection. The detected aptamer can be correlated to the amount or concentration of the target in the test sample.

Single Catch (Catch 2-Only) Crosslinking Assay

In one embodiment, a single catch crosslinking assay is performed using a catch 2 partition. This method works well when the sample matrix is not very complex so that other components in the sample do not compete for the tag. It also works well for samples in which the target is present in high copy number or concentration. In some cases, additional benefit is provided by forming a covalent link between the photoaptamer and the target as it may allow more stringent washes in steps after the crosslinking has been performed (FIG. 1B).

Photoaptamers having high affinity and specificity for a target molecule are provided. In one embodiment, the crosslinking moiety of the photoaptamer is linked to the aptamer via a cleavable linker. In one embodiment, the crosslinking group is ANA (4-azido-2-nitro-aniline) and the photocleavable group is PC Linker. In one embodiment, the aptamer construct illustrated in FIG. 6C is used. The photoaptamer is contacted with a sample that may contain target molecules to form a mixture containing the aptamer, the target molecule, and non-target molecules, or sample matrix. Where the target molecule is present in the sample, (photo) aptamer affinity complexes are formed. The mixture may optionally be incubated for a period of time sufficient to achieve equilibrium binding of the aptamers and target molecules, (e.g., for at least about 10 minutes, at least about 20 minutes, or at least about 30 minutes).

In one embodiment, the mixture may optionally be subject to a kinetic challenge. The kinetic challenge helps reduce any non-specific binding between photoaptamers and non-target molecules. In one embodiment, 10 mM dextran sulfate is added and the mixture is incubated for about 15 minutes.

In this embodiment, the photoaptamer affinity complexes are converted into aptamer covalent complexes by irradiation with light at the appropriate wavelength. For example, irradiation at about 470 nM can be used to crosslink ANA containing photoaptamers to a protein or peptide target.

In one embodiment, the catch-2 partition is performed to remove free photoaptamer. In one embodiment, the mixture containing the aptamer covalent complex is treated with an agent that introduces a capture tag to the target molecule component of the aptamer covalent complexes. In other embodiments, the tag is introduced before the aptamers are contacted with the test sample, before the equilibrium binding, or before the kinetic challenge. In one embodiment, the target is a protein or a peptide, and a biotin tag is attached to the target molecule by treatment with NHS-PEO4-biotin. The mixture is contacted with a solid support, the solid support having a capture element adhered to its surface which is capable of binding to the target capture tag, preferably with high affinity and specificity. In one embodiment, the solid support is magnetic beads (such as DynaBeads MyOne Streptavidin C1) contained within a well of a microtiter plate and the capture element is streptavidin. The magnetic beads provide a convenient method for the separation of partitioned components of the mixture. Aptamer covalent complexes contained in the mixture are thereby bound to the solid support through the binding interaction of the target capture tag and capture element. The aptamer covalent complex is partitioned from the remainder of the mixture, e.g. by washing the support to remove non-complexed aptamers. In one embodiment, photoaptamer from the aptamer covalent complex can be released for further processing by a method appropriate for the cleavable moiety. For example, to cleave the PC Linker, the mixture is irradiated with a UV lamp for about 20 minutes.

In another embodiment, the photoaptamer released from the catch-2 partition is detected and optionally quantified by any suitable nucleic acid detection method, such as, for example, DNA chip hybridization, Q-PCR, mass spectroscopy, the Invader assay, and the like. These detection methods are described in further detail below. In another embodiment the photoaptamer in the aptamer covalent complex is detected and optionally quantified while still in contact with the solid support. The detected photoaptamer can be correlated with the amount or concentration of target in the original test sample.

Dual Catch (Catch 1 & 2) Photocrosslinking Assay

In one embodiment, a dual catch photocrosslinking assay, similar to the single catch photocrosslinking assay, uses an additional partitioning step to provide additional sensitivity and specificity (FIG. 2B).

Photoaptamers having high affinity and specificity for a target molecule are provided. In one embodiment, the crosslinking moiety of the photoaptamer is linked to the aptamer via a cleavable linker. In one embodiment, the crosslinking group is ANA (4-azido-2-nitro-aniline) and the photocleavable group is a PC Linker. In one embodiment, the photoaptamer also comprises a first releasable tag. In another embodiment, the first releasable tag is added at any time in the assay prior to the catch 1 partition. In one embodiment, the first releasable tag moiety is a biotin and the releasable element is a hybridization linker. In one embodiment, the photoaptamer construct illustrated in FIG. 6D is used. The photoaptamer is contacted with a sample that may contain target molecules to form a mixture containing the aptamer, the target molecule, and non-target molecules, or sample matrix. Where the target molecule is present in the sample, (photo) aptamer affinity complexes are formed. The mixture may optionally be incubated for a period of time sufficient to achieve equilibrium binding of the aptamers and target molecules (e.g., for at least about 10 minutes, at least about 20 minutes, or at least about 30 minutes).

In one embodiment, the mixture may optionally be subject to a kinetic challenge. The kinetic challenge helps reduce any non-specific binding between photoaptamers and non-target molecules. In one particular embodiment, 10 mM dextran sulfate is added and the mixture is incubated for about 15 minutes.

(Photo)aptamer affinity complexes are converted into aptamer covalent complexes by irradiation with light at the appropriate wavelength. For example, irradiation at about 470 nM can be used to crosslink ANA containing photoaptamers to a protein target.

In one embodiment, the catch 1 partition is performed to remove free target and sample matrix. The mixture is contacted with a first solid support having a first capture element adhered to its surface which is capable of binding to the aptamer capture tag, preferably with high affinity and specificity. In one embodiment, the first releasable tag comprises a tag moiety that is a biotin, the first solid support is agarose beads in a column and the first capture element is streptavidin. For example, Pierce Immobilized Streptavidin beads may be used. Aptamer covalent complexes contained in the mixture are thereby bound to the first solid support through the binding interaction of the first releasable tag and first capture element. The aptamer covalent complexes are partitioned from the remainder of the mixture, e.g. by washing the first solid support to remove non-bound molecules.

In one embodiment, aptamer covalent complexes that remain bound to the first solid support are then treated with an agent that introduces a second tag to the target molecule component of the aptamer affinity complexes, e.g. biotinylation of a protein or peptide target molecule by treatment with NHS-PEO4-biotin. The second tag introduced to the target molecule may be the same as or different from the first tag. If the second tag is the same as the first tag, free capture sites on the first solid support may be blocked prior to the initiation of this tagging step. In this embodiment, the first solid support is washed with free biotin prior to the initiation of target tagging. Tagging methods, and in particular, tagging of targets such as peptides and proteins are described in detail below. In other embodiments, tagging of the target is performed at any other point in the assay prior to initiation of catch 2 partitioning. If the first and second tags are the same, the target is tagged after the capture step of the catch 1 partitioning has been performed.

In another embodiment, the catch 1 partitioning is completed by releasing the aptamer covalent complexes from the first solid support. In one embodiment, the first releasable tag is a hybridization tag complementary to all or some of the first capture element on said solid support. This first releasable tag is cleaved by treating the mixture with conditions that will disrupt the hybridization linker, such as high pH. In one embodiment, 20 mM NaOH is added to the mixture. In other embodiments, the release of the aptamer covalent complex is accomplished by any method that is appropriate for the releasable moiety in the first releasable tag. Aptamer covalent complexes may be eluted and collected for further use in the assay or may be contacted with a further solid support in order to conduct the remaining steps of the assay.

In one embodiment, the catch-2 partition is performed to remove free photoaptamer. The mixture is contacted with a solid support that has, a capture element adhered to its surface which is capable of binding to the second capture tag, preferably with high affinity and specificity. In one embodiment, the solid support is magnetic beads (such as DynaBeads MyOne Streptavidin C1) contained within a well of a microtiter plate and the capture element is streptavidin. The magnetic beads provide a convenient method for the separation of partitioned components of the mixture. Aptamer covalent complexes contained in the mixture are thereby bound to the solid support through the binding interaction of the target second capture tag and second capture element. The aptamer covalent complex is then partitioned from the remainder of the mixture, e.g. by washing the support to remove non-complexed aptamers. In one embodiment, photoaptamer from the aptamer covalent complex can then be released for further processing by a method appropriate for the cleavable moiety. For example, to cleave the PC Linker, the mixture is irradiated with a UV lamp for about 20 minutes.

In another embodiment, the photoaptamer released from the catch-2 partition is detected and optionally quantified by any suitable nucleic acid detection method, such as, for example, DNA chip hybridization, Q-PCR, mass spectroscopy, the Invader assay, and the like. In another embodiment the photoaptamer in the aptamer covalent complex is detected and optionally quantified while still in contact with the solid support. The detected photoaptamer can be correlated with the amount or concentration of target in the original test sample.

In any of the embodiments disclosed herein, the test sample may be prepared as two or more dilutions of the test sample, which may increase the dynamic range of target detection by the methods disclosed herein. The individual dilution test samples are separately assayed up to and including aptamer (or covalent) complex formation, after which the dilution test samples may be pooled for the remainder of the assay and detected simultaneously on a single solid support. In one embodiment, each dilution test sample includes a unique aptamer, thereby enabling a single measurement of the corresponding target. In another embodiment, an aptamer can be added to two or more dilutions, each dilution contacting a distinctly tagged aptamer for a particular target, allowing for the detection of a specific aptamer signal for each of the different dilution samples on a single solid support. Chaining together diluted samples in this manner can extend a dynamic range for a single target molecule over many orders of magnitude and add accuracy when overlapping regions of quantification lead to multiple determinations of a single target's concentration.

In any of the embodiments disclosed herein, the beads, or solid support, may be suspended after discarding the supernatant containing un-complexed target and test sample or sample matrix. In one embodiment, prior to eluting the free aptamer and aptamer (or covalent) complex from the beads and at any point up to suspending the beads, the aptamer (or covalent) complex may be contacted with a labeling agent, followed by repeated pelleting and washing to remove unreactive labeling agent prior to contacting the solid support with the aptamer (or covalent) complex for detection and/or quantification of the target molecule.

In one embodiment, a set of test samples is prepared as serial dilutions to which a tagged aptamer (or tagged photoaptamer) with a specific affinity for a target molecule is introduced. The same aptamer with a different tag can be added to each test sample dilution. As further described herein, following the formation of an aptamer affinity complex (or the optional conversion to an aptamer covalent complex) the individual test samples can be pooled and contacted with a labeling agent either before or after attachment of the aptamer (or covalent) complex to the solid support. The target molecule, if present in the test sample, is detected and/or quantified by detecting the labeling agent on the aptamer (or covalent) complex. The resultant signals detected for each aptamer having a different tag can be combined to accurately quantify the amount or concentration of the target molecule in the original test sample. For example, the first dilution may result in a maximal signal for the target, yielding only semi-quantitative information, while the second dilution may result in a signal that is less than saturating, allowing for an accurate quantification of the target in the original test sample.

In another embodiment, a set of test samples is prepared as serial dilutions to which a tagged aptamer (or tagged photoaptamer) with a specific affinity for a target molecule is introduced. Different aptamers having unique tags may be added to each sample dilution. As further described herein, following the formation of aptamer affinity complexes (or the optional conversion to aptamer covalent complexes) the individual test samples can be pooled and contacted with a labeling agent either before or after attachment of the aptamer (or covalent) complexes to the solid support. Target molecules present in the test sample are detected and/or quantified by detecting the labeling agent on the aptamer (or covalent) complex. The resultant signals can be quantified for target ranges over many orders of magnitude depending on the different serial dilutions of the original sample.

In any of the embodiments disclosed herein, a test sample may be compared to a reference sample. A "reference sample" refers herein to any material, solution, or mixture that contains a plurality of molecules and is known to include at least one target molecule. The precise amount or concentration of any target molecules present in the reference sample may also be known. The term reference sample includes biological samples, as defined herein, and samples that may be used for environmental or toxicology testing, such as contaminated or potentially contaminated water and industrial effluents, for example. A reference sample may also be an end product, intermediate product, or by-product of a preparatory process, for example a manufacturing process. A reference sample may include any suitable assay medium, buffer, or diluent that has been added to a material, solution, or mixture obtained from an organism or from some other source (e.g., the environment or an industrial source).

In one embodiment, aptamers with two different probes are prepared. For example, one aptamer may have a Cy3 dye and the other the Cy5 dye. Using the dual capture crosslinking assay as an example, the reference sample is exposed to one aptamer and the test sample to the other. Each sample is separately treated in an identical manner up to and including the crosslinking step. After crosslinking, the samples can be equally mixed and the remaining steps of the assay may be carried out. A direct comparison of any differential expression (i.e., differential amount or concentration of the target in the samples) between the reference sample and the test sample is possible by measuring the signal from each labeling agent separately. It should be understood that this method can be incorporated into any of the other assays describe herein. Further, in addition to using different dyes, including the use of fluorescent dyes, other labels can be employed to differentiate the signal from each of the different aptamers. For example, in another embodiment, the aptamers used in each of the samples may have different sequence labels. This method is useful, for example, when the readout is Q-PCR or DNA hybridization arrays.

In one embodiment, the reference sample can be a pooled biological sample representing a control group. In another embodiment, the reference sample can be a biological sample obtained from an individual, collected at a first time, and the test sample can be obtained from the same individual but collected at a second time, thereby facilitating a longitudinal study of an individual by measuring and evaluating any changes in the amount or concentration of one or more target molecules in multiple biological samples provided by the individual over time.

Any of the methods described herein may be used to conduct a multiplexed analysis of a test sample. Any such multiplexed analysis can include the use of at least two, at least tens, at least hundreds, or at least thousands of aptamers to simultaneously assay an equal number of target molecules in a test sample, such as a biological sample, for example. In these embodiments, a plurality of aptamers (or labeled photoaptamers, each of which recognizes and optionally croslinks to a different analyte, is introduced to the test sample and any of the above-described assays can be performed. After release of the aptamers, any suitable multiplexed nucleic acid detection methods can be employed to measure the different aptamers that have been released. In one embodiment, this can be accomplished by hybridization to complementary probes that are separately arranged on a solid surface. In another embodiment, each of the different aptamers may be detected based on molecular weight using mass spectroscopy. In yet another embodiment, each of the different aptamers can be detected based on electrophoretic mobility, such as, for example, in capillary electrophoresis, in a gel, or by liquid chromatography. In another embodiment, unique PCR probes can be used to quantify each of the different aptamers using Q-PCR.

In each of the assays disclosed herein, a kinetic challenge is used to increase the specificity of the assay and to reduce non-specific binding. In one embodiment, which can optionally be employed in each of the assays described herein, additional reduction in the non-specific binding may be accomplished by either preincubation of a competitor with the test sample or by addition of a competitor to the mixture during equilibrium binding. In one embodiment, 4 μM of a Z-block competitor oligonucleotide (5'-(ACZZ)$_{28}$AC-3', where Z=5-benzyl-dUTP) is preincubated for about 5 minutes with the test mixture.

Another aspect of the present disclosure relates to kits useful for conveniently performing any of the methods disclosed herein to analyze test samples. To enhance the versatility of the disclosed methods, the reagents can be provided in packaged combination, in the same or separate containers, so that the ratio of the reagents provides for substantial optimization of the method and assay. The reagents may each be in separate containers or various reagents can be combined in one or more containers depending upon the cross-reactivity and stability of the reagents.

A kit comprises, in packaged combination, at least one tagged aptamer and one or more solid supports, each including at least one capture agent. The kit may also include washing solutions such as buffered aqueous medium for sample dilution as well as array washing, sample preparation reagents, and so forth. The kit may further contain reagents useful in introducing a second tag, generally through modification or derivatization of the target. In addition the kit may contain reagents suitable for performing the desired kinetic challenge during the analytical method. The relative amounts of the various reagents in the kits can be varied widely to provide for concentrations of the reagents that substantially optimize the reactions that need to occur during the assay and to further substantially optimize the sensitivity of the assay. Under appropriate circumstances, one or more of the reagents in the kit can be provided as a dry powder, usually lyophilized, including excipients, which upon dissolution will provide a reagent solution having the appropriate concentrations for performing a method or assay in accordance with the present disclosure. The kit can further include a written description of a method in accordance with any of the methods as described herein.

In one embodiment, a kit for the detection and/or quantification of one or more target molecules that may be present in a test sample includes at least one aptamer having specific affinity for a target molecule and comprising a tag; and a solid support, wherein the solid support includes at least one capture agent disposed thereon, and wherein the capture element is capable of associating with the tag on the aptamer.

In another embodiment, a kit for the detection and/or quantification of one or more target molecules that may be present in a test sample includes at least one aptamer having specific affinity for a target molecule and comprising a tag and a label; and a solid support, wherein the solid support includes at least one capture agent disposed thereon, and wherein the capture element is capable of associating with the tag on the aptamer.

In another embodiment, a kit for the detection and/or quantification of one or more target molecules that may be present in a test sample includes at least one aptamer having specific affinity for a target molecule and comprising a releasable tag and a label; and a solid support, wherein the solid support includes at least one capture agent disposed thereon, and wherein the capture element is capable of associating with the tag on the aptamer.

In addition, any of the above-described kits may contain reagents and materials for the performance of a kinetic challenge during the detection method of the kit.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

If present, chemical modifications of a nucleotide can include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylammonium) propyl]carboxyamide)-2'-deoxyuridine chloride, 5-(N-napthylmethylcarboxyamide)-2'-deoxyuridine, 5-(imidazolylethyl)-2'-deoxyuridine, and 5-(N-[1-(2,3-dihydroxypropyl)]carboxyamide)-2'-deoxyuridine), 8-position purine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine, and the like.

Figure 16:
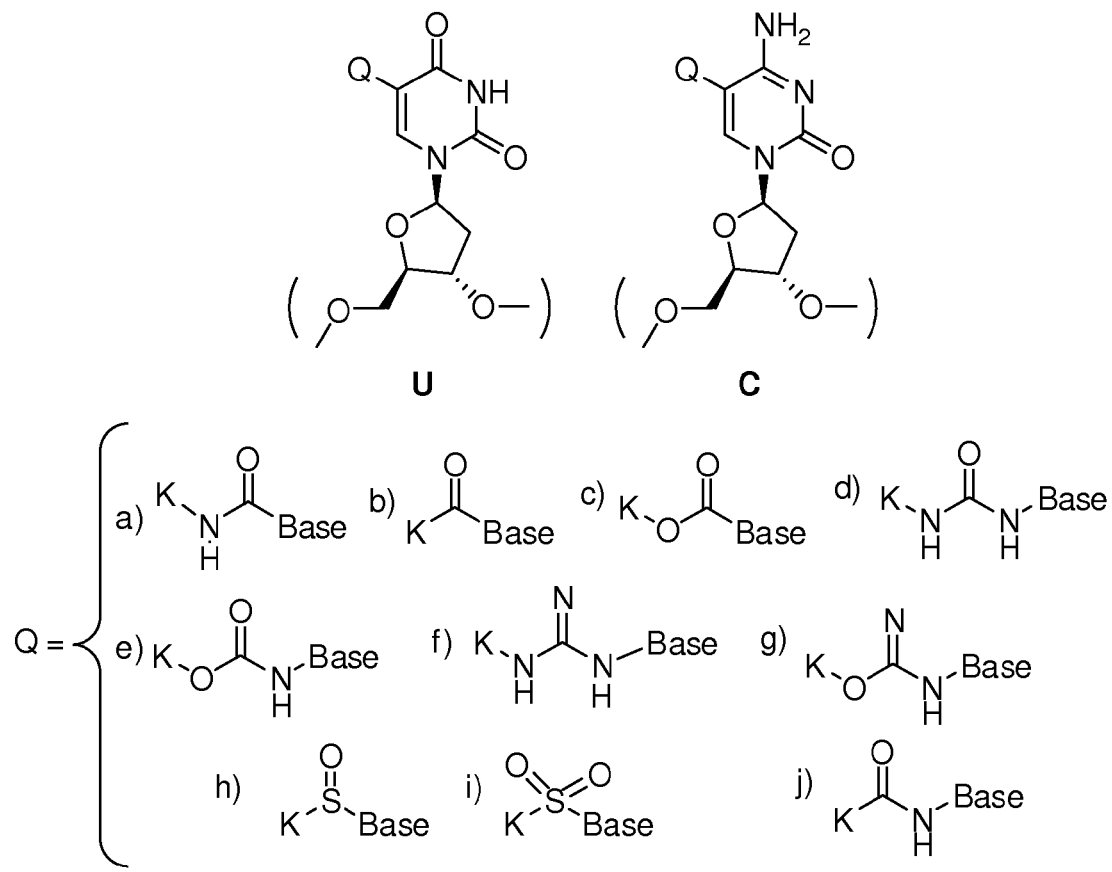
FIG. 16 exhibits the base modifications of nucleotides discussed in this disclosure. The R groups that may be used are described in addition to the linkers (X) that may be used between the nucleotide attachment point and the R group is shown. The positions of attachment for the various "R" groups are also indicated on the respective R groups.
Figure 16:
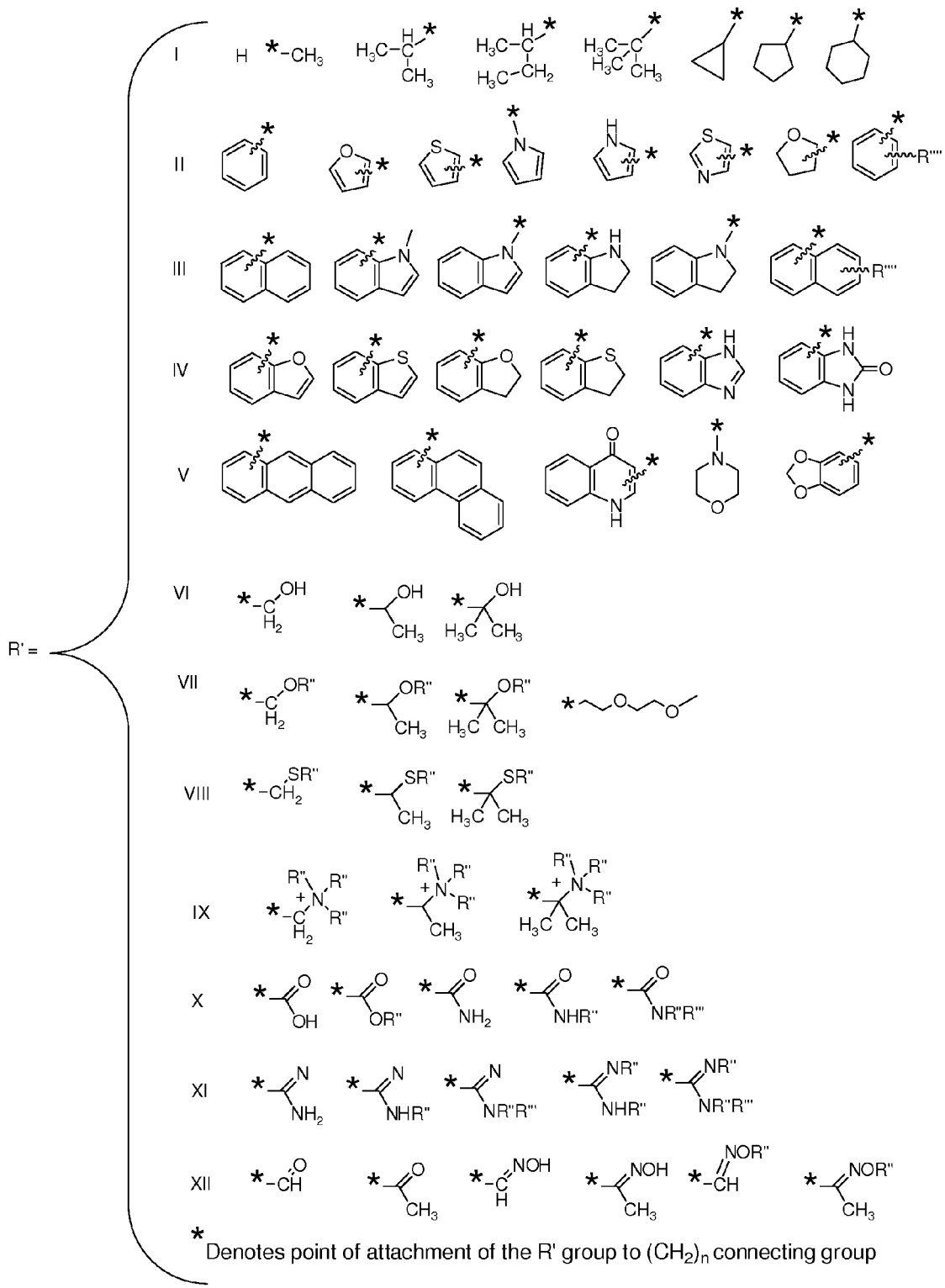

In one embodiment, the term "C-5 modified pyrimidine" refers to a pyrimidine with a modification at the C-5 position including, but not limited to those moieties illustrated in FIG. 16. Examples of a C-5 modified pyrimidine include those described in U.S. Pat. Nos. 5,719,273 and 5,945,527. Examples of a C-5 modification include substitution of deoxyuridine at the C-5 position with a substituent selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

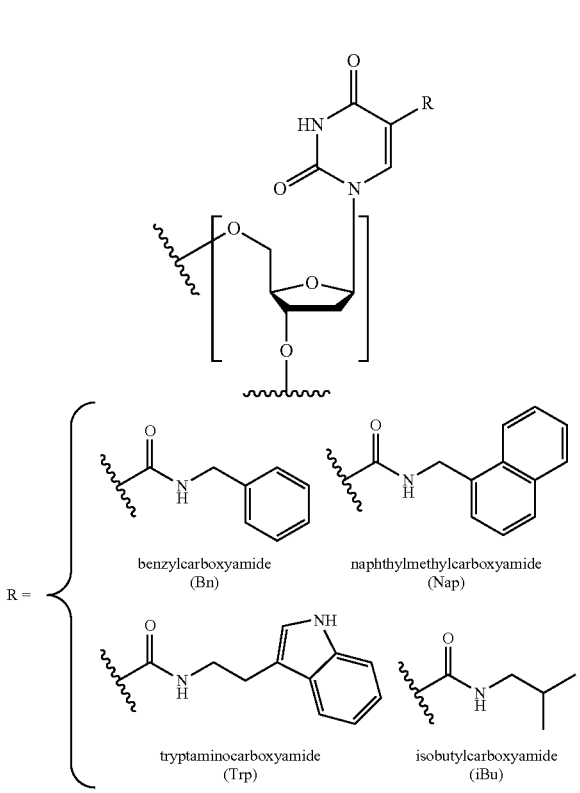

As delineated above, representative C-5 modified pyrimidines include: 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-napthylmethylcarboxyamide)-2'-deoxyuridine (NapdU).

Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by any suitable protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

In one embodiment, aptamer constructs can include one or more C5-modified nucleotides in the variable region of the aptamer that effectively slows the rate of dissociation of the aptamer from its target. The base modifications of the nucleotides used in the production of the variable region of the aptamer have been shown to produce aptamers that have very slow off-rates from their respective targets. For example, there is evidence that an aptamer containing 5 position modified pyrimidines, such as any of those illustrated in FIG. 16, has slow dissociation rate from its target. In some embodiments, the use of an aptamer that includes nucleotides that have been modified in this manner in an assay method that includes a kinetic challenge yields enhanced sensitivity and specificity in the detection of a target. As indicated in FIG. 4, aptamers for over 500 targets have been produced to date. Many of these aptamers have slow-off rate characteristics.

In one embodiment, the variable region of the aptamer includes nucleotides that have modified bases. These aptamers may be used in any of the methods, devices, and kits described herein. There is evidence that these modified nucleotides may lead to the identification of aptamers that have very slow off-rates from their respective target while maintaining high affinity to the target. In one embodiment, the C-5 position of the pyrimidine bases may be modified. In other embodiments, some or all of the pyrimidines in the aptamer may be the base modified nucleotides. In yet other embodiments, combinations of modified pyrimidines may be used. Aptamers containing nucleotides with modified bases have a number of properties that are different than aptamers containing only unmodified nucleotides (i.e., naturally occurring nucleotides). In one embodiment, the method for modification of the nucleotides is through a carboxyamide linkage. However other methods for modification may be suitable. It has been surprisingly observed that the structure of the identified slow off-rate aptamers do not appear to conform to the structures predicted by the base pairing models. This is supported by the fact that the measured melting temperatures of the aptamers are not what the models may predict. As shown herein, there appears to be little or no correlation between the measured and predicted melting temperatures. Furthermore, on average, the calculated Tm is 6° C. lower than the measured Tm. The measured melting temperatures indicate that aptamers that include these modified nucleotides are more stable than may be predicted and potentially possess novel secondary structures. Identification of slow off-rate aptamers are more likely when modified nucleotides are used in the production of the initial library or candidate mixture.

As used herein, "modified nucleic acid" refers to a nucleic acid sequence containing one or more modified nucleotides that are compatible with the SELEX process.

In another embodiment of the present disclosure a non-covalent complex of an aptamer and a target is provided, wherein the aptamer has a $K_d$ for the target of about 100 nM or less, wherein the rate of dissociation ($t_{1/2}$) of the aptamer from the target is greater than or equal to about 30 minutes; is between about 30 minutes and about 240 minutes; is ≥ about 30 minutes, ≥ about 60 minutes, ≥ about 90 minutes, ≥ about 120 minutes, ≥ about 150 minutes, ≥ about 180 minutes, ≥ about 210 minutes, ≥ about 240 minutes; and/or wherein one, several or all pyrimidines in the nucleic acid sequence of the aptamer are modified at the 5-position of the base. The modifications may be selected from the group of compounds shown in FIG. 16. Aptamers may be designed with any combination of the base modified nucleotides desired.

As used herein, "aptamer" and "nucleic acid ligand" are used interchangeably to refer to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides. "Aptamers" refer to more than one such set of molecules. Different aptamers may have either the same or different numbers of nucleotides. Any of the methods disclosed herein may include the use of one or more aptamers. Any of the methods disclosed herein may also include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers may have either the same tag or a different tag. Aptamers may be ssDNA, dsDNA, RNA or a combination of DNA and RNA.

An aptamer can be identified using any known method, including the SELEX process. See, e.g., U.S. Pat. No. 5,475,096 entitled "Nucleic Acid Ligands". Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. See, e.g., U.S. Pat. No. 5,475,096 entitled "Nucleic Acid Ligands". The SELEX process may be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment ChemiSELEX". The SELEX process may also be used to generate aptamers with improved off-rates as described in U.S. application Ser. No. 12/175,434 entitled "Method for Generating Aptamers with Improved Off-Rates", which is being filed concurrently with the instant application and which is incorporated herein by reference in its entirety.

As used herein, the term "aptamer affinity complex" or "aptamer complex" refers to a non-covalent complex that is formed by the interaction of an aptamer with its target molecule. An "aptamer affinity complex" or "aptamer complex" is a set of copies of one type or species of complex formed by an aptamer bound to its corresponding target molecule. "Aptamer affinity complexes" or "aptamer complexes" refer to more than one such set of complexes. An aptamer affinity complex or aptamer complex can generally be reversed or dissociated by a change in an environmental condition, e.g., an increase in temperature, an increase in salt concentration, or an addition of a denaturant.

As used herein, "non-specific complex" refers to a non-covalent association between two or more molecules other than an aptamer and its target molecule. Because a non-specific complex is not selected on the basis of an affinity interaction between its constituent molecules, but represents an interaction between classes of molecules, molecules associated in a non-specific complex will exhibit, on average, much lower affinities for each other and will have a correspondingly higher dissociation rate than an aptamer and its target molecule. Non-specific complexes include complexes formed between an aptamer and a non-target molecule, a competitor and a non-target molecule, a competitor and a target molecule, and a target molecule and a non-target molecule.

The SELEX process generally begins with the preparation of a candidate mixture of nucleic acids of differing sequence. The candidate mixture generally includes nucleic acid sequences that include two fixed regions (i.e., each of the members of the candidate mixture contains the same sequences in the same location) and a variable region. Typically, the fixed sequence regions are selected such that they assist in the amplification steps described below, or enhance the potential of a given structural arrangement of the nucleic acids in the candidate mixture. The variable region typically provides the target binding region of each nucleic acid in the candidate mixture, and this variable region can be completely randomized (i.e., the probability of finding a base at any position being one in four) or only partially randomized (e.g., the probability of finding a base at any location can be selected at any level between 0 and 100 percent). The prepared candidate mixture is contacted with the selected target under conditions that are favorable for binding to occur between the target and members of the candidate mixture. Under these conditions, the interaction between the target and the nucleic acids of the candidate mixture generally forms nucleic acid-target pairs that have the strongest relative affinity between members of the pair. The nucleic acids with the highest affinity for the target are partitioned from those nucleic acids with lesser affinity to the target. The partitioning process is conducted in a manner that retains the maximum number of high affinity candidates. Those nucleic acids selected during partitioning as having a relatively high affinity to the target are amplified to create a new candidate mixture that is enriched in nucleic acids having a relatively high affinity for the target. By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a very small number of unique nucleic acids representing those nucleic acids from the original candidate mixture that have the highest affinity to the target molecule.

As used herein, "photoaptamer," "photoreactive nucleic acid ligand," and "photoreactive aptamer" are used interchangeably to refer to an aptamer that contains one or more photoreactive functional groups that can covalently bind to or "crosslink" with a target molecule. For example, a naturally occurring nucleic acid residue may be modified to include a chemical functional group that confers photoreactivity upon the nucleic acid residue upon exposure to a radiation source of an appropriate wavelength. A photoaptamer can be identified and/or prepared using any known method. In some embodiments, a photoreactive aptamer is identified using the photoSELEX process. See, e.g., U.S. Pat. No. 5,763,177, U.S. Pat. No. 6,001,577, and U.S. Pat. No. 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands" and U.S. application Ser. No. 12/175,388, entitled "Improved SELEX and PHOTOSELEX", which is being filed concurrently with the instant application and which is incorporated herein by reference in its entirety.

Exemplary photoreactive functional groups that may be incorporated into a photoaptamer include 5-bromouracil, 5-iodouracil, 5-bromovinyluracil, 5-iodovinyluracil, 5-azidouracil, 4-thiouracil, 5-thiouracil, 4-thiocytosine, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-aziodoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

In addition to these exemplary nucleoside-based photoreactive functional groups, other photoreactive functional groups that can be added to a terminal end of an aptamer through an appropriate linker molecule can be used. Such photoreactive functional groups include benzophenone, anthraquinone, 4-azido-2-nitro-aniline, psoralen, derivatives of any of these, and the like.

A photoreactive functional group incorporated into a photoaptamer may be activated by any suitable method. In one embodiment, a photoaptamer containing a photoreactive functional group is crosslinked to its target by exposing the photoaptamer affinity complex to a source of electromagnetic radiation. Suitable types of electromagnetic radiation include ultraviolet light, visible light, X-rays, and gamma rays. Suitable radiation sources include sources that utilize either monochromatic light or filtered polychromatic light.

As used herein, the term "aptamer covalent complex" refers to an aptamer affinity complex in which the aptamer has been induced to form or otherwise forms a covalent bond with its target molecule. An "aptamer covalent complex" is a set of copies of one type or species of complex formed by an aptamer covalently bound to its corresponding target molecule. "Aptamer covalent complexes" refer to more than one such set of complexes. A covalent bond or linkage between an aptamer and its target molecule can be induced by photoactivation of a chemical moiety on the aptamer, including those moieties described above with respect to photoaptamers. A covalent bond or linkage between an aptamer and its target molecule can also be induced chemically. Chemical groups that can be included in an aptamer and used to induce a covalent linkage with the target include but are not limited to aldehydes, maleimides, acrylyl derivatives, diazonium derivatives, thiols, etc. In some embodiments, chemical crosslinking groups, such as maleimide or diazonium salts, for example, can convert aptamer affinity complexes to aptamer covalent complexes simply by providing the proper environment and juxtaposition of reactive groups required for specific and sufficiently enhanced chemical reactivity to occur. In other embodiments, chemical crosslinkers, such as aldehyde groups, may require the addition of another component, for example, sodium cyanoborohydride, to convert aptamer affinity complexes to stable, irreversible aptamer covalent complexes. In yet other embodiments, no such chemical crosslinkers are included in an aptamer; rather, a third reagent is used to convert an aptamer affinity complex to an aptamer covalent complex by facilitating a covalent attachment between the aptamer and its target. For example, a homo- or hetero-bifunctional reagent containing both an amine reactive moiety (e.g., an N-hydroxy succinimidyl ester, an aldehyde, or an imidate) and a nucleoside-reactive group (e.g., an iodoacetamide or an activated aldehyde) can induce covalent complexation of an aptamer affinity complex, such as an affinity complex formed by an aptamer and a target protein.

Photoaptamers can be identified by first identifying an affinity aptamer and substituting in one or more photoreactive nucleotide residues. Alternatively, photoaptamers can be identified by a SELEX process comprising the following: (a) preparing a candidate mixture of nucleic acids, wherein each nucleic acid comprises (i) at least one non-photoreactive placeholding pyrimidine and (ii) at least one modified pyrimidine; (b) contacting the candidate mixture with a target, wherein nucleic acids having an increased affinity to the target relative to the candidate mixture may be partitioned from the remainder of the candidate mixture; (c) partitioning the increased affinity nucleic acids from the remainder of the candidate mixture; (d) amplifying the increased affinity nucleic acids to yield a nucleic acid ligand-enriched mixture of nucleic acids, whereby an aptamer to the target compound may be identified; (e) repeating (b)-(d) as desired; (f) producing a candidate photoaptamer by replacing in each nucleic acid of the nucleic acid ligand-enriched mixture of (d) one or more non-photoreactive placeholding pyrimidines with a photoreactive pyrimidine; (g) contacting the candidate photoaptamer with the target wherein a candidate photoaptamer-target complex is formed; (h) irradiating said candidate photoaptamer-target complex; (i) determining whether said candidate photoaptamer-target complex has photocrosslinked; (j) repeating (f)-(i) as desired; and (k) identifying at least one photoaptamer to the target.

The term "test sample" refers herein to any material, solution, or mixture that contains a plurality of molecules and may include at least one target molecule. The term test sample includes biological samples, as defined below, and samples that may be used for environmental or toxicology testing, such as contaminated or potentially contaminated water and industrial effluents, for example. A test sample may also be an end product, intermediate product, or by-product of a preparatory process, for example a manufacturing process. A test sample may include any suitable assay medium, buffer, or diluent that has been added to a material, solution, or mixture obtained from an organism or from some other source (e.g., the environment or an industrial source).

The term "biological sample" refers to any material, solution, or mixture obtained from an organism. This includes blood (including whole blood, leukocytes, peripheral blood mononuclear cells, plasma, and serum), sputum, breath, urine, semen, saliva, meningeal fluid, amniotic fluid, glandular fluid, lymph fluid, nipple aspirate, bronchial aspirate, synovial fluid, joint aspirate, cells, a cellular extract, and cerebrospinal fluid. This also includes experimentally separated fractions of all of the preceding. The term "biological sample" also includes materials, solutions, or mixtures containing homogenized solid material, such as from a stool sample, a tissue sample, or a tissue biopsy, for example. The term "biological sample" also includes materials, solutions, or mixtures derived from a tissue culture, cell culture, bacterial culture, or viral culture.

As used herein, "target molecule" and "target" are used interchangeably to refer to any molecule of interest to which an aptamer can bind with high affinity and specificity and that may be present in a test sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component that does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing. An aptamer may be identified for virtually any chemical or biological molecule of any size, and thus virtually any chemical or biological molecule of any size can be a suitable target. A target can also be modified to enhance the likelihood or strength of an interaction between the target and the aptamer. A target can also be modified to include a tag, as defined above. In exemplary embodiments, the target molecule is a protein. See U.S. Pat. No. 6,376,190 entitled "Modified SELEX Processes Without Purified Protein" for methods in which the SELEX target is a peptide.

"Polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains.

As used herein, "non-target molecule" and "non-target" are used interchangeably to refer to a molecule contained in a test sample that can form a non-specific complex with an aptamer. A "non-target molecule" or "non-target" is a set of copies of one type or species of molecule or multi-molecular structure that is capable of binding to an aptamer. "Non-target molecules" or "non-targets" refer to more than one such set of molecules. It will be appreciated that a molecule that is a non-target for a first aptamer may be a target for a second aptamer. Likewise, a molecule that is a target for the first aptamer may be a non-target for the second aptamer.

As used herein, the term "partition" refers to a separation or removal of one or more molecular species from the test sample. Partitioning can be used to increase sensitivity and/or reduce background. Partitioning is most effective following aptamer complex formation or when the aptamer affinity complex becomes irreversible due to the covalent bond introduced during crosslinking. A partitioning step may be introduced after any step, or after every step, where the aptamer affinity complex is immobilized. Partitioning may also rely on a size differential or other specific property that differentially exists between the aptamer affinity complex and other components of the test sample. Partitioning may also be achieved through a specific interaction with an aptamer or target. Partitioning maybe also be accomplished based on the physical or biochemical properties of the aptamer, target, aptamer affinity complex or aptamer covalent complex As used herein "Catch 1" refers to the partitioning of an aptamer affinity complex or aptamer covalent complex based on the capture of the aptamer. The purpose of Catch 1 is to remove substantially all of the components in the test sample that are not associated with the aptamer. Removing the majority of such components will generally improve target tagging efficiency by removing non-target molecules from the target tagging step used for Catch 2 capture and may lead to lower assay background. In one embodiment, a tag is attached to the aptamer either before the assay, during preparation of the assay, or during the assay by appending the tag to the aptamer. In one embodiment, the tag is a releasable tag. In one embodiment, the releasable tag comprises a cleavable linker and a tag. As described above, tagged aptamer can be captured on a solid support where the solid support comprises a capture element appropriate for the tag. The solid support can then be washed to remove any materials in the test mixture that are not associated with the aptamer.

In various embodiments, aptamer affinity (or covalent) complexes are captured or immobilized on the solid support using the capture tag incorporated into the aptamer (aptamer tag). For example, if the capture tag on the aptamer is biotin, as described above, beads having avidin, streptavidin, neutravidin, Extravidin, and like on the surface can be used to capture the aptamer affinity (or covalent) complexes. The beads are washed to remove any free (uncomplexed) target and other sample matrix components.

In another embodiment, the tag is a hybridization tag complementary to a probe immobilized on the first solid support. The solid support in this case may include microbeads (for example, paramagnetic beads), any other suitable solid supports described herein, and the like. The hybridization tag may be a unique sequence tag added to the aptamer or it may be a portion of the aptamer sequence or it may be the entire aptamer sequence. After the aptamer is associated with the solid support through hybridization, the test sample can be washed to remove any materials that are not associated with the aptamer. In one embodiment, the aptamer covalent complexes and free aptamer can be released from the solid support using any suitable method to reverse hybridization, such as high salt, low or high pH, high temperature or a combination of any of these. Release of a hybridization tag in Catch 1 is generally not compatible with preserving aptamer affinity complexes, since the conditions that lead to disruption of tag-probe hybridization will generally lead to denaturation of the aptamer's structure, resulting in the dissociation of the aptamer affinity complex.

In another embodiment, the removal of components not associated with the aptamer can be accomplished using physical techniques rather than an explicit aptamer tag and a first solid support. In one embodiment, this is accomplished by precipitating the aptamer, both free and complexed, from the test sample, leaving other molecules that can react with the target tagging agent in the supernatant to be discarded. Note that this method is designed for use with the photocrosslinking assays. Such nucleic acid precipitation can be accomplished with reagents that include cetyltrimethylammonium bromide (CTAB), dodecyltrimethylammonium bromide (DTAB), and organic solvents such as ethanol, for example.

As used herein "Catch 2" refers to the partitioning of an aptamer affinity complex or aptamer covalent complex based on the capture of the target molecule. The purpose of the Catch 2 step is to remove free, or uncomplexed, aptamer from the test sample prior to detection and optional quantification. Removing free aptamer from the sample allows for the detection of the aptamer affinity or aptamer covalent complexes by any suitable nucleic acid detection technique. When using Q-PCR for detection and optional quantification, the removal of free aptamer is needed for accurate detection and quantification of the target molecule.

In one embodiment, the target molecule is a protein or peptide and free aptamer is partitioned from the aptamer affinity (or covalent) complex (and the rest of the test sample) using reagents that can be incorporated into proteins (and peptides) and complexes that include proteins (or peptides), such as, for example, an aptamer affinity (or covalent) complex. The tagged protein (or peptide) and aptamer affinity (or covalent) complex can be immobilized on a solid support, enabling partitioning of the protein (or peptide) and the aptamer affinity (or covalent) complex from free aptamer. Such tagging can include, for example, a biotin moiety that can be incorporated into the protein or peptide.

In one embodiment, a Catch 2 tag is attached to the protein (or peptide) either before the assay, during preparation of the assay, or during the assay by chemically attaching the tag to the targets. In one embodiment the Catch 2 tag is a releasable tag. In one embodiment, the releasable tag comprises a cleavable linker and a tag. It is generally not necessary, however, to release the protein (or peptide) from the Catch 2 solid support. As described above, tagged targets can be captured on a second solid support where the solid support comprises a capture element appropriate for the target tag. The solid support can then be washed to remove free aptamer from the solution.

In one embodiment, the target tag introduced for Catch 2 is the same tag as that on the aptamer used for Catch 1. In this embodiment, the target tagging is performed after the Catch 1 step and prior to introduction of the Catch 2 solid support. In one embodiment, sites not occupied with aptamers on the Catch 1 support can be blocked prior to tagging targets if target tagging is done while on the Catch 1 support.

In another embodiment, the aptamer affinity complex or the aptamer covalent complex can be captured on the second solid support directly through association with a capture reagent on the second solid support. No explicit target tagging is necessary in this embodiment. In one embodiment, the second solid support contains an antibody that binds the target molecule. In another embodiment, the support contains an Fc fragment that binds the target molecule. In another embodiment, when the target molecule is IgG, IgM, IgA or IgE, the support may contain Protein A to bind the target protein. Any capture reagent that binds to the target molecule in an aptamer affinity or aptamer covalent complex can be used for the Catch 2 step.

In another embodiment, the removal of free aptamer can be accomplished using physical techniques rather than an explicit target tag and a second solid support. In one embodiment where the target molecule is a protein or peptide, this is accomplished by precipitating the aptamer covalent complexes and leaving free aptamer in the supernatant to be discarded [note that this works only for covalent complexes]. Such protein or peptide precipitation can be accomplished with SDS and high salt, usually $K^+$, for example. After SDS-$K^+$ precipitation, the aptamer covalent complex can be recovered for quantification.

After removal of free aptamer by washing the second solid support, the aptamer affinity complexes are then subject to a dissociation step in which the complexes are disrupted to yield free aptamer while the target molecules generally remain bound to the solid support through the binding interaction of the probe and target capture tag. The aptamer from the aptamer affinity complex can be released by any method that disrupts the structure of either the aptamer or the target. This may be achieved though washing of the support bound aptamer affinity complexes in high salt buffer which dissociates the non-covalently bound aptamer-target complexes. Eluted free aptamers are collected and detected. In another embodiment, high or low pH is used to disrupt the aptamer affinity complexes. In another embodiment high temperature is used to dissociate aptamer affinity complexes. In another embodiment, a combination of any of the above methods may be used.

In the case of aptamer covalent complexes, release of the aptamer for subsequent quantification is accomplished using a cleavable linker in the aptamer construct. In another embodiment, a cleavable linker in the target tag will result in the release of the aptamer covalent complex.

As used herein, "competitor molecule" and "competitor" are used interchangeably to refer to any molecule that can form a non-specific complex with a non-target molecule, for example to prevent that non-target molecule form rebinding non-specifically to an aptamer. A "competitor molecule" or "competitor" is a set of copies of one type or species of molecule. "Competitor molecules" or "competitors" refer to more than one such set of molecules. Competitor molecules include oligonucleotides, polyanions (e.g., heparin, herring sperm DNA, single-stranded salmon sperm DNA, and polydextrans (e.g., dextran sulfate)), abasic phosphodiester polymers, dNTPs, and pyrophosphate. In the case of a kinetic challenge that uses a competitor, the competitor can also be any molecule that can form a non-specific complex with a free aptamer, for example to prevent that aptamer from rebinding non-specifically to a non-target molecule. Such competitor molecules include polycations (e.g., spermine, spermidine, polylysine, and polyarginine) and amino acids (e.g., arginine and lysine). When a competitor is used as the kinetic challenge a fairly high concentration is utilized relative to the anticipated concentration of total protein or total aptamer present in the sample. In one embodiment, about 10 mM dextran sulfates is used as the competitor in a kinetic challenge. In one embodiment, the kinetic challenge comprises adding a competitor to the mixture containing the aptamer affinity complex, and incubating the mixture containing the aptamer affinity complex for a time of greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises adding a competitor to the mixture containing the aptamer affinity complex and incubating the mixture containing the aptamer affinity complex for a time such that the ratio of the measured level of aptamer affinity complex to the measured level of the non-specific complex is increased.

In some embodiments, the kinetic challenge is performed by diluting the test sample with binding buffer or any other solution that does not significantly increase the natural rate of dissociation of aptamer affinity complexes. The dilution can be about 2×, about 3×, about 4×, about 5×, or any suitable greater dilution. Larger dilutions provide a more effective kinetic challenge by reducing the concentration of total protein and aptamer after dilution and, therefore, the rate of their re-association. If dilution is used to introduce a kinetic challenge, the subsequent test sample mixture containing the aptamer affinity complex may be concentrated before further processing. If applicable, this concentration can be accomplished using methods described herein with respect to the optional partitioning of any free aptamers from the test sample and/or the optional removal of other components of the test sample that can react with the tagging agent. When dilution is used as the kinetic challenge, the amount of dilution is selected to be as high as practical, in view of both the initial test sample volume and the desirability of recovering the aptamer affinity complex from the final (diluted) volume without incurring a significant loss of the complex. In one embodiment, the aptamer affinity complex is diluted and the mixture is incubated for a time ≥ about 30 seconds, ≥ about 1 minute, ≥ about 2 minutes, ≥ about 3 minutes, ≥ about 4 minutes, ≥ about 5 minutes, ≥ about 10 minutes, ≥ about 30 minutes, and ≥ about 60 minutes. In another embodiment, the aptamer affinity complex is diluted and the mixtures containing the aptamer affinity complex are incubated for a time such that the ratio of the measured level of aptamer affinity complex to the measured level of the non-specific complex is increased.

In some embodiments, the kinetic challenge is performed in such a manner that the effect of sample dilution and the effect of introducing a competitor are realized simultaneously. For example, a test sample can be diluted with a large volume of competitor. Combining these two kinetic challenge strategies may provide a more effective kinetic challenge than can be achieved using one strategy. In one embodiment, the dilution can be about 2×, about 3×, about 4×, about 5×, or any suitable greater dilution and the competitor is about 10 mM dextran sulfate. In one embodiment, the kinetic challenge comprises diluting the mixture containing the aptamer affinity complex, adding a competitor to the mixture containing the aptamer affinity complex, and incubating the mixture containing the aptamer affinity complex for a time greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises diluting the mixture containing the aptamer affinity complex, adding a competitor to the mixture containing the aptamer affinity complex and incubating the mixture containing the aptamer affinity complex for a time such that the ratio of the measured level of aptamer affinity complex to the measured level of the non-specific complex is increased.

In various embodiments, aptamer affinity (or covalent) complexes are captured or immobilized on the solid support using a tag incorporated into the aptamer (aptamer tag), or attached to the target. For example, if the tag on the aptamer is biotin, beads having a capture element such as avidin, streptavidin, neutravidin, Extravidin, and like on the surface can be used to capture the aptamer affinity (or covalent) complexes. The beads are washed to remove any free (uncomplexed) target.

As disclosed herein, an aptamer can further comprise a "tag," which refers to a component that provides a means for attaching or immobilizing an aptamer (and any target molecule that is bound to it) to a solid support. A "tag" is a set of copies of one type or species of component that is capable of associating with a "capture element". "Tags" or "capture elements" refers to more than one such set of components. The tag can be attached to or included in the aptamer by any suitable method. Generally, the tag allows the aptamer to associate, either directly or indirectly, with a capture element or receptor that is attached to the solid support. The capture element is typically chosen (or designed) to be highly specific in its interaction with the tag and to retain that association during subsequent processing steps or procedures. A tag can enable the localization of an aptamer affinity complex (or covalent aptamer affinity complex) to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, polyhistidine, or any fragment or derivative of these structures, any combination of the foregoing, or any other structure with which a capture element (or linker molecule, as described below) can be designed or configured to bind or otherwise associate with specificity. Generally, a tag is configured such that it does not interact intramolecularly with either itself or the aptamer to which it is attached or of which it is a part. If SELEX is used to identify an aptamer, the tag may be added to the aptamer either pre- or post-SELEX. In one embodiment, the tag is included on the 5'-end of the aptamer post-SELEX. In another embodiment, the tag is included on the 3'-end of the aptamer post-SELEX. In yet another embodiment, tags may be included on both the 3' and 5' ends of the aptamers in a post-SELEX modification process. In another embodiment, the tag may be an internal segment of the aptamer.

In one embodiment, the tag is a biotin group and the capture element is a biotin binding protein such as avidin, streptavidin, neutravidin, Extravidin. This combination is may be conveniently used in various embodiments, as biotin is easily incorporated into aptamers during synthesis and streptavidin beads are readily available.

In one embodiment, the tag is polyhistidine and the capture element is nitrilotriacetic acid (NTA) chelated with a metal ion such as nickel, cobalt, iron, or any other metal ion able to form a coordination compound with poly-histidine when chelated with NTA.

In one embodiment, the tag is a polynucleotide that is designed to hybridize directly with a capture element that contains a complementary polynucleotide sequence. In this case, the tag is sometimes referred to as a "sequence tag" and the capture element is generally referred to as a "probe". In this embodiment, the tag is generally configured and the hybridization reaction is carried out under conditions such that the tag does not hybridize with a probe other than the probe for which the tag is a perfect complement. This allows for the design of a multiplex assay format as each tag/probe combination can have unique sequences.

In some embodiments, the tag comprises nucleotides that are a part of the aptamer itself. For example, if SELEX is used to identify an aptamer, the aptamer generally includes a 5'-fixed end separated from a 3'-fixed end by a nucleotide sequence that varies, depending upon the aptamer, that is, a variable region. In one embodiment, the tag can comprise any suitable number of nucleotides included in a fixed end of the aptamer, such as, for example, an entire fixed end or any portion of a fixed end, including nucleotides that are internal to a fixed end. In another embodiment, the tag can comprise any suitable number of nucleotides included within the variable region of the aptamer, such as, for example, the entire variable region or any portion of the variable region. In a further embodiment, the tag can comprise any suitable number of nucleotides that overlap both the variable region and one of the fixed ends, that is, the tag can comprise a nucleotide sequence that includes any portion (including all) of the variable region and any portion (including all) of a fixed end.

In another embodiment, a tag can associate directly with a probe and covalently bind to the probe, thereby covalently linking the aptamer to the surface of the solid support. In this embodiment, the tag and the probe can include suitable reactive groups that, upon association of the tag with the probe, are sufficiently proximate to each other to undergo a chemical reaction that produces a covalent bond. The reaction may occur spontaneously or may require activation, such as, for example, photo-activation or chemical activation. In one embodiment, the tag includes a diene moiety and the probe includes a dienophile, and covalent bond formation results from a spontaneous Diels-Alder conjugation reaction of the diene and dienophile. Any appropriate complementary chemistry can be used, such as, for example, N-Mannich reaction, disulfide formation, Curtius reaction, Aldol condensation, Schiff base formation, and Michael addition.

In another embodiment, the tag associates indirectly with a probe, such as, for example, through a linker molecule, as further described below. In this embodiment, the tag can include a polynucleotide sequence that is complementary to a particular region or component of a linker molecule. The tag is generally configured and the hybridization reaction is carried out such that the tag does not hybridize with a polynucleotide sequence other than the polynucleotide sequence included in the linker molecule.

If the tag includes a polynucleotide, the polynucleotide can include any suitable number of nucleotides. In one embodiment, a tag includes at least about 10 nucleotides. In another embodiment, the tag includes from about 10 to about 45 nucleotides. In yet another embodiment, the tag includes at least about 30 nucleotides. Different tags that include a polynucleotide can include either the same number of nucleotides or a different number of nucleotides.

In some embodiments, the tag component is bi-functional in that it includes functionality for specific interaction with a capture element on a solid support or "probe" as defined below (probe association component), and functionality for dissociating the molecule to which it is attached from the probe association component of the tag. The means for dissociating the probe association component of the tag includes chemical means, photochemical means or other means depending upon the particular tag that is employed.

In some embodiments, the tag is attached to the aptamer. In other embodiments, the tag is attached to the target molecule. The tag may be attached to the target molecule prior to the aptamer binding step, or may be attached to the target molecule or aptamer affinity (or covalent) complex after binding equilibration (or photo-crosslinking) has been achieved.

As used herein, "capture element", "probe" or "receptor" refers to a molecule that is configured to associate, either directly or indirectly, with a tag. A "capture element", "probe" or "receptor" is a set of copies of one type of molecule or one type of multi-molecular structure that is capable of immobilizing the moiety to which the tag is attached to a solid support by associating, either directly or indirectly, with the tag. "Capture elements" "probes" or "receptors" refer to more than one such set of molecules. A capture element, probe or receptor can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, polyhistidine, or any fragment or derivative of these structures, any combination of the foregoing, or any other structure with which a tag (or linker molecule) can be designed or configured to bind or otherwise associate with specificity. A capture element, probe or receptor can be attached to a solid support either covalently or non-covalently by any suitable method.

While the terms "capture element", "probe" and "receptor" are used interchangeably, probe generally refers to a polynucleotide sequence. In one embodiment, the probe includes a polynucleotide that has a sequence that is complementary to a polynucleotide tag sequence. In this embodiment, the probe sequence is generally configured and the hybridization reaction is carried out under conditions such that the probe does not hybridize with a nucleotide sequence other than the tag for which the probe includes the complementary sequence (i.e., the probe is generally configured and the hybridization reaction is carried out under conditions such that the probe does not hybridize with a different tag or an aptamer).

In another embodiment, the probe associates indirectly with a tag, for example, through a linker molecule. In this embodiment, the probe can include a polynucleotide sequence that is complementary to a particular region or component of a linker molecule. The probe is generally configured and the hybridization reaction is carried out such that the probe does not hybridize with a polynucleotide sequence other than the polynucleotide sequence included in the linker molecule.

If a probe includes a polynucleotide, the polynucleotide can include any suitable number of nucleotides. In one embodiment, a probe includes at least about 10 nucleotides. In another embodiment, a probe includes from about 10 to about 45 nucleotides. In yet another embodiment, a probe includes at least about 30 nucleotides. Different probes that include a polynucleotide can include either the same number of nucleotides or a different number of nucleotides.

In some embodiments, the capture probe is bi-functional in that it includes functionality for specific interaction with a polynucleotide tag, and functionality for dissociating the probe from the solid support such that the probe and aptamer are simultaneously released. The means for dissociating the probe from the solid support includes chemical means, photochemical means or other means depending upon the particular capture probe that is employed.

Due to the reciprocal nature of the interaction between a particular tag and capture element pair, a tag in one embodiment may be used as a capture element in another embodiment, and a capture element in one embodiment may be used as a tag in another embodiment. For example, an aptamer with a biotin tag may be captured with streptavidin attached to a solid support in one embodiment, while an aptamer with a streptavidin tag may be captured with biotin attached to a solid support in another embodiment.

In some embodiments, it is desirable to immobilize aptamer affinity (or covalent) complexes to a solid support to enable the isolation of aptamer affinity (or covalent) complexes and remove free aptamer. In one embodiment, the tag is added to the target molecule of the affinity (or covalent) complex using a reagent that is highly reactive with the target molecule and weakly reactive (or ideally non-reactive) with the aptamer. In this embodiment, the tag is designed such that target tagging of aptamer affinity complexes is accomplished with little or no dissociation of the affinity complex, for example, at a pH and ionic strength that is compatible with the affinity interaction and does not change the conformation of the target or the aptamer, and a degree of tagging that does not introduce a large plurality of tags on each target molecule such that interaction with the aptamer is affected. Target tagging of aptamer covalent complexes does not share these restrictions and can be accomplished under any conditions suitable for efficient tagging.

In some embodiments, it may be important to assure that the tagging reagent tags most, if not all, proteins present in a test sample but tends not to tag, or tags only minimally, nucleic acids or other components of the assay, such as the solid support. Any reactive chemical group found on proteins, but not found on nucleic acids or the substrate surface, can serve as a site of covalent attachment. Exemplary reactive chemical groups include primary amines (e.g., on lysine residues), thiols (e.g., on cysteine, which may be produced by the reduction of disulfide linkages), alcohols (e.g., on serine, threonine, tyrosine, and sugar moieties on glycoproteins (including the products of oxidation of cis-diols on such sugars)), and carboxylates (e.g., on glutamic and aspartic acid). In one embodiment, the tagging reagent comprises an N-hydroxysuccinimide-activated tag, which reacts preferentially with lysine residues on proteins and peptides.

The optimal conditions for tagging different aptamer affinity (or covalent) complexes may be different, and are normally determined empirically to optimize the sensitivity of the method. In one embodiment, the concentration of the tagging agent is usually sufficient to detect at least about 1% of the target molecules. In another embodiment, the concentration of the labeling agent is usually sufficient to detect at least about 10% of the target molecules. In a further embodiment, the concentration of the tagging agent is usually sufficient to detect at least about 90% of the target molecules.

In one embodiment the target is a protein or peptide and the tag is a biotin attached to the target using a standard reagent for protein biotinylation, such as, for example, NHS-PEO4-biotin. Other suitable reagents include Sulfo-NHS-LC-biotin, PFP-biotin, TFP-PEO$_3$-biotin, or any other suitable reagent that may be used to attach a tag to a protein.

As used herein, a linker is a molecular structure that is use to connect two functional groups or molecular structures. As used herein, "spacing linker" or more simply a "spacer" refers to a group of benign atoms that provide separation or spacing between two different functional groups within an aptamer. As used herein, a "releasable" or "cleavable" element, moiety, or linker refers to a molecular structure that can be broken to produce two separate components. A releasable (or cleavable) element may comprise a single molecule in which a chemical bond can be broken (referred to herein as an "inline cleavable linker"), or it may comprise two or more molecules in which a non-covalent interaction can be broken or disrupted (referred to herein as a "hybridization linker").

In some embodiments, it necessary to spatially separate certain functional groups from others in order to prevent interference with the individual functionalities. For example, the presence of a label, which absorbs certain wavelengths of light, proximate to a photocleavable group can interfere with the efficiency of photocleavage. It is therefore desirable to separate such groups with a non-interfering moiety that provides sufficient spatial separation to recover full activity of photocleavage, for example. In some embodiments, a "spacing linker" has been introduced into an aptamer with both a label and photocleavage functionality.

In one embodiment, spacing linkers are introduced into the aptamer during synthesis and so can be comprised of number of phosphoramidite spacers, including but limited to aliphatic carbon chains of length 3, 6, 9, 12 and 18 carbon atoms, polyethylene glycol chains of length 1, 3, and 9 ethylene glycol units, or a tetrahydrofuran moiety (termed dSpacer (Glenn Research) or any combination of the foregoing or any other structure or chemical component that can be designed or configured to add length along a phosphodiester backbone. In another embodiment, the spacing linker includes polynucleotides, such as poly dT, dA, dG, or dC or poly U, A, G, or C or any combination of the foregoing. In another embodiment, spacers include one or more abasic ribose or deoxyribose moieties. Note that such sequences are designed such that they do not interfere with the aptamer's structure or function.

As used herein, an "inline cleavable linker" refers to a group of atoms that contains a releasable or cleavable element. In some embodiments, an inline cleavable linker is used to join an aptamer to a tag, thereby forming a releasable tag. For example, an inline releasable linker can be utilized in any of the described assays to create a releasable connection between an aptamer and a biotin (e.g., in the affinity assays and cros slinking assays) or a releasable connection between an aptamer and a photocrosslinking group (e.g. in the crosslinking assays).

In one embodiment, the inline cleavable linker may be photo-cleavable in that it includes a bond that can be cleaved by irradiating the releasable element at the appropriate wavelength of light. In another embodiment, the inline cleavable linker may be chemically cleavable in that it includes a bond that can be cleaved by treating it with an appropriate chemical or enzymatic reagent. In another embodiment, the releasable element includes a disulfide bond that can be cleaved by treating it with a reducing agent to disrupt the bond.

As used herein, a "hybridization linker" refers to a linker that comprises two or more molecules in which a non-covalent interaction can be broken or disrupted through chemical or physical methods. In some embodiments, a hybridization linker is used to join an aptamer to a tag, thereby forming a releasable tag. For example, a hybridization linker can be utilized in any of the described assays to create a releasable connection between an aptamer and a biotin (e.g. in the affinity assays and crosslinking assays) or a releasable connection between an aptamer and a photocrosslinking group (e.g. in the crosslinking assays).

In one embodiment, a hybridization linker comprises two nucleic acids that hybridize to form a non-covalent bond. In one embodiment, one of the nucleic acids that forms the hybridization link can be a region of the aptamer itself and the other nucleic acid can be a nucleic acid that is complementary to that region. Release can be accomplished by any suitable mechanism for disrupting nucleic acid duplexes (while still maintaining compatibility with the assay). In one embodiment, 20 mM NaOH is used to disrupt the hybridization linker in the dual catch photocrosslinking assay. A hybridization linker molecule may have any suitable configuration and can include any suitable components, including one or more polynucleotides, polypeptides, peptide nucleic acids, locked nucleic acids, oligosaccharides, polysaccharides, antibodies, affybodies, antibody mimics or fragments, receptors, ligands, lipids, any fragment or derivative of these structures, any combination of the foregoing, or any other structure or chemical component that can be designed or configured to form a releasable structure.

In one embodiment, the releasable tag consists of at least one polynucleotide consisting of a suitable number of nucleotides. In one embodiment, a polynucleotide component of a linker molecule includes at least about 10 nucleotides. In another embodiment, a polynucleotide component of a linker molecule includes from about 10 to about 45 nucleotides. In yet another embodiment, a polynucleotide component of a linker molecule includes at least about 30 nucleotides. Linker molecules used in any of the methods disclosed herein can include polynucleotide components having either the same number of nucleotides or a different number of nucleotides.

"Solid support" refers to any substrate having a surface to which molecules may be attached, directly or indirectly, through either covalent or non-covalent bonds. The solid support may include any substrate material that is capable of providing physical support for the capture elements or probes that are attached to the surface. The material is generally capable of enduring conditions related to the attachment of the capture elements or probes to the surface and any subsequent treatment, handling, or processing encountered during the performance of an assay. The materials may be naturally occurring, synthetic, or a modification of a naturally occurring material. Suitable solid support materials may include silicon, a silicon wafer chip, graphite, mirrored surfaces, laminates, membranes, ceramics, plastics (including polymers such as, e.g., poly(vinyl chloride), cyclo-olefin copolymers, agarose gels or beads, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, Langmuir Blodgett films, a flow through chip, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads, crosslinked beaded Sepharose® or agarose resins, or copolymers of crosslinked bis-acrylamide and azalactone. Other beads include polymer beads, solid core beads, paramagnetic beads, or microbeads. Any other materials known in the art that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, bead, tube, well (microtiter), and the like. The solid support may be porous or non-porous, magnetic, paramagnetic, or non-magnetic, polydisperse or monodisperse, hydrophilic or hydrophobic. The solid support may also be in the form of a gel or slurry of closely-packed (as in a column matrix) or loosely-packed particles.

In one embodiment, the solid support with attached capture element is used to capture tagged aptamer affinity complexes or aptamer covalent complexes from a test mixture. In one particular example, when the tag is a biotin moiety, the solid support could be a streptavidin-coated bead or resin such as Dynabeads M-280 Streptavidin, Dynabeads MyOne Streptavidin, Dynabeads M-270 Streptavidin (Invitrogen), Streptavidin Agarose Resin (Pierce), Streptavidin Ultralink Resin, MagnaBind Streptavidin Beads (ThermoFisher Scientific), BioMag Streptavidin, ProMag Streptavidin, Silica Streptavidin (Bangs Laboratories), Streptavidin Sepharose High Performance (GE Healthcare), Streptavidin Polystyrene Microspheres (Microspheres-Nanospheres), Streptavidin Coated Polystyrene Particles (Spherotech), or any other streptavidin coated bead or resin commonly used by one skilled in the art to capture biotin-tagged molecules.

As has been described above, one object of the instant invention is to convert a protein signal into an aptamer signal. As a result the quantity of aptamers collected/detected is indicative of, and may be directly proportional to, the quantity of target molecules bound and to the quantity of target molecules in the sample. A number of detection schemes can be employed without eluting the aptamer affinity or aptamer covalent complex from the second solid support after Catch 2 partitioning. In addition to the following embodiments of detection methods, other detection methods will be known to one skilled in the art.

Many detection methods require an explicit label to be incorporated into the aptamer prior to detection. In these embodiments, labels, such as, for example, fluorescent or chemiluminescent dyes can be incorporated into aptamers either during or post synthesis using standard techniques for nucleic acid synthesis. Radioactive labels can be incorporated either during synthesis or post synthesis using standard enzyme reactions with the appropriate reagents. Labeling can also occur after the Catch 2 partitioning and elution by using suitable enzymatic techniques. For example, using a primer with the above mentioned labels, PCR will incorporate labels into the amplification product of the eluted aptamers. When using a gel technique for quantification, different size mass labels can be incorporated using PCR as well. These mass labels can also incorporate different fluorescent or chemiluminescent dyes for additional multiplexing capacity. Labels may be added indirectly to aptamers by using a specific tag incorporated into the aptamer, either during synthesis or post synthetically, and then adding a probe that associates with the tag and carries the label. The labels include those described above as well as enzymes used in standard assays for colorimetric readouts, for example. These enzymes work in combination with enzyme substrates and include enzymes such as, for example, horseradish peroxidase (HRP) and alkaline phosphatase (AP). Labels may also include materials or compounds that are electrochemical functional groups for electrochemical detection.

For example, the aptamer may be labeled, as described above, with a radioactive isotope such as $^{32}P$ prior to contacting the test sample. Employing any one of the four basic assays, and variations thereof as discussed above, aptamer detection may be simply accomplished by quantifying the radioactivity on the second solid support at the end of the assay. The counts of radioactivity will be directly proportional to the amount of target in the original test sample. Similarly, labeling an aptamer with a fluorescent dye, as described above, before contacting the test sample allows for a simple fluorescent readout directly on the second solid support. A chemiluminescent label or a quantum dot can be similarly employed for direct readout from the second solid support, requiring no aptamer elution.

By eluting the aptamer or releasing photoaptamer covalent complex from the second solid support additional detection schemes can be employed in addition to those described above. For example, the released aptamer, photoaptamer or photoaptamer covalent complex can be run on a PAGE gel and detected and optionally quantified with a nucleic acid stain, such as SYBR Gold. Alternatively, the released aptamer, photoaptamer or photoaptamer covalent complex can be detected and quantified using capillary gel electrophoresis (CGE) using a fluorescent label incorporated in the aptamer as described above. Another detection scheme employs quantitative PCR to detect and quantify the eluted aptamer using SYBR Green, for example. Alternatively, the Invader® DNA assay may be employed to detect and quantify the eluted aptamer.

In another embodiment, the amount or concentration of the aptamer affinity complex (or aptamer covalent complex) is determined using a "molecular beacon" during a replicative process (see, e.g., Tyagi et al., Nat. Biotech. 16:49 53, 1998; U.S. Pat. No. 5,925,517). A molecular beacon is a specific nucleic acid probe that folds into a hairpin loop and contains a fluorophore on one end and a quencher on the other end of the hairpin structure such that little or no signal is generated by the fluorophore when the hairpin is formed. The loop sequence is specific for a target polynucleotide sequence and, upon hybridizing to the aptamer sequence the hairpin unfolds and thereby generates a fluorescent signal.

For multiplexed detection of a small number of aptamers still bound to the second solid support, fluorescent dyes with different excitation/emission spectra can be employed to detect and quantify two, or three, or five, or up to ten individual aptamers. Similarly different sized quantum dots can be employed for multiplexed readouts. The quantum dots can be introduced after partitioning free aptamer from the second solid support. By using aptamer specific hybridization sequences attached to unique quantum dots multiplexed readings for 2, 3, 5, and up to 10 aptamers can be performed. Labeling different aptamers with different radioactive isotopes that can be individually detected, such as $^{32}P$, $^{125}I$, $^{3}H$, $^{13}C$, and $^{35}S$, can also be used for limited multiplex readouts.

For multiplexed detection of aptamers released from the Catch 2 second solid support, a single fluorescent dye, incorporated into each aptamer as described above, can be used with a quantification method that allows for the identification of the aptamer sequence along with quantification of the aptamer level. Methods include but are not limited to DNA chip hybridization, micro-bead hybridization, and CGE analysis.

In one embodiment, a standard DNA hybridization array, or chip, is used to hybridize each aptamer or photoaptamer to a unique or series of unique probes immobilized on a slide or chip such as Agilent arrays, Illumina BeadChip Arrays, or NimbleGen arrays. Each unique probe is complementary to a sequence on the aptamer. The complementary sequence may be a unique hybridization tag incorporated in the aptamer, or a portion of the aptamer sequence, or the entire aptamer sequence. The aptamers released from the Catch 2 solid support are added to an appropriate hybridization buffer and processed using standard hybridization methods. For example, the aptamer solution is incubated for 12 hours with a DNA hybridization array at about 60° C. to ensure stringency of hybridization. The arrays are washed and then scanned in a fluorescent slide scanner, producing an image of the aptamer hybridization intensity on each feature of the array. Image segmentation and quantification is accomplished using image processing software, such as ArrayVision. In one embodiment, multiplexed aptamer assays can be detected using up to 25 aptamers, up to 50 aptamers, up to 100 aptamers, up to 200 aptamers, up to 500 aptamers, up to 1000 aptamers, and up to 10,000 aptamers.

In one embodiment, addressable micro-beads having unique DNA probes complementary to the aptamers as described above are used for hybridization. The micro-beads may be addressable with unique fluorescent dyes, such as Luminex beads technology, or use bar code labels as in the Illumina VeraCode technology, or laser powered transponders. In one embodiment, the aptamers released from the Catch 2 solid support are added to an appropriate hybridization buffer and processed using standard micro-bead hybridization methods. For example, the aptamer solution is incubated for two hours with a set of micro-beads at about 60° C. to ensure stringency of hybridization. The solutions are then processed on a Luminex instrument which counts the individual bead types and quantifies the aptamer fluorescent signal. In another embodiment, the VeraCode beads are contacted with the aptamer solution and hybridized for two hours at about 60° C. and then deposited on a gridded surface and scanned using a slide scanner for identification and fluorescence quantification. In another embodiment, the transponder micro-beads are incubated with the aptamer sample at about 60° C. and then quantified using an appropriate device for the transponder micro-beads. In one embodiment, multiplex aptamer assays can be detected by hybridization to micro-beads using up to 25 aptamers, up to 50 aptamers, up to 100 aptamers, up to 200 aptamers, and up to 500 aptamers.

The sample containing the eluted aptamers can be processed to incorporate unique mass tags along with fluorescent labels as described above. The mass labeled aptamers are then injected into a CGE instrument, essentially a DNA sequencer, and the aptamers are identified by their unique masses and quantified using fluorescence from the dye incorporated during the labeling reaction. One exemplary example of this technique has been developed by Althea Technologies.

In many of the methods described above, the solution of aptamers can be amplified and optionally tagged before quantification. Standard PCR amplification can be used with the solution of aptamers eluted from the Catch 2 solid support. Such amplification can be used prior to DNA array hybridization, micro-bead hybridization, and CGE readout.

In another embodiment, the aptamer affinity complex (or aptamer covalent complex) is detected and/or quantified using Q-PCR. As used herein, "Q-PCR" refers to a PCR reaction performed in such a way and under such controlled conditions that the results of the assay are quantitative, that is, the assay is capable of quantifying the amount or concentration of aptamer present in the test sample.

In one embodiment, the amount or concentration of the aptamer affinity complex (or aptamer covalent complex) in the test sample is determined using TaqMan® PCR. This technique generally relies on the 5'-3' exonuclease activity of the oligonucleotide replicating enzyme to generate a signal from a targeted sequence. A TaqMan probe is selected based upon the sequence of the aptamer to be quantified and generally includes a 5'-end fluorophore, such as 6-carboxyfluorescein, for example, and a 3'-end quencher, such as, for example, a 6-carboxytetramethylfluorescein, to generate signal as the aptamer sequence is amplified using polymerase chain reaction (PCR). As the polymerase copies the aptamer sequence, the exonuclease activity frees the fluorophore from the probe, which is annealed downstream from the PCR primers, thereby generating signal. The signal increases as replicative product is produced. The amount of PCR product depends upon both the number of replicative cycles performed as well as the starting concentration of the aptamer.

In another embodiment, the amount or concentration of an aptamer affinity complex (or aptamer covalent complex) is determined using an intercalating fluorescent dye during the replicative process. The intercalating dye, such as, for example, SYBR® green, generates a large fluorescent signal in the presence of double-stranded DNA as compared to the fluorescent signal generated in the presence of single-stranded DNA. As the double-stranded DNA product is formed during PCR, the signal produced by the dye increases. The magnitude of the signal produced is dependent upon both the number of PCR cycles and the starting concentration of the aptamer.

In another embodiment, the aptamer affinity complex (or aptamer covalent complex) is detected and/or quantified using mass spectrometry. Unique mass tags can be introduced using enzymatic techniques described above. For mass spectroscopy readout, no detection label is required, rather the mass itself is used to both identify and, using techniques commonly used by those skilled in the art, quantified based on the location and area under the mass peaks generated during the mass spectroscopy analysis. An example using mass spectroscopy is the MassARRAY® system developed by Sequenom.

Figure 3E:
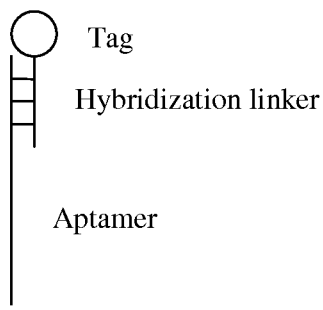
Figure 3F:
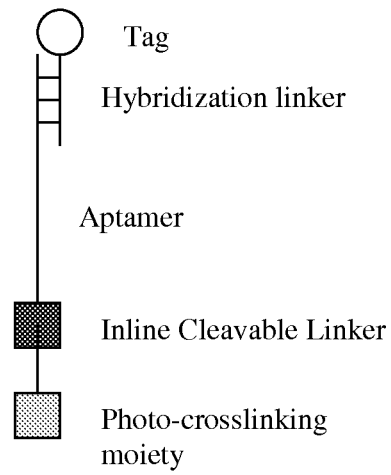
Figure 3G:
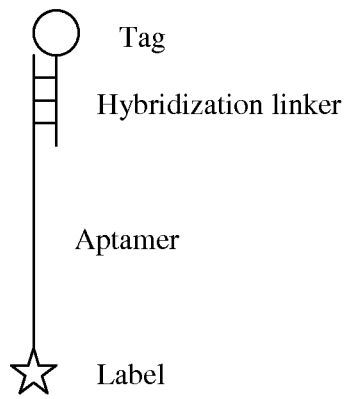
Figure 3H:
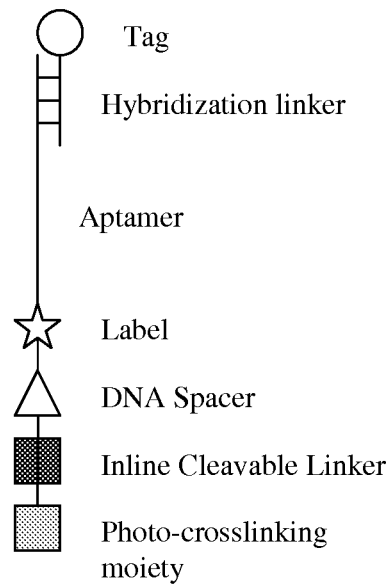

In other embodiments, aptamer constructs that include different built-in functionalities are provided. These functionalities may include tags for immobilization, labels for detection, photoreactive groups, means to promote or control separation, etc. In one embodiment, an aptamer includes a cleavable or releasable section (also described as an element or component) in the aptamer sequence. These additional components or elements are structural elements or components that introduce additional functionality into the aptamer. In other embodiments, the aptamer includes one or more of the following additional components (also described as a functional or structural element or component or moiety): a labeled or detectable component, a spacer component, a cleavable element, and a specific binding tag or immobilization element or component. For example, in one embodiment of the photocrosslinking aptamer, the aptamer includes a tag connected to the aptamer via a cleavable moiety, a label, a spacer component separating the label and the cleavable moiety, and a photocrosslinking moiety, as shown in FIG. 3L.

All aptamer constructs can be synthesized using standard phosphoramidite chemistry. Representative aptamer constructs are shown in FIG. 3A through FIG. 3L. The functionality can be split between the 5' and 3' end or combined on either end. In addition to photocleavable moieties, other cleavable moieties can be used, including chemically or enzymatically cleavable moieties. A variety of spacer moieties can be used and one or more biotin moieties can be included. Tags (also referred to as immobilization or specific binding elements or components) other than biotin can also be incorporated. Suitable construction reagents include biotin phosphoramidite, PC Linker (Glen Research PN 10-4920-02); PC biotin phosphoramidite (Glen Research PN 10-4950-02); dSpacer CE phosphoramidite (Glen Research PN 10-1914-02); Cy3 phosphoramidite (Glen Research PN 10-5913-02); and Arm26-Ach Spacer Amidite (Fidelity Systems PN SP26Ach-05). As illustrated in FIG. 3K, a fluorescent dye (such as Cy3), a spacer, the photocleavable and biotin moieties may be added to the end of the aptamer. In one embodiment, because of potential interactions between the photocleavable moiety and the dye, the spacer is inserted between these two moieties.

Figure 3I:
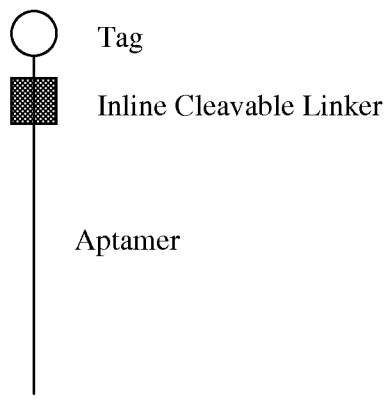
Figure 3J:
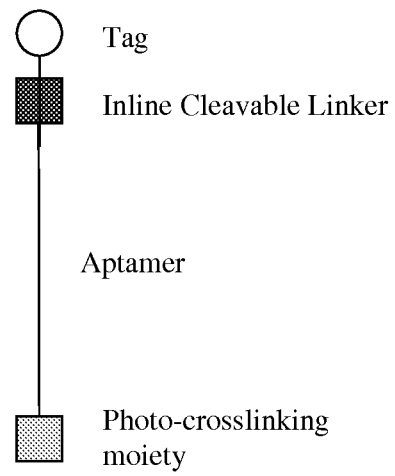
Figure 3K:
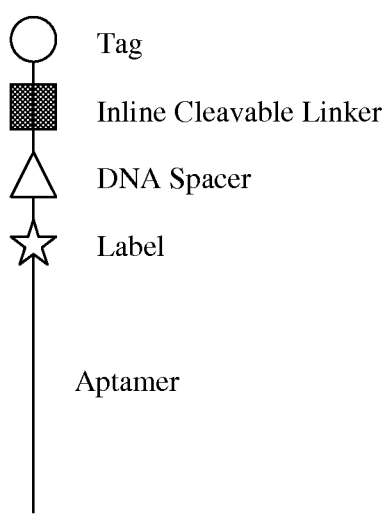
Figure 3L:
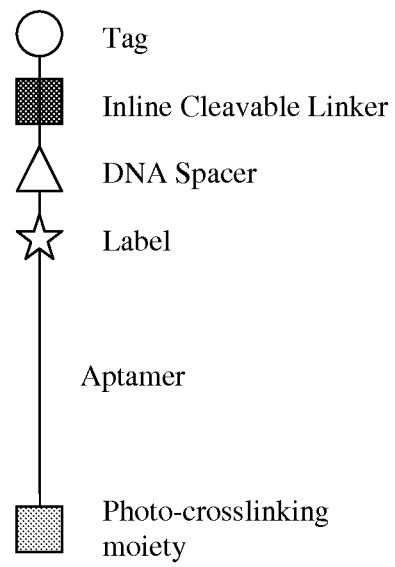
Figure 5A:
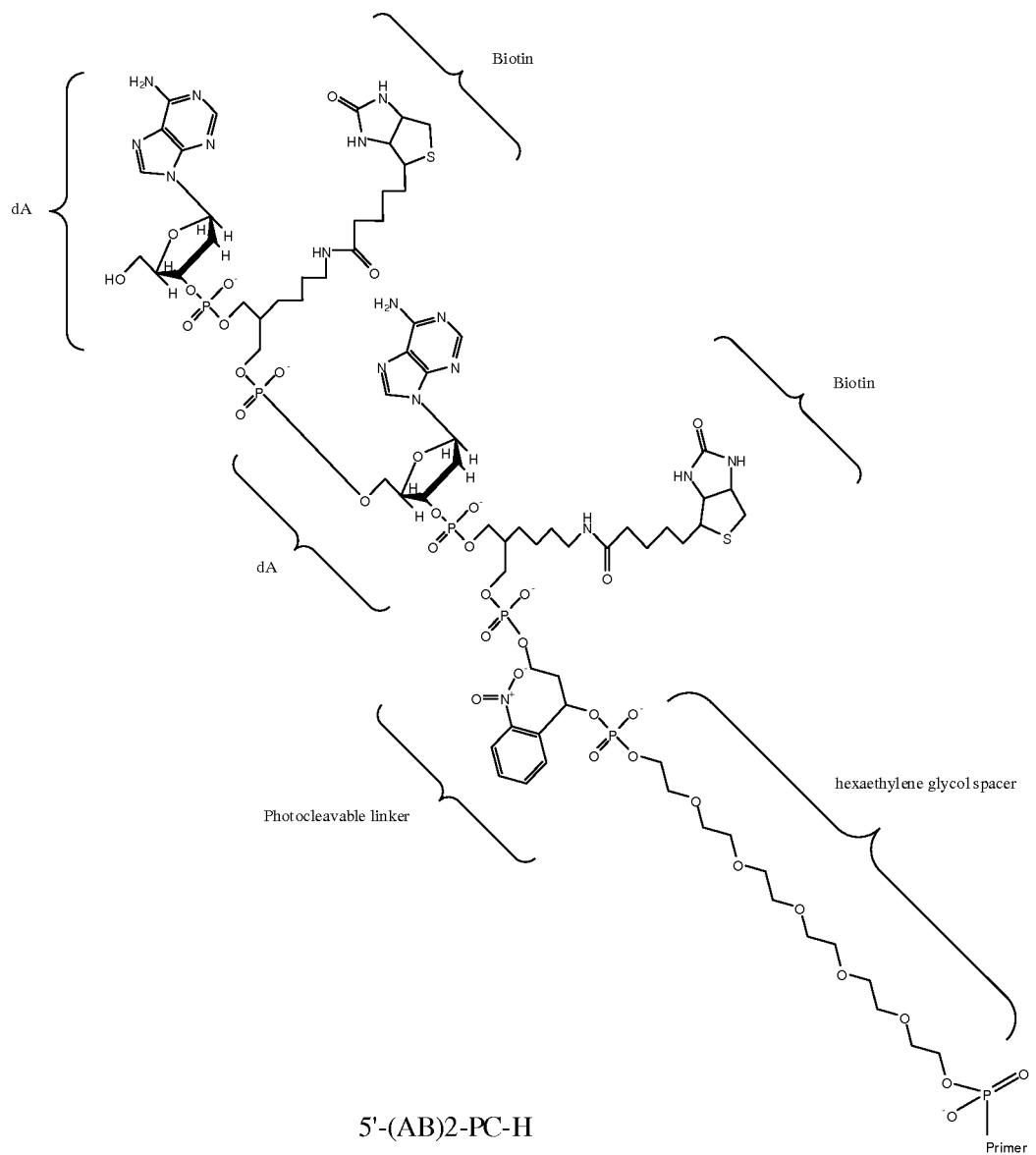
FIG. 5A illustrates an example of a hybridization tag.
Figure 5B:
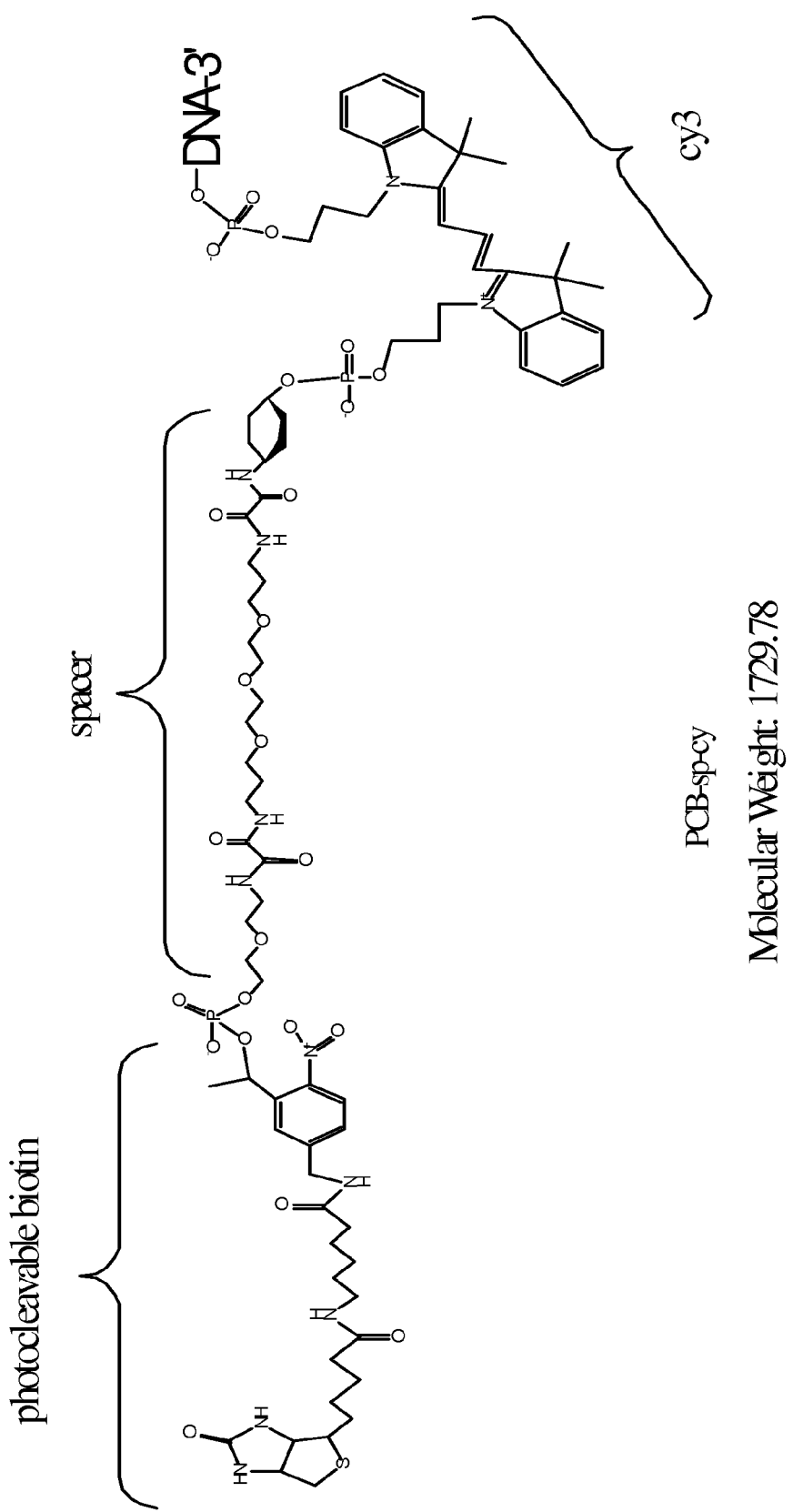
FIGS. 5B to 5D illustrate examples of aptamer constructs including a cleavable or releasable element, a tag (for example biotin), a spacer, and a label (for example Cy3).
Figure 5C:
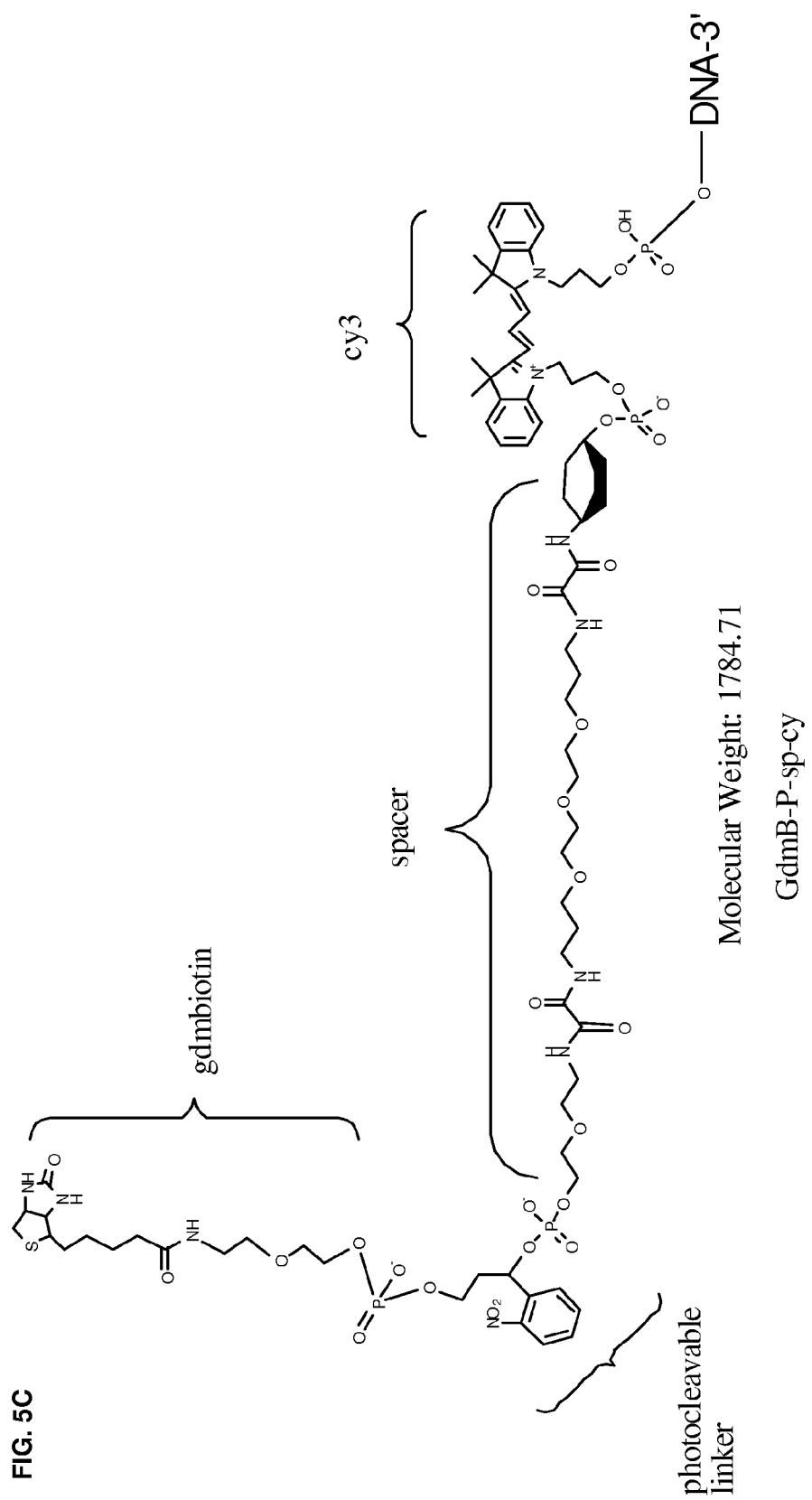
Figure 5D:
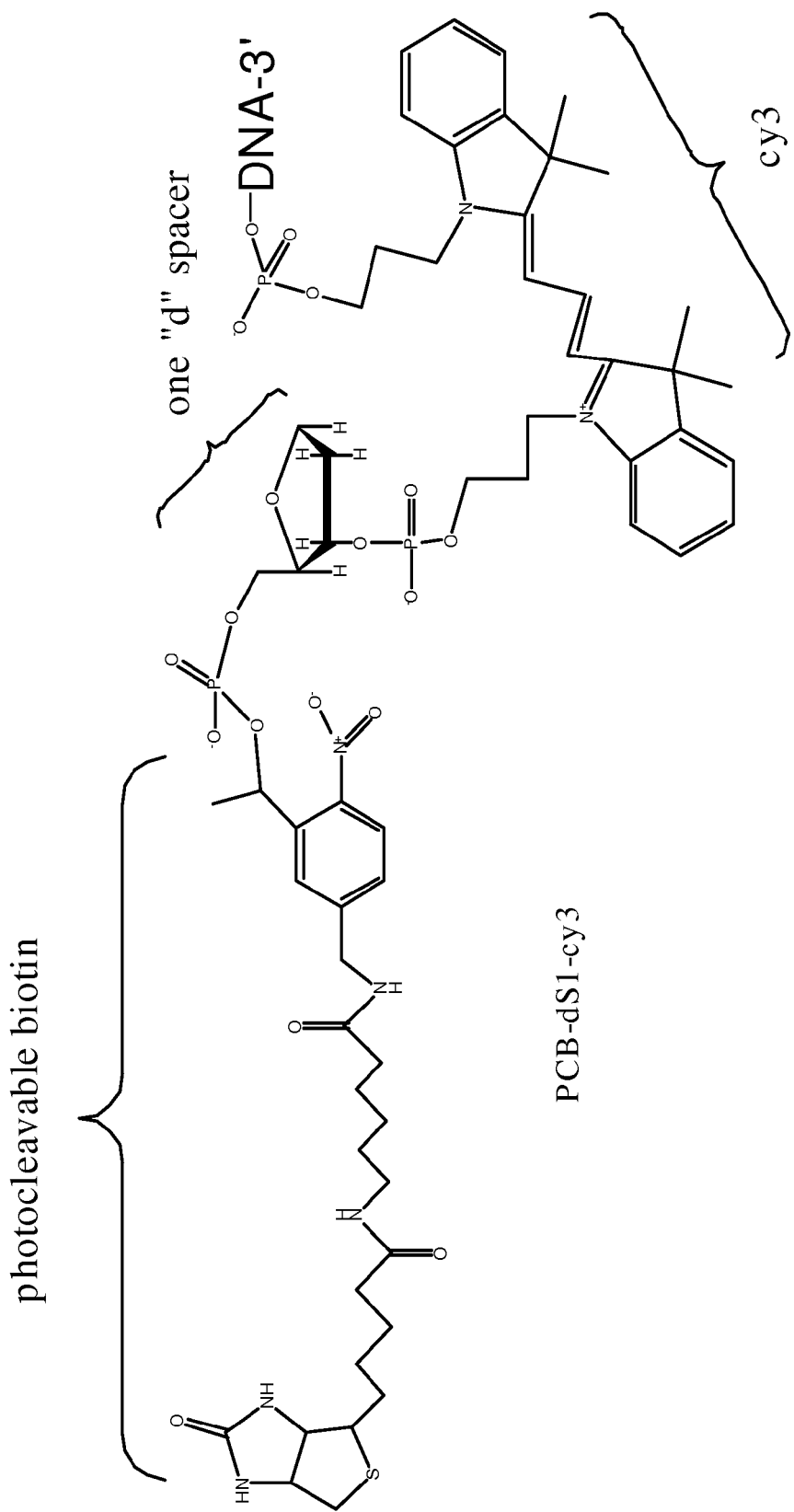

In one embodiment, the tag is covalently attached to the aptamer, as illustrated in FIGS. 3I-3K. In another embodiment, the tag is indirectly attached to the aptamer in the form of a hybridized polynucleotide sequence, which is complementary to a portion of the aptamer sequence, that has a covalently attached tag, as illustrated in FIGS. 3E-3H.

In one embodiment, an aptamer can be further modified to include a first cleavable moiety positioned between the crosslinking group and a unique sequence within the aptamer. This first cleavable moiety may, for example, be cleavable by a variety of different means including, chemical, photochemical or ionic depending upon the cleavable moiety employed. In one embodiment, an aptamer has the structure is shown in FIG. 3B. For example, the photocrosslinking group may be 4-azido-2-nitro-aniline and the photocleavable group, or releasable moiety, may be a PC Linker available from Glen Research as a phosphoramidite (-(4,4'-dimethoxytrityl)-1-(2-nitrophenyl)-propan-1-yl-[(2-cyanoethyl)-(N,N-diisopropyl)]-phosphoramidite).

In other embodiments, the aptamer includes a capture tag that is joined to the aptamer through a releasable group. For example, a biotin capture tag may be attached to the aptamer via a second oligonucleotide that hybridizes to the aptamer as illustrated in FIG. 3F. In other embodiments, other capture tags or cleavable elements can be attached to the same aptamer. For example, a poly-His tag may be attached to the aptamer via a second chemical or photocleavable moiety. The advantage to this aptamer construct is that two different processing steps can be applied to separate the aptamer affinity (or covalent) complex from other components in the test sample. These separation steps can be used in any sequence desired.

In another embodiment, a detection label can also be included within the aptamer as illustrated in FIG. 3C. This detection label provides for the detection and/or quantification of the free aptamer in the final step of the assay as described in detail above. For example, for fluorescent detection, a fluorescent dye such as Cy3 or Cy5 dye may be incorporated within aptamer. A Cy3 may be introduced using the Cy3 phosphoramidite from Glen Research ([344-monomethoxytrityloxy)propyl]-1'-[3-[(2-cyanoethyl)-(N,N-diisopropyl) phosphoramidityl]propyl]-3,3,3',3'-tetramethylindocarbocyanine chloride)), but any suitable label may be included in the aptamer.

As used in this specification, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, the term "about" represents an insignificant modification or variation of the numerical values such that the basic function of the item to which the numerical value relates is unchanged.

As used herein, "associate," "associates," and any variation thereof refers to an interaction or complexation between a tag and a probe resulting in a sufficiently stable complex so as to permit separation of "unassociated" or unbound materials, such as, for example, unbound components of a test sample, from the tag-probe complex under given complexation or reaction conditions. A tag and a probe can associate with each other directly by interacting and binding to each other with specificity. A tag and a probe can also associate with each other indirectly such as when their complexation is mediated by a linker molecule.

A computer program may be utilized to carry out one or more steps of any of the methods disclosed herein. Another aspect of the present disclosure is a computer program product comprising a computer readable storage medium having a computer program stored thereon which, when loaded into a computer, performs or assists in the performance of any of the methods disclosed herein.

One aspect of the disclosure is a product of any of the methods disclosed herein, namely, an assay result, which may be evaluated at the site of the testing or it may be shipped to another site for evaluation and communication to an interested party at a remote location, if desired. As used herein, "remote location" refers to a location that is physically different than that at which the results are obtained. Accordingly, the results may be sent to a different room, a different building, a different part of city, a different city, and so forth. The data may be transmitted by any suitable means such as, e.g., facsimile, mail, overnight delivery, e-mail, ftp, voice mail, and the like.

"Communicating" information refers to the transmission of the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

EXAMPLES

The following examples are provided for illustrative purposes only and are not intended to limit the scope of the invention as defined in the appended claims.

The foregoing describes the disclosure with reference to various embodiments and examples. No particular embodiment, example, or element of a particular embodiment or example is to be construed as a critical, required, or essential element or feature of any of the claims.

It will be appreciated that various modifications and substitutions can be made to the disclosed embodiments without departing from the scope of the disclosure as set forth in the claims below. The specification, including the figures and examples, is to be regarded in an illustrative manner, rather than a restrictive one, and all such modifications and substitutions are intended to be included within the scope of the disclosure. Accordingly, the scope of the disclosure may be determined by the appended claims and their legal equivalents, rather than by the examples. For example, steps recited in any of the method or process claims may be executed in any feasible order and are not limited to an order presented in any of the embodiments, the examples, or the claims.

Example 1

Aptamer and Primer Constructs

Aptamer and biotinylated primer constructs with different 5'-terminal functional groups were produced and the differences are shown in FIG. 6. The aptamer contained a Cy3 fluorescent dye (Cy3 Phosphoramidite from Glen Research (-[3-(4-monomethoxytrityloxy)propyl]-1'-[3-[(2-cyanoethyl)-(N,N-diisopropyl) phosphoramidityl]propyl]-3,3,3',3'-tetramethylindocarbocyanine chloride)) at the 5' terminus, and the primer contained two biotin residues ((AB)$_2$), a (T)$_8$ linker, and a photocleavable moiety (PC Linker available from Glen Research as a phosphoramidite (-(4,4'-Dimethoxytrityl)-1-(2-nitrophenyl)-propan-1-yl-[(2-cyanoethyl)-(N, N-diisopropyl)]-phosphoramidite). For the method described in FIG. 6, the aptamer contained a photoreactive crosslinking group referred to herein as ANA (4-azido-2-nitro-aniline), a photocleavable moiety (PC Linker), and a Cy3 dye at the 5' terminus, and the primer contained two biotin residues and a (T)$_8$ linker.

Example 2

Affinity Binding Method (2 Catch Method)

a) Buffer

30 µL of a Cy3-aptamer mixture (2 nM each aptamer) was combined with 30 µL of an (AB)$_2$-T8-PC-primer mixture (6 nM for each primer) in SB17T and incubated at 95° C. for 4 minutes, at 37° C. for 13 minutes. In a separate reaction, 60 µL of a target protein mixture was prepared (2× concentration in SB17T). 55 µL of the target protein mixture was combined with 55 µL of the aptamer/primer mixture in a 96-well plate (Omni-Tube Plate, Abgene #AB0407) and incubated at 37° C. for 15 minutes to achieve binding equilibrium. All following steps were performed at room temperature unless otherwise noted.

b) Plasma, Serum or Whole Blood

30 µL of a Cy$_3$-aptamer mixture (2 nM each aptamer) was combined with 30 µL of an (AB)2-T8-PC-primer mixture (6 nM for each primer) in SB17T and incubated at 95° C. for 4 minutes, at 37° C. for 13 minutes. In a separate reaction, 30 µL of a 1× to 2.5× dilution of a complex biological protein mixture (plasma, serum, whole blood) was prepared in a diluent containing Z-block competitor oligonucleotide (5'-(ACZZ)$_7$AC-3', where Z=5-benzyl-dUTP, 4 µM) and incubated for 5 minutes. The complex biological protein mixture was combined with 30 µL of a target protein mixture (4× concentration in SB17T). 55 µL of the target protein/biological matrix mixture was combined with 55 µL of the aptamer/primer mixture and incubated at 37° C. for 15 minutes to achieve binding equilibrium. All following steps were performed at room temperature unless otherwise noted.

c) Biotinylated Aptamer Capture and Free Protein Removal.

133 µL of streptavidin-agarose resin (Pierce Immobilized Streptavidin, #20353, 7.5% aqueous slurry) was washed twice with 200 µL SB17T by vacuum filtration through a Durapore membrane (MultiScreen-HV45, Millipore #MAHVN4550). 100 µL of the aptamer:protein mixture was added to the washed resin and is mixed for 15 minutes. The resin was washed once with 200 µL SB17T containing 10 µM biotin (Sigma-Aldrich, Inc. #B4501-1G) and once with 200 µL SB17T by vacuum filtration.

d) Protein Tagging and Aptamer Release

100 µL of SB17T containing 1.2 mM NHS-PEO4-biotin (Pierce #21329) was added to the washed resin and mixed for 20 minutes. The resin was washed five times with 200 µL SB17T by vacuum filtration and once with 200 µL SB17T by centrifugation, resuspended in 75 µL SB17T containing 10 mM dextran sulfate (Mr ~5000, Sigma-Aldrich #31404), and irradiated with a UV lamp (two Sylvania 350 Blacklight bulbs, 15W, sample 5 cm from source) 5 minutes with mixing. The resin was removed by centrifugation through the Durapore membrane, and the eluate with released aptamer:protein complexes was collected in a 1.1 mL 96-well plate (1.1 mL Deep-Well plate, Marsh Biomedical #DW9611) containing 150 µL SB17T+10 mM dextran sulfate.

e) Protein Capture and Free Aptamer Removal

50 µL of streptavidin resin (DynaBeads MyOne Streptavidin C1, Invitrogen #650-03, 10 mg/mL in SB17T) was added to a Durapore membrane. The 225 µL aptamer:protein mixture was added to the resin and mixed for 15 minutes. The resin was washed twice with 200 µL SB17T containing 10 mM dextran sulfate, once with 200 µL SB17T by vacuum filtration, and once with 200 µL SB17T by centrifugation.

f) Complexed Aptamer Release

The resin was resuspended in 90 µL Elution Buffer (2 mM NaOH, 0.1% TWEEN-20) and mixed for 5 minutes. During this time, aptamer is released from the protein:aptamer complex. The resin was removed by centrifugation, and the eluate with released aptamer was collected. 80 µL eluate was neutralized and buffered with 20 µL Neutralization Buffer (8 mM HCl, 0.5 mM Tris-HCl (pH 7.5), 0.1% TWEEN-20). Aptamer was detected as described in Example 4.

g) Results

A twelve point dilution series in buffer was created for eleven protein analytes (bFGF, Eotaxin-2, FGF7, FGF-16, GDNF, IL-7, IL-20, Lymphotactin, TARC, tPA, VEGF) starting with a 10 nM or 3 nM (bFGF, FGF7, tPA, Lymphotactin) concentration of each analyte and serially diluting to 33 fM with half-log dilutions (dilution factor of 3.1623). Two no protein controls were included to give a total of fourteen samples. The Cy3-aptamer mixture contained the eleven aptamers to the target proteins in the dilution series as well as twenty-eight control aptamers whose target proteins were absent. Three replicate dilution series were prepared. The results are set forth in FIGS. 7-10.

Figure 7A:
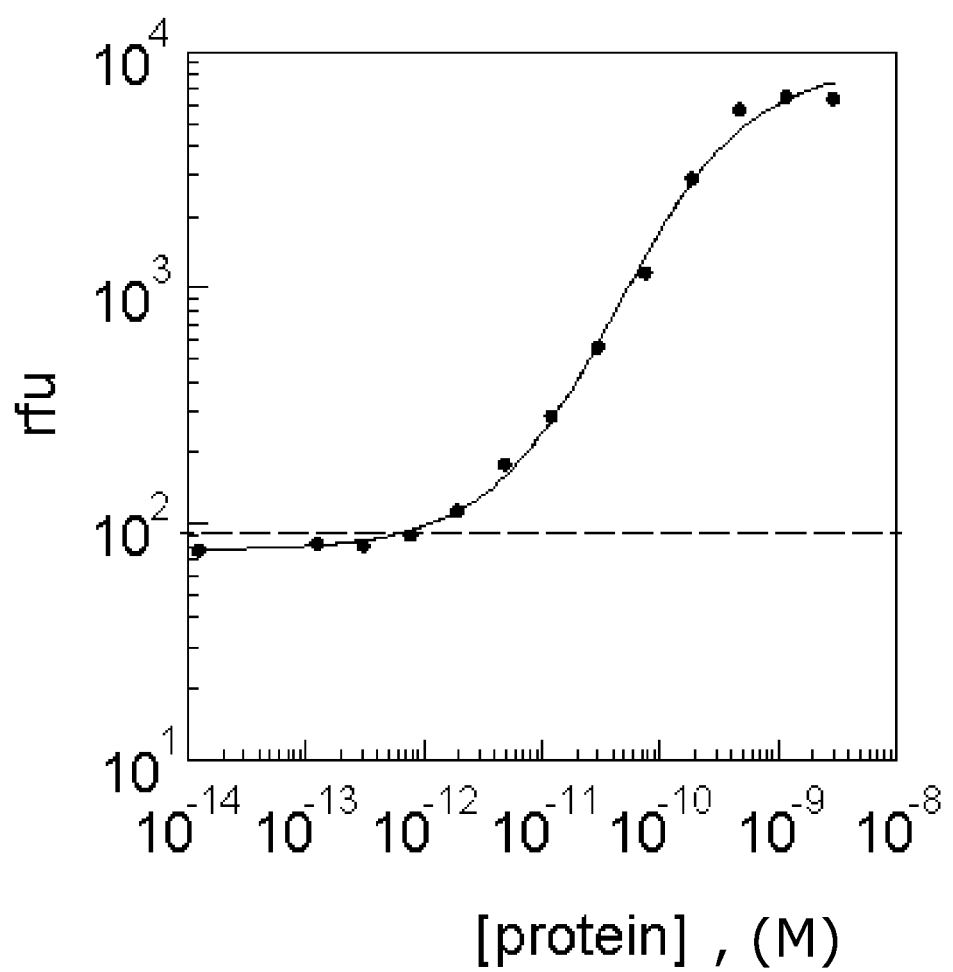
FIGS. 7A, 7B and 7C illustrate dose response curves (RFU vs log input target protein concentration) for detection of target proteins in buffer using the Affinity Assay Protocol with Microarray Detection. Replicate no-protein control values are plotted on the y-axis frame. The solid lines represent a sigmoidal fit through the data points. The dashed lines represent two standard deviations of the replicate no-protein values.
Figure 7B:
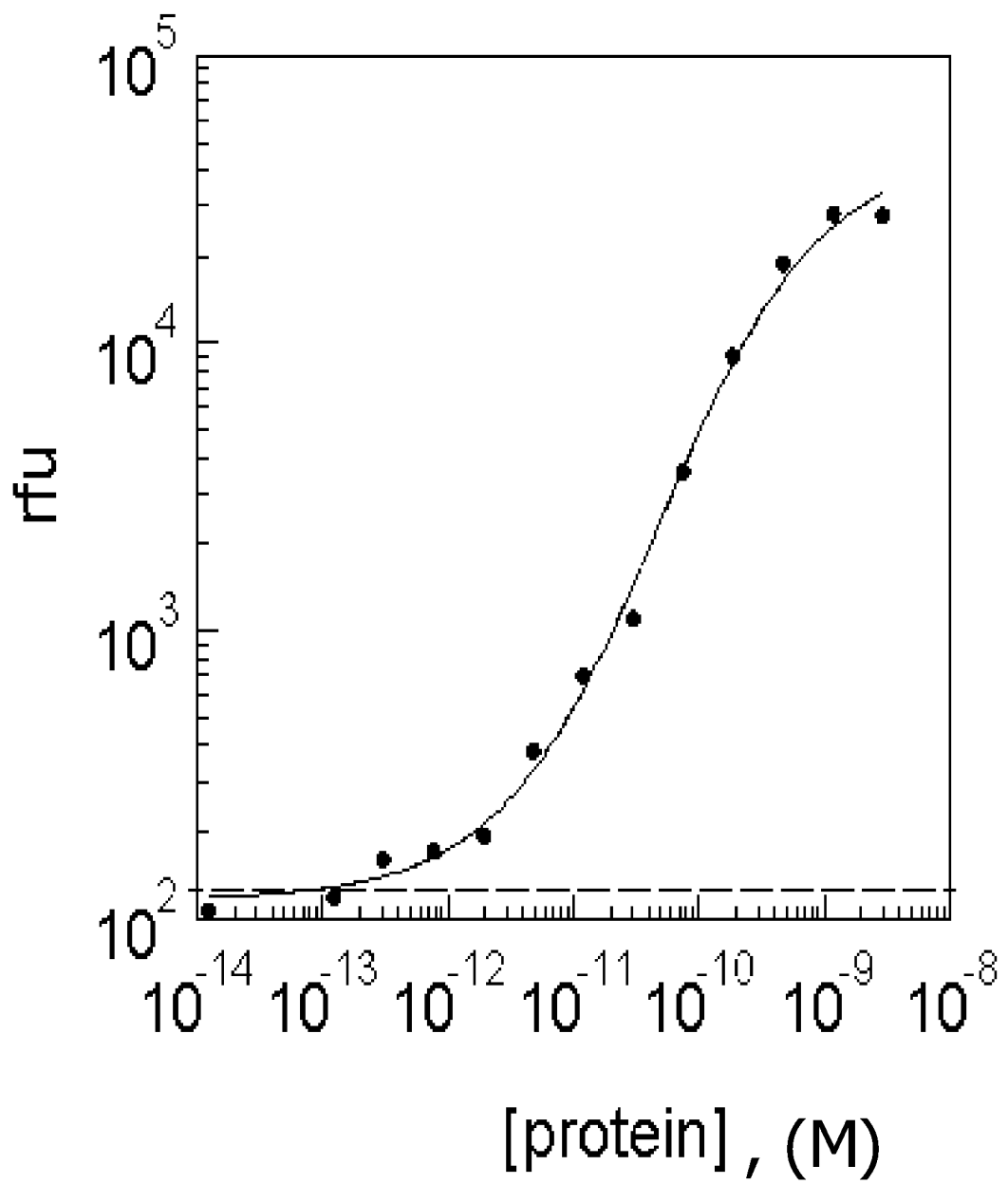
Figure 7C:
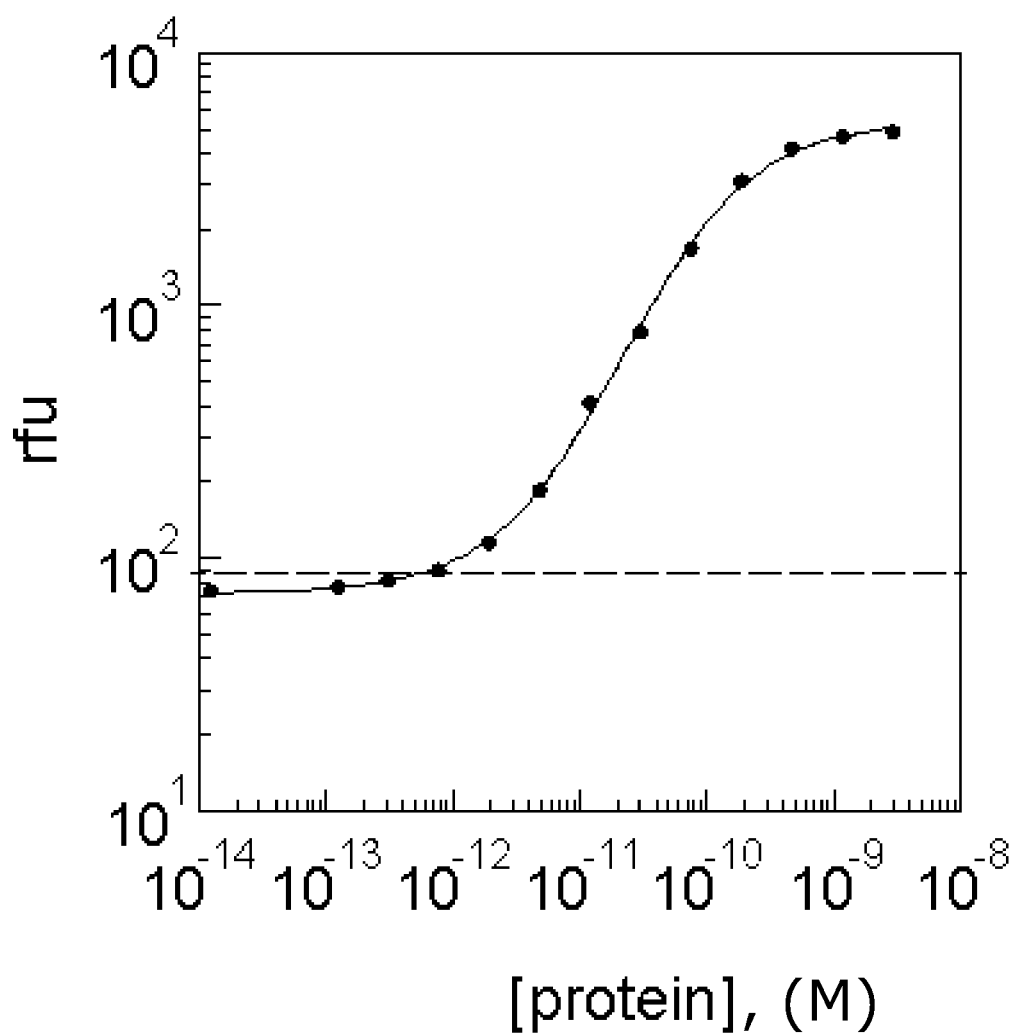

FIGS. 7A to 7C show relative fluorescence units (RFU) versus concentration plots (log-log dose response curve) for three of the eleven target proteins in buffer. Limit of Detection values (LOD) were calculated for each protein as the protein concentration giving a signal equal to the average plus two standard deviations of the no-protein values). LODs for the three proteins were 630 fM (bFGF), 90 fM (FGF7) and 530 fM (Lymphotactin). The affinity assay is able to detect proteins in buffer at sub-picomolar levels.

Figure 8:
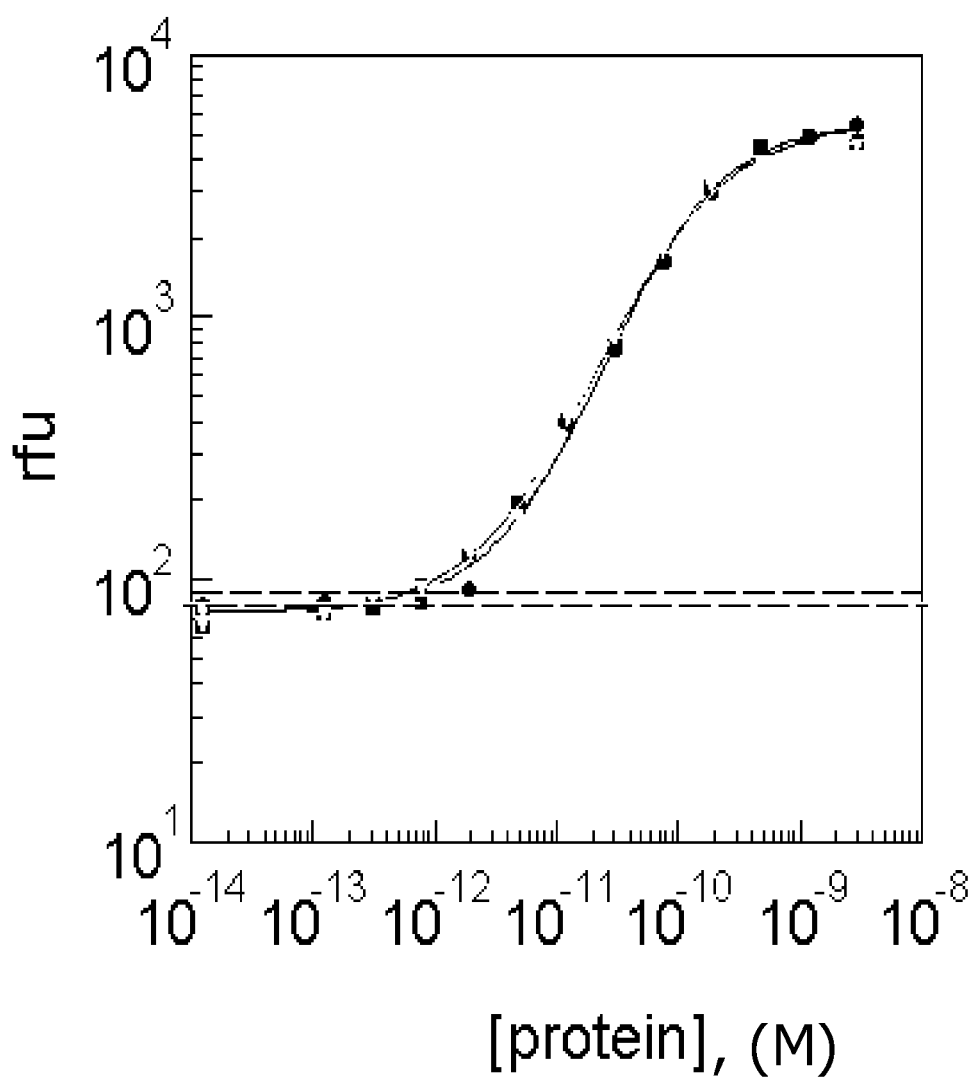
FIG. 8 illustrates the dose response curves for three replicate measurements of the target protein Lymphotactin in buffer using the Affinity Assay Protocol with Microarray Detection. Replicate no-protein control values are plotted on the y-axis frame. The solid lines represent sigmoidal fits through the data points for each of the three replicates.

FIG. 8 shows a relative fluorescence units (RFU) versus concentration plot for three replicate measurements for the target protein Lymphotactin in buffer. The three lines represent dose response curves for each of the three replicates. The replicate curves are in very good agreement with each other indicating a high level of reproducibility for the affinity assay protocol.

A twelve point dilution series was also conducted in 10% plasma for five protein analytes (bFGF, Eotaxin-2, Lymphotactin, tPA and VEGF) starting with a 10 nM (VEGF and Eotaxin-2) or 3 nM (bFGF, tPA, Lymphotactin) concentration of each analyte and serially diluting to 420 fM or 126 fM with 2.5-fold dilutions. Two no-protein controls were included to give a total of fourteen samples that were subsequently hybridized on a microarray slide. The Cy3-aptamer mixture contained the five aptamers to the target proteins in the dilution series as well as five control aptamers whose target proteins were absent. The assay was performed as described above with the following exceptions. 100% PPT-plasma (pooled human plasma) was diluted 1 to 2 with 5 µM Z-block in 0.5×SB18, 0.05% TWEEN-20. 40 µL of this 50% plasma solution was mixed with 60 µL of a protein mixture at 3.33× the final concentration. 50 µL of the plasma/protein mixture was combined with 50 µL of aptamer/primer mixture (3 nM aptamer, 9 nM primer). The equilibration binding reaction was performed at 37° C. for 15 min. 40 µL of the whole blood-protein-aptamer mixture (instead of 100 µL) was added to the streptavidin-agarose resin and mixed for 15 min.

Figure 9:
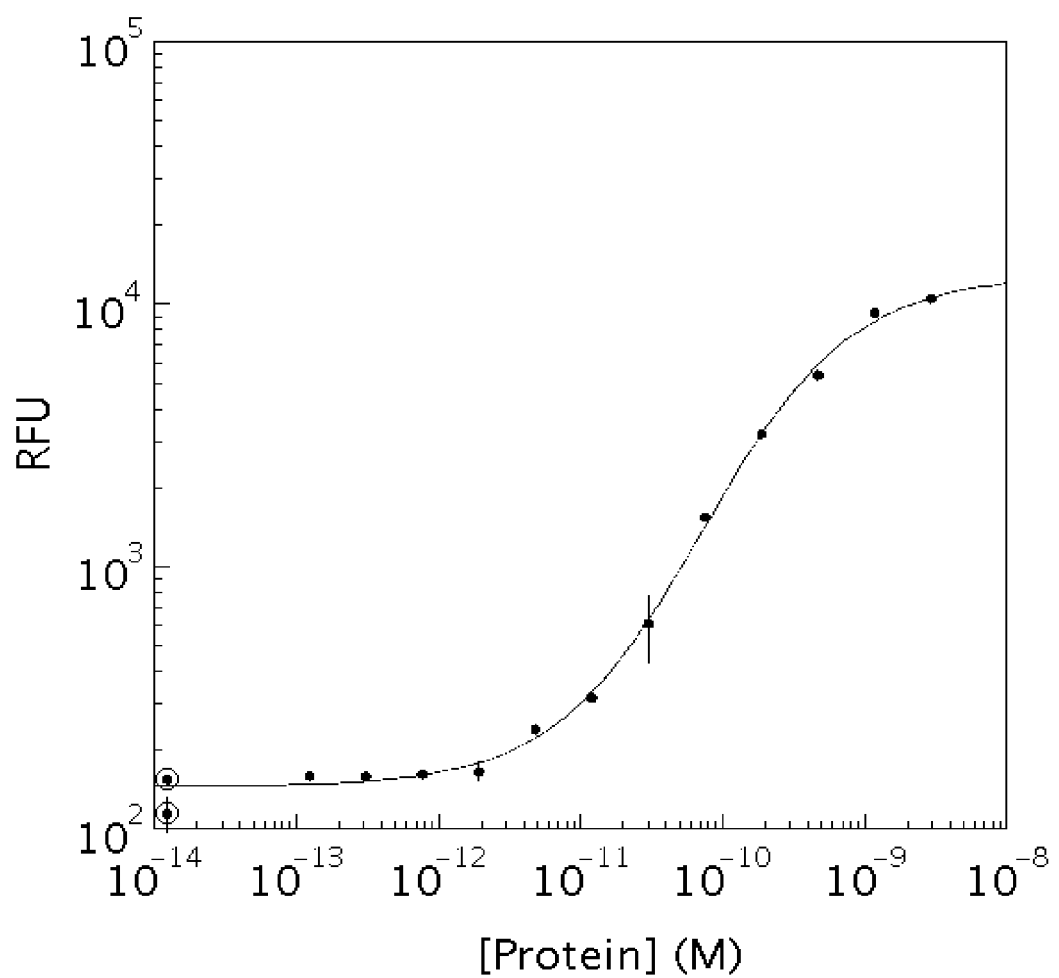
FIG. 9 illustrates the dose response curve (RFU versus log input target protein concentration) for detection of the target protein Lymphotactin in 10% human plasma using the Affinity Assay Protocol and Microarray Detection. Replicate no-protein control values are plotted on the y-axis frame and circled. The solid line represents a sigmoidal fit through the data points.

FIG. 9 shows a relative fluorescence units (RFU) versus concentration plot for the target protein Lymphotactin in 10% human plasma. This curve is similar in shape and response to the dose response curves in buffer. This shows that the affinity assay protocol can be performed, but is not limited to 10% plasma solution.

Figure 10:
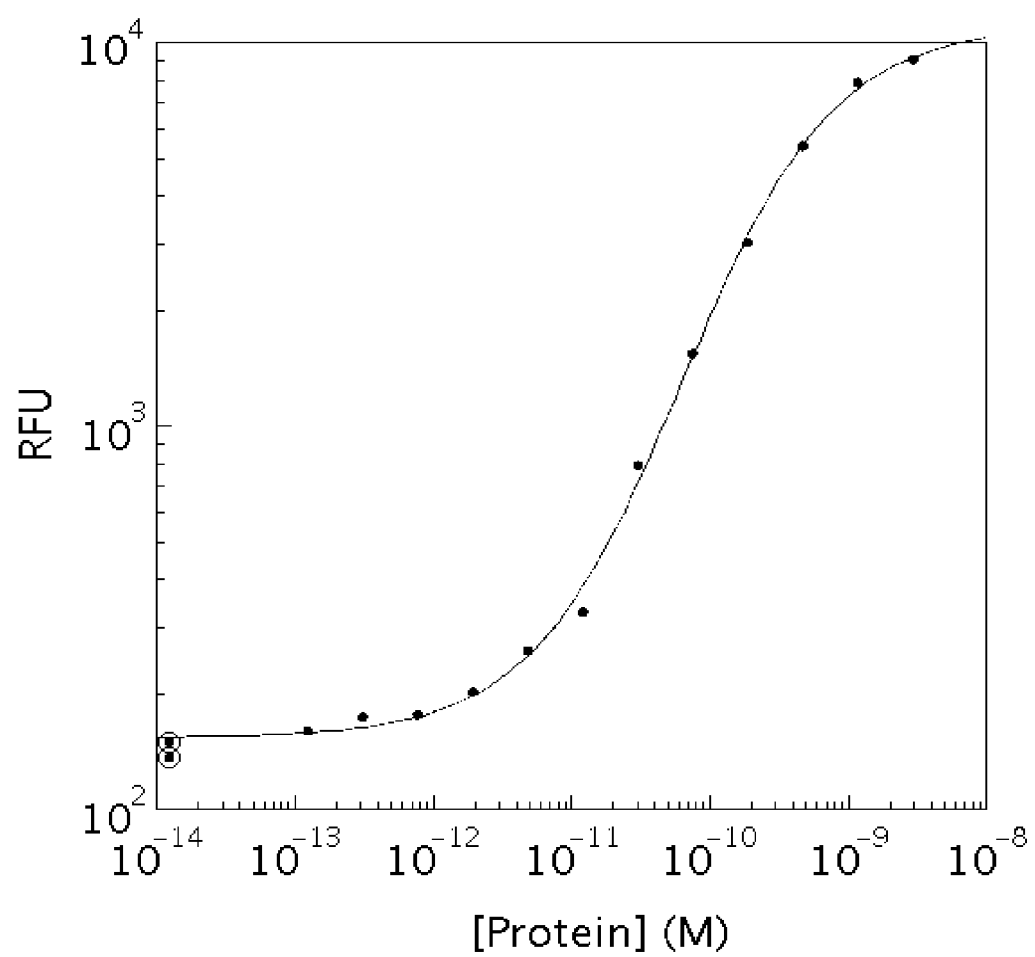
FIG. 10 illustrates the dose response curve (RFU versus log input target protein concentration) for detection of the target protein Lymphotactin in 10% whole human blood using the Affinity Assay Protocol and Microarray Detection. Replicate no-protein control values are plotted on the y-axis frame and circled. The solid line represents a sigmoidal fit through the data points.

FIG. 10 shows a relative fluorescence units (RFU) versus concentration plot for the target protein Lymphotactin in 10% whole human blood. This curve is similar in shape and response to the dose response curves in 10% human plasma (FIG. 9), and demonstrates the performance of the affinity assay protocol in complex biological matrices without any apparent matrix effects.

Example 3

Photo-Crosslink Assay Protocol

All steps of this protocol were performed with minimal light exposure to prevent photoactivation of the photo-aptamer.

a) Protein Binding

30 µL of an ANA-PC-Cy3-aptamer mixture (2 nM each aptamer) was combined with 30 µL of an (AB)2-T8-primer mixture (6 nM for each aptamer) in SB 17T Buffer (40 mM HEPES, pH 7.5, 120 mM NaCl, 5 mM KCl, 5 mM $MgCl_2$, 1 mM EDTA, 0.05% TWEEN-20) and incubated at 95° C. for 4 minutes, at 37° C. for 13 minutes. In a separate reaction, 60 µL of a protein mixture was prepared at a 2× concentration. 55 µL of the target protein mixture was combined with 55 µL of the aptamer/primer mixture in a 96-well plate (Omni-Tube Plate, Abgene #AB0407) and incubated at 37° C. for 15 minutes to achieve binding equilibrium. All following steps were performed at room temperature unless otherwise noted.

b) Kinetic Challenge and Photo-Crosslinking

100 µL of equilibrated sample was added to 1400 µL SB17T containing 10 mM dextran sulfate (Mr ~5000, Sigma-Aldrich #31404) and incubated at 37° C. for 15 minutes. The 1.5 mL sample was irradiated with 470 nm light (Custom LED array) at 37° C. for 10 minutes to covalently crosslink the bound proteins to the photoaptamers.

c) Biotinylated Aptamer Capture and Free Protein Removal

40 µL of streptavidin resin (DynaBeads MyOne Streptavidin C1, Invitrogen #650-03, 10 mg/mL in SB17T) was added to the 1.5 mL sample and incubated at 25° C. for 30 minutes with mixing. The resin was pelleted by centrifugation and 1.4 mL of supernatant was removed. The resin and remaining supernatant were transferred to a Durapore membrane (MultiScreen-HV45, Millipore #MAHVN4550) and the supernatant was removed by vacuum filtration. The resin was washed twice with 200 µL SB17T containing 10 µM biotin (Sigma-Aldrich, Inc. #B4501-1G) and once with 200 µL SB17T by vacuum filtration.

d) Protein Tagging and Aptamer (Free and Complexed) Release

100 µL of SB17T containing 1.2 mM NHS-PEO4-biotin (Pierce #21329) was added to the washed resin and mixed for 20 minutes. The resin was washed three times with 200 µL Guanidine Wash Buffer (3M guanidine, 50 mM NaCl, 40 mM HEPES pH 7.5, 2 mM EDTA, 0.05% TWEEN-20, 1 mM TROLOX), and twice with 200 µL HEPES Wash Buffer (50 mM NaCl, 40 mM HEPES pH 7.5, 0.05% TWEEN-20, 1 mM TROLOX) by vacuum filtration. The resin was resuspended in 110 µL 20 mM NaOH and mixed for 5 minutes. The resin was removed by centrifugation, and the NaOH eluate with released aptamer:protein complexes was collected. 100 µL of eluate was neutralized with 25 µL 80 mM HCl, and buffered with 10 µL 55 mM HEPES (pH 7.5) containing 2M NaCl and 1% TWEEN-20.

e) Protein Capture and Free Aptamer Removal

133 µL of streptavidin resin (Pierce Immobilized Streptavidin, #20347, 10% aqueous slurry) was washed twice with 200 µL SB17T by vacuum filtration through a Durapore PVDF membrane. The 135 µL aptamer:protein mixture was added to the washed resin and mixed for 20 minutes. The resin was washed once with 200 µL Guanidine Wash Buffer at 50° C. for 10 minutes with mixing, once with 200 µL 20 mM NaOH for 2 minutes with mixing, twice with 200 µL SB17T by vacuum filtration, and once with 200 µL SB17T by centrifugation.

f) Photo-Crosslinked Aptamer Release

The resin was resuspended in 100 µL SB17T and irradiated with a UV lamp (two Sylvania 350 Blacklight bulbs, 15W, sample 5 cm from source) for 20 minutes with mixing. During this time, aptamer photo-crosslinked to protein is released by photocleavage. The resin was removed by centrifugation through the Durapore membrane, and the eluate with released aptamer was collected.

Example 4

Microarray Detection Protocol a) Sample Preparation

30 µL of 4× Hybridization Buffer (3.638 M NaCl, 200 mM Na-phosphate, pH 7.5, 1 nM corner marker oligo, 4 mM TROLOX, 0.1% TWEEN-20) was added to 90 µL of assay sample (product of step e of the Example 2 or step f of Example 3).

b) Microarray Slides

A ProPlate Slide Module (CSW Gasket, FLC adhesive; Grace Bio-Labs, #204841) was assembled with a microarray slide containing 14 (7×2) arrays spaced 9 mm apart. Each array consisted of three replicas of 96 amine modified oligo-nucleotides complementary to the random region of the aptamers. The oligonucleotides were spotted with a contact printer in house on proprietary 3'×1' polymer slides.

c) Microarray Blocking

100 µL of Blocking Buffer (Blocker Casein in PBS, Pierce #37528, 1 mM TROLOX) was added to the wells of the ProPlate Slide Module and incubated at 65° C. for 15-30 minutes. The Blocking Buffer was removed.

d) Hybridization and Washing

110 µL of assay sample was added to the microarray, and a 3×1×0.125 inch aluminum block was placed on top of the ProPlate Slide Module. The assembly was wrapped in aluminum foil and incubated at 65° C. for 16 hours without mixing in a humidity chamber. The Al-foil and Al-block were removed along with the assay sample, and the microarray was rinsed once with 200 µL of Wash Buffer 1 (50 mM Na-phosphate, pH 7.5, 0.1% TWEEN-20), preheated to 65° C. Wash Buffer 1 was removed and the ProPlate Slide Module was disassembled. The microarray slide was placed in a pap jar containing 25 mL Wash Buffer 1 (preheated to 65° C.) and incubated at 65° C. for 15 minutes with mixing. The microarray slide was transferred to a second pap jar containing 25 mL Wash Buffer 2 (50 mM Na-phosphate, pH 7.5, preheated to 65° C.) and incubated at 65° C. for 5 minutes with mixing. The microarray slide was transferred to a third pap jar containing 25 mL Wash Buffer 2 and incubated at 65° C. for 5 minutes with mixing. The microarray slide was removed from Wash Buffer 2 and immediately dried in a stream of dry nitrogen.

e) Detection.

The microarray slide was scanned with a TECAN LS300 Reloaded Fluorescence Laser Scanner, and fluorescence signal was quantified on each feature using the software package ArrayVision (8.0 Rev 3.0, Imaging Research, Inc.). The fluorescence signal was quantified using density as principal measure, with segmentation and variable spot shape. The xml export file was imported into a database for further data analysis.

f) Quantitative PCR Detection Protocol

Primer Design

Amplification primers for each aptamer were chosen using PrimerQuest (Integrated DNA Technologies) with default parameter settings except primer Tm min=60° C., optimum=65° C., and max=70° C., and product size range=50-100 bp. Candidate primers were than analyzed for internal hairpin, homo-dimer, and hetero-dimer 3' end complementarity, with OligoAnalyzer 3.0 (Integrated DNA Technologies) with default parameter settings except oligo conc.=0.2 μM. Candidates were rejected if 3' end complementarity ΔG≤−3.5 kcal/mol.

Quantitative PCR Reaction

5 μL of neutralized assay sample (see step 5 of the Affinity Assay Protocol (Example 2) or step 6 of the Photo-Crosslink Assay Protocol (Example 3)) was diluted 20× with 95 μL dH2O. 20 μL amplification reactions were prepared with 5 μL of diluted assay sample and 1×KOD Buffer (Novagen #), 0.2 mM each dATP, dCTP, dGTP, and dTTP, 1×SYBR Green I (Invitrogen #), 0.2 μM each 5' and 3' primer, and 0.025 U/μL KOD XL DNA Polymerase (Novagen #). Samples were prepared in a bio hood with contaminant-free reagents. One pair of primers was used in each reaction for quantification of one aptamer. Samples with known quantities of aptamer were also prepared for generating standard curves. Samples were amplified in a Bio-Rad iCyler by incubating at 95° C. for 2 minutes, cycling 40 times at 95° C. for 15 seconds followed by 72° C. for 60 seconds.

Data Analysis

For each aptamer, threshold cycle (Ct) values were determined for each sample from the amplification plots, and used to generate a standard curve for each aptamer with the data analysis software supplied with the Bio-Rad iCycler. The number of copies of each aptamer in each assay sample was determined using the standard curve, and converted to aptamer concentration after adjusting for dilution factor and sample volume. The concentration of aptamer in each assay sample was plotted as a function of input protein concentration.

Example 5

Figure 11:
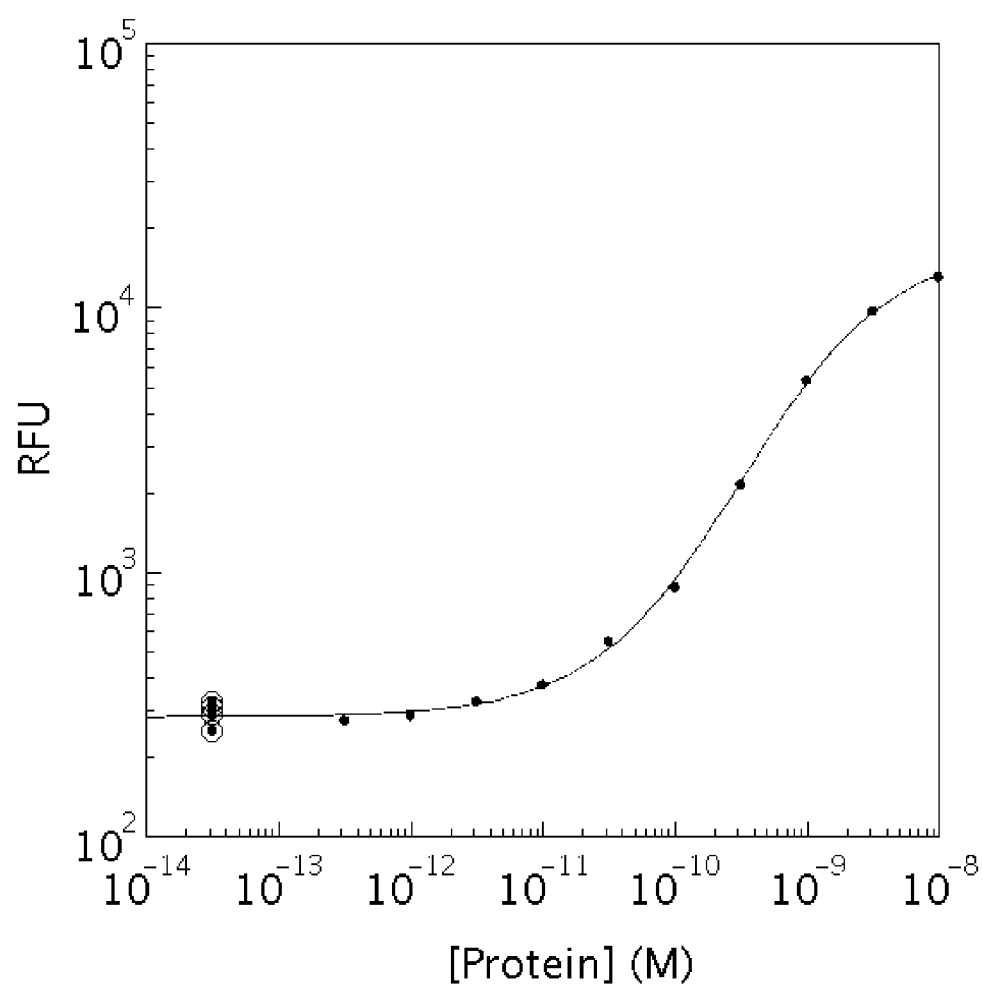
FIG. 11 illustrates the dose response curve (RFU versus log input target protein concentration) for the detection of the target protein Angiogenin in buffer using the Photo-Crosslink Assay Protocol with MicroArray Detection. The solid line represents a sigmoidal fit through the data points. Four replicate no-protein data points are circled.

Protein Detection in Buffer Using Photo-Crosslink Assay Protocol and Array Detection A ten point dilution series in buffer was created for thirteen protein analytes (angiogenin, BLC, C3a, Coagulation Factor V, Coagulation Factor XI, CTACK, Endostatin, FGF7, IGFBP-3, Prekallikrein, PSA-ACT, TIMP-1, and tPA) starting with a 10 nM concentration of each analyte and serially diluting to 330 fM with half-log dilutions (dilution factor of 3.1623). Four no-protein controls were included to give a total of fourteen samples. The Cy3-aptamer mixture contained the thirteen aptamers to the target proteins in the dilution series, along with fourteen control aptamers whose target proteins were absent. Samples were processed using the Photo-Crosslink Assay Protocol (Example 3) and quantified with Microarray Detection as described in Example 4. The results are set forth in FIG. 11 which shows a relative fluorescence units (RFU) versus concentration plot for the target protein Angiogenin in buffer.

Example 6

Protein Detection in Buffer using Affinity Assay Protocol and Q-PCR

Figure 12:
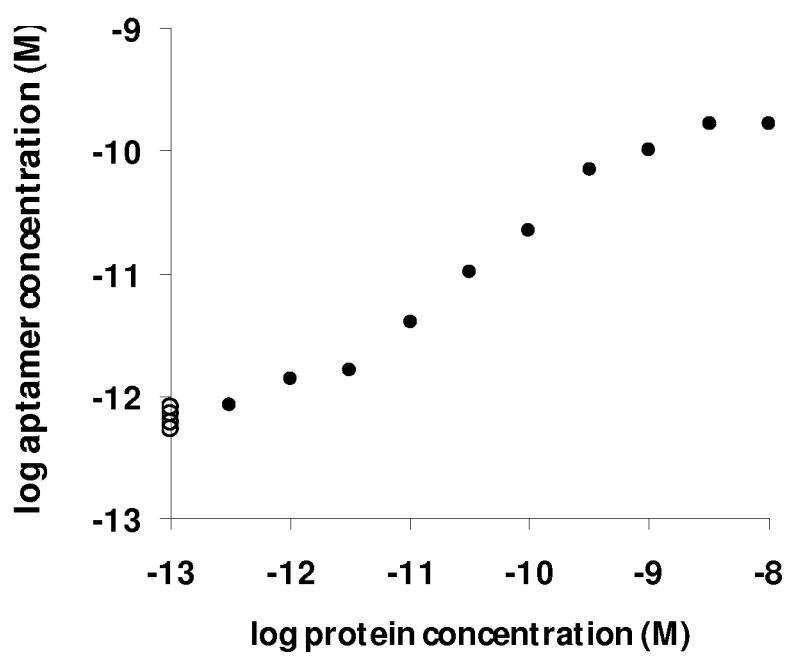
FIG. 12 illustrates the dose response curve (detected aptamer concentration versus input target protein concentration) for detection of Angiogenin in buffer using the Affinity Assay Protocol with Q-PCR Detection. Four replicate no-protein measurements are indicated on the y-axis as open circles.

A ten point dilution series in buffer was created for twelve protein analytes (angiogenin, C1q, C5b, 6 Complex, CMP-SAS, EG-VEGF, IP-10, PAI-1, PDGF-BB, Prothrombin, E-selectin, tPA, and vWF) starting with a 10 nM concentration of each analyte and serially diluting to 330 fM with half-log dilutions (dilution factor of 3.1623). Four no-protein controls were included to give a total of fourteen samples. The Cy3-aptamer mixture contained the twelve aptamers to the target proteins in the dilution series. Samples were processed using the Affinity Assay Protocol (Example 2) and quantified by Q-PCR (Example 4). Primers 2175-47-F3 (5'-GAGTGT-GTGACGAGTGTGGAG-3') (SEQ ID NO:1) and 2175-47-R3 (5'-TCGGTTGTGGTGACGCCCG-3') (SEQ ID NO:2) were used for quantification of the angiogenin aptamer 2175-47 in the assay samples. The results are set forth in FIG. 12 which shows a log plot of the concentration of aptamer detected versus the concentration of input protein for angiogenin.

Example 7

Protein Measurements in Test Samples are Enabled by Aptamers with Slow Off-Rates Preparation of Aptamer/Primer Mixtures and Test Samples Aptamers with a biotin Cy3 detection label (4 nM each) are mixed with a 3× excess of capture probe (oligonucleotide complementary to the 3' fixed region of the aptamer containing a biotin tag and photocleavable element) in 1×SB 17T. and heated at 95° C. for 4 minutes then 37° C. for 13 minutes, and diluted 1:4 in 1×SB17T. 55 uL of aptamer/primer mix is added to a microtiter plate (Hybaid # AB-0407) and sealed with foil. Test samples are prepared in a microtiter plate by mixing known concentrations of protein analytes in SB 17T and diluting serially with SB17T.

Sample Equilibration 55 uL of aptamer/primer mix is added to 55 uL of test sample and incubated at 37° C. for 15 minutes in a foil-sealed microtiter plate. The final concentration of each aptamer in the equilibration mixture is 0.5 nM. After equilibration, all subsequent steps of this method are performed at room temperature unless otherwise noted.

Aptamer Capture and Free Protein Removal

A DuraPore filtration plate (Millipore HV cat# MAHVN4550) is washed once with 100 uL 1×SB17T by vacuum filtration, add 133.3 uL 7.5% Streptavidin-agarose resin (Pierce) is added to each well and washed twice with 200 uL 1×SB17T. 100 uL of equilibrated samples is transferred to the Durapore plate containing the Streptavidin-agarose resin and incubated on a thermomixer (Eppendorf) at 800 rpm for 5 minutes. The resin is washed once with 200 uL 1×SB17T+100 uM biotin and once with 200 uL 1×SB17T.

Protein Tagging with Biotin 100 uL of 1.2 mM NHS-PEO4-biotin in SB17T, prepared immediately before use, is added to the resin with captured aptamer and aptamer:protein complexes and incubated on a thermomixer at 800 rpm for 20 minutes. The resin is washed five times with 200 uL 1×SB17T by vacuum filtration.

Slow-Off Rate Enrichment Process & Photocleavage

The drip director is removed from underside of the DuraPore plate and the plate is placed over a 1 mL microtiter collection plate. The resin is washed once with 200 uL 1×SB17T by centrifugation at 1000×g for 30 sec. 80 uL of 1×SB17T+10 mM dextran sulfate is added to the resin and irradiated with a BlackRay Mercury Lamp on a thermomixer at 800 rpm for 10 minutes. The DuraPore plate is transferred to a new 1 mL deepwell plate and centrifuged at 1000×g for 30 seconds to collect the photocleaved aptamer and protein:aptamer complexes.

Protein Capture and Free Aptamer Removal 50 uL of MyOne-streptavidin C1 paramagnetic beads (Invitrogen) (10 mg/mL in 1×SB 17T) is added to a microtiter plate. The beads are separate with a magnet for 60 seconds and the supernatant is removed. 225 uL of photocleavage mixture is added to the beads and mixed for 5 minutes. The beads are washed four times with 200 uL 1×SB 17T by separating the magnetic beads and replacing the wash buffer. The final wash buffer is removed.

Aptamer Elution 100 uL Sodium Phosphate Elution Buffer (10 mM $Na_2HPO_4$, pH 11) is added to the beads and mixed for 5 minutes. 90 uL of eluate is transferred to a microtiter plate and neutralized with 10 uL Sodium Phosphate Neutralization Buffer (10 mM $NaH_2PO_4$, pH 5).

Aptamer Hybridization to Microarrays

DNA arrays are prepared with oligonucleotide capture probes comprised of the complementary sequence of the variable region of each aptamer immobilized on a custom microscope slide support. Multiple arrays (subarrays) exist on each slide, and subarrays are physically separated by affixing a gasket (Grace) for sample application. Arrays are pretreated with 100 uL Blocking Buffer and incubated for 15 minutes at 65° C. on a thermomixer. 30 uL of Hybridization Buffer is added to 90 uL of neutralized aptamer eluate in a microtiter plate, incubated at 95° C. for 5 minutes in a Thermal Cycler, and cooled to 65° C. at 0.1° C./second. Blocking Buffer is removed from the arrays and 110 uL of aptamer sample is added to the arrays and incubate in a humid chamber at 65° C. for 20 hours.

Array Washing

Aptamer sample is removed from the arrays and the arrays are washed once with 200 uL of sodium phosphate Tween-20 wash buffer at 65° C., with the gasket in place, and three times with 25 mL sodium phosphate, Tween-20 wash buffer at 65° C. in a pap jar with the gasket removed. Arrays are dried with a nitrogen gun.

Quantitate Signal on Arrays

Array slides are scanned on a TECAN LS300 Reloaded.in an appropriate channel for Cy3 detection and Cy3 signal on each array feature is quantified.

Figure 13A:
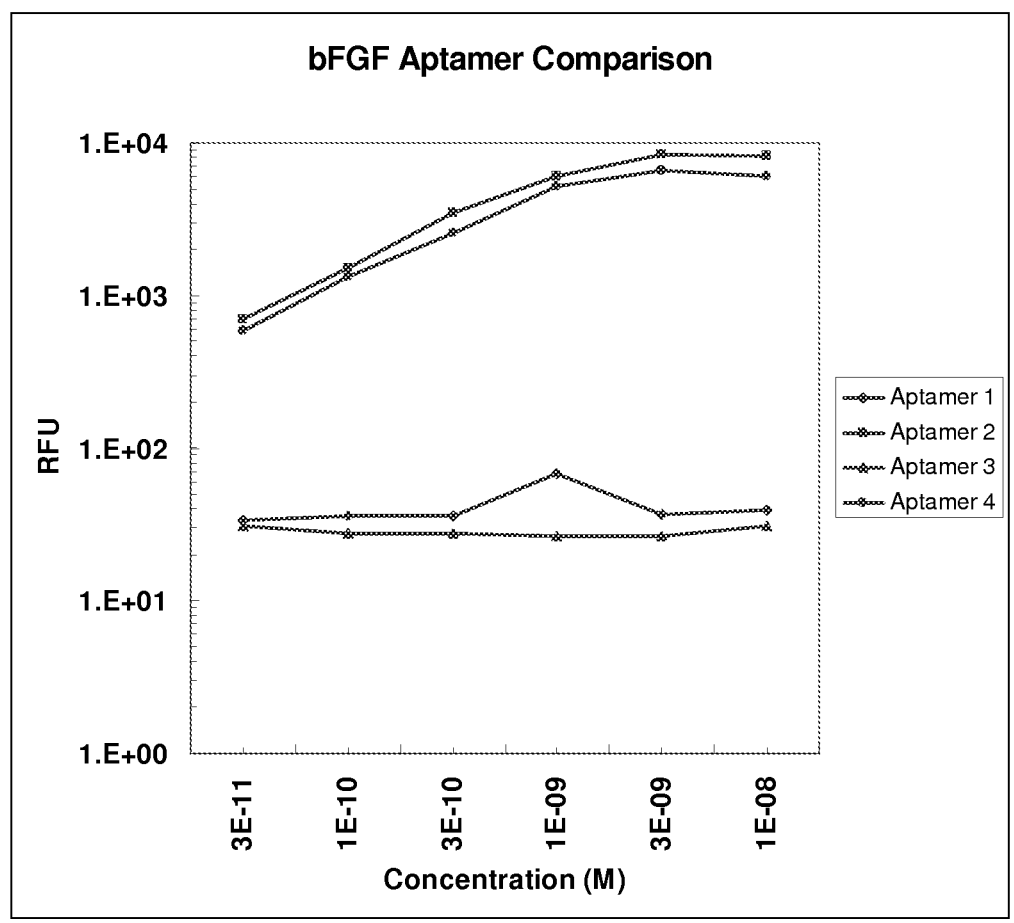
FIGS. 13A to 13C illustrate dose response curves for slow off-rate aptamers versus traditional aptamers for three different targets.
Figure 13B:
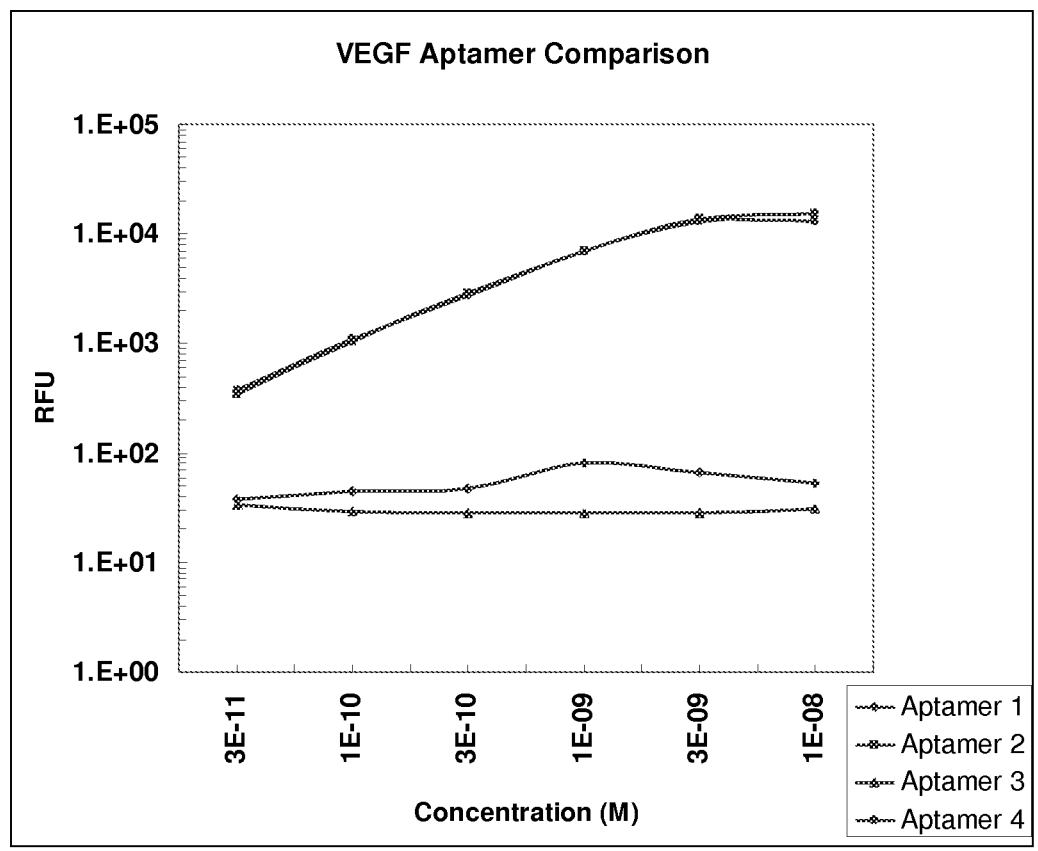
Figure 13C:
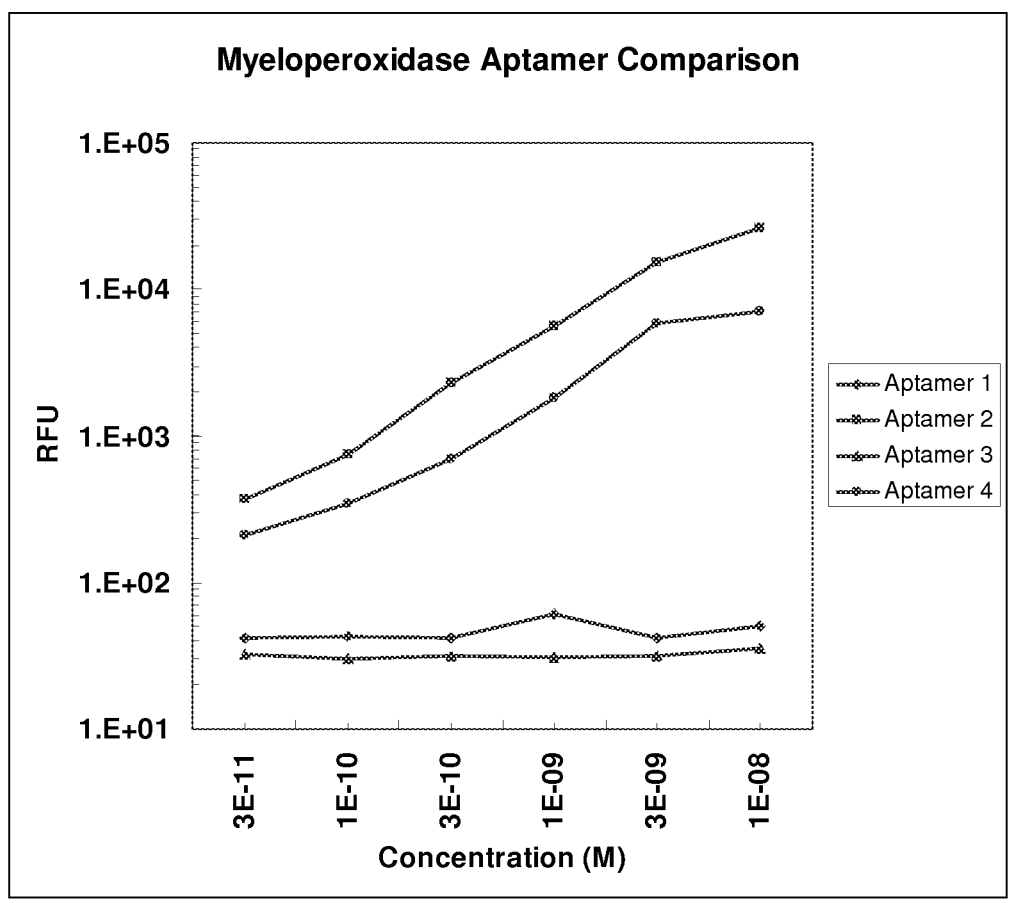

Results:

Apatmers specific to three different targets (bFGF, VEGF, and Myeloperoxidase) were produced using traditional SELEX methods and materials. A second set of aptamers specific to the same set of targets were made using 5-position modified nucleotides and selected for very slow off-rates for their respective targets. Aptamers made in the traditional process had measured off rates on the order of less than 5 minutes. Aptamers made with the modified nucleotides and using slow off-rate enrichment process during selection had off rates of greater than 20 minutes. Two sets of aptamers were made for each target by the two different methods for a total of 4 different aptamer populations for each target. The ability of these aptamer populations to measure analyte concentrations in test samples was evaluated as described above over a range of target concentrations. Relative signal from the DNA chip detection was plotted against the input target concentration. See FIG. 13A to 13C. The response curve of the traditional aptamers is very flat and the sensitivity of the detection is fairly low. The sensitivity of detection of the respective targets with the slow off-rate aptamers is excellent. The data supports the need to use the slow-off aptamers for maximum analytic performance.

Example 8

Reproducibility Using Slow Off Rate Aptamers

Figure 14:
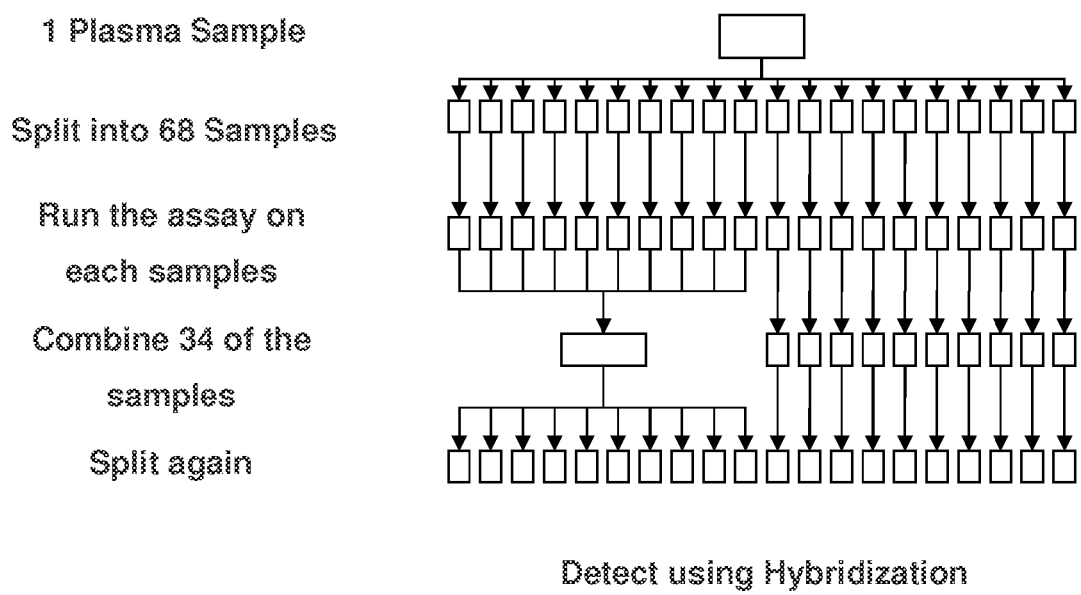
FIG. 14 illustrates the sample layout for an assay reproducibility study.
Figure 15:
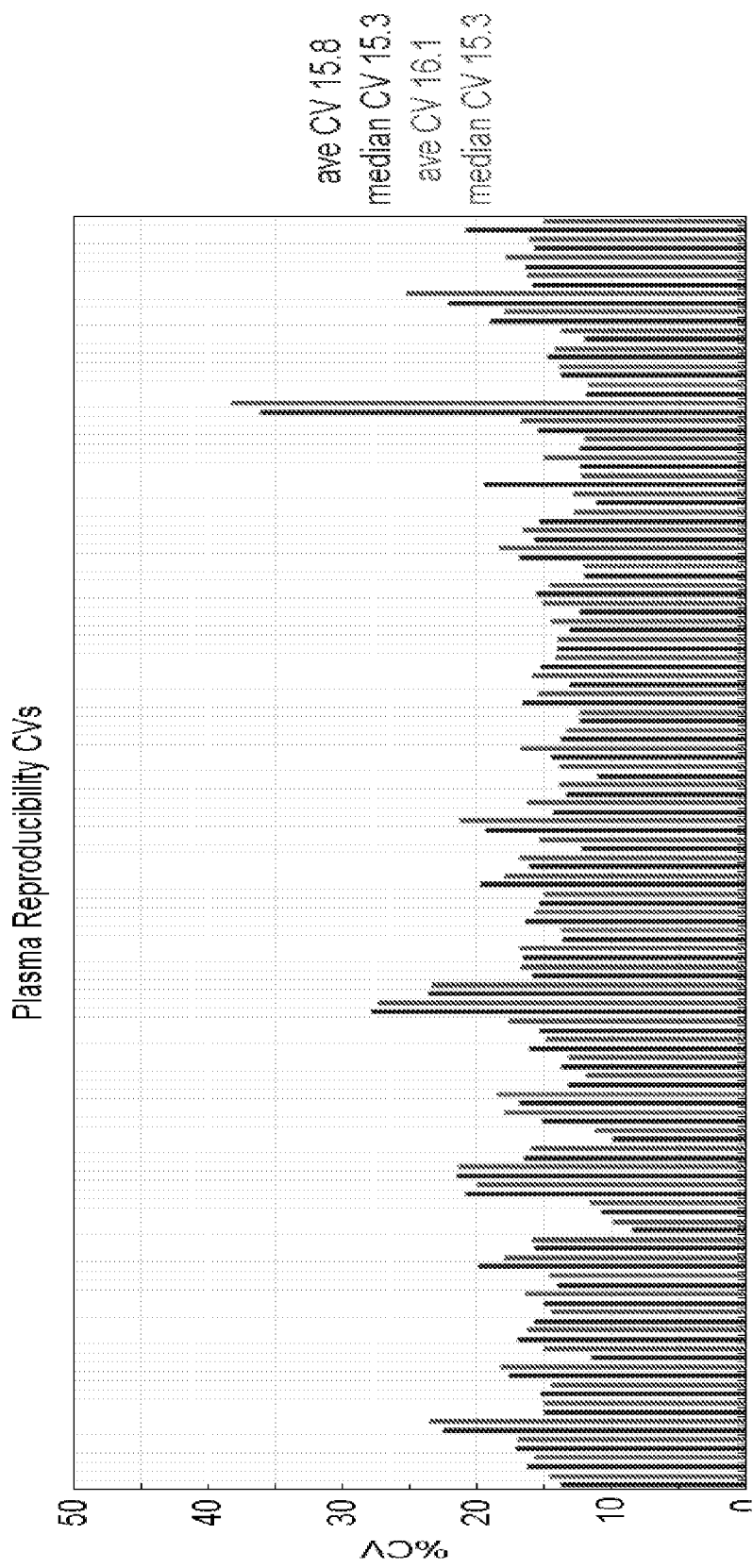
FIG. 15 illustrates the CV's of the pooled and unpooled sample study.

Using the method of Example 7, one plasma sample was split into 68 different aliquots. The assay of Example 7 was performed on each of the 68 samples. 34 of the samples were combined and split again. The remaining 34 samples were simply retested. In this manner the reproducibility of the assay can be tested for within and between assay consistency. The sample layout and detection scheme is shown in FIG. 14. FIG. 15 shows the % CV in the measurement of all the samples indicated in FIG. 14. The unpooled and pooled samples have the same CV's.

Example 9

One Catch Affinity Binding Method a) Equilibration of Aptamers with Plasma, Serum, or Whole Blood 30 uL of a Cy3-aptamer mixture (20 nM each aptamer) is combined with 30 uL of an $(AB)_2$-$T_8$-PC-primer mixture (60 nM for each primer) in SB17T and incubated at 95° C. for 4 minutes and at 37° C. for 13 minutes. 55 uL of the complex biological protein mixture (plasma, serum, or whole blood), diluted 1:1000 in SB17T, is combined with 55 uL of the aptamer/primer mixture and incubated at 37° C. for 15 minutes to achieve binding equilibrium. All following steps are performed at room temperature unless otherwise noted.

b) Protein Tagging 100 uL of aptamer:protein mixture is combined with 10 uL of SB17T containing 500 uM NHS-PEO4-biotin (Pierce #21329) and incubated for 20 minutes at 37° C. Excess NHS reagent is quenched by adding 10 uL of 200 mM TRIS buffer (pH 7.5) to the reaction mixture and incubating for 10 minutes at 37° C.

c) Protein Capture and Free Aptamer Removal 100 uL of streptavidin resin (DynaBeads MyOne Streptavidin C1, Invitrogen #650-03, 10 mg/mL in SB 17T) is added to a Durapore membrane to capture aptamer/protein complexes. 100 uL of the aptamer/protein mixture is added to the resin, mixed for 15 minutes, and vacuum filtered to remove free aptamer. The resin is washed three times with 200 uL SB 17T by vacuum filtration, and once with 200 uL SB 17T by centrifugation.

d) Complexed Aptamer Release

The resin is resuspended in 90 uL Elution Buffer (2 mM NaOH, 0.1% TWEEN-20) and mixed for 5 minutes to release aptamer from the aptamer/protein complex. The resin is removed by centrifugation, and the eluate containing released aptamer is collected. 80 uL eluate is neutralized and buffered with 20 uL Neutralization Buffer (8 mM HCl, 0.5 mM Tris-HCl (pH 7.5), 0.1% TWEEN-20). Aptamer is detected as described in Example 4.

A number of patents, patent application publications, and scientific publications are cited throughout and/or listed at the end of the description. Each of these is incorporated herein by reference in their entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

The words "comprise", "comprises", and "comprising" are to be interpreted inclusively rather than exclusively.

What is claimed is:

1. A method for detecting for the presence of a target molecule in a test sample, the method comprising:
   (a) preparing a mixture by contacting the test sample with an aptamer comprising a first tag and having specific affinity for the target molecule, wherein an aptamer affinity complex is formed if the target molecule is present in the test sample;
   (b) exposing the mixture to a first solid support comprising a first capture element, and allowing the first tag to associate with the first capture element;
   (c) removing components of the mixture not associated with the first solid support;
   (d) releasing the aptamer affinity complex from the first solid support;
   (e) attaching a second tag to the target molecule of the aptamer affinity complex;
   (f) exposing the released aptamer affinity complex to a second solid support comprising a second capture element and allowing the second tag to associate with the second capture element;
   (g) removing uncomplexed aptamer from the mixture by partitioning the uncomplexed aptamer from the aptamer affinity complex;
   (h) detecting for the presence of the target molecule by detecting the aptamer portion of the aptamer affinity complex; and
   wherein, the method is capable of detecting for the presence of the target molecule in the test sample when the target molecule is present at a sub-picomolar level.

2. The method of claim 1, wherein the aptamer comprises at least one modified nucleotide.

3. The method of claim 2, wherein the at least one modified nucleotide is a C-5 modified pyrimidine.

4. The method of claim 3, wherein the C-5 modified pyrimidine is selected from the group listed in FIG. 16.

5. The method of claim 3, wherein the aptamer further comprises at least one chemical modification at one or more positions independently selected from the group consisting of a 2'-position sugar modification, a 2'-amino (2'—NH$_2$), a 2'-fluoro (2'-F), a 2'-O-methyl (2'-OMe), a 5-position pyrimidine modification, an 8-position purine modification, a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap.

6. The method of claim 1, wherein (h) further comprises dissociating the aptamer from said aptamer affinity complex before detecting the aptamer.

7. The method of claim 1, wherein the rate of dissociation of the aptamer affinity complex ($t_{1/2}$) is selected from the group consisting of ≥30 minutes, ≥60 minutes, ≥90 minutes, ≥120 minutes, ≥150 minutes, ≥180 minutes, ≥210 minutes, and ≥240 minutes.

8. The method of claim 1, wherein the aptamer is detected and optionally quantified using a method selected from the group consisting of Q-PCR, MS, and hybridization.

9. The method of claim 1 further comprising adding a detectable moiety to the aptamer.

10. The method of claim 9, wherein the detectable moiety is selected from the group consisting of a dye, a quantum dot, a radiolabel, a electrochemical functional group, an enzyme, and an enzyme substrate.

11. The method of claim 1, wherein the aptamer comprises DNA, RNA or both DNA and RNA.

12. The method of claim 1, wherein the target molecule is selected from the group consisting of a protein, a peptide, a carbohydrate, a polysaccharide, a glycoprotein, a hormone, a receptor, an antigen, an antibody, a virus, a substrate, a metabolite, a transition state analog, a cofactor, an inhibitor, a drug, a dye, a nutrient, a growth factor, a tissue, and a controlled substance.

13. The method of claim 1, wherein the test sample is selected from the group consisting of a biological sample, an environmental sample, a chemical sample, a pharmaceutical sample, a food sample, an agricultural sample, and a veterinary sample.

14. The method of claim 13, wherein the biological sample is selected from the group consisting of whole blood, leukocytes, peripheral blood mononuclear cells, plasma, serum, sputum, breath, urine, semen, saliva, meningial fluid, amniotic fluid, glandular fluid, lymph fluid, nipple aspirate, bronchial aspirate, synovial fluid, joint aspirate, cells, a cellular extract, stool, tissue, a tissue extract, a tissue biopsy, and cerebrospinal fluid.

15. The method of claim 1, wherein the first tag and the second tag each comprise at least one component independently selected from the group consisting of a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, avidin, streptavidin, Extravidin, neutravidin, a metal, histidine, and any portion of any of these structures.

16. The method of claim 1, wherein the first capture element and said second capture element each comprises at least one component independently selected from a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, avidin, streptavidin, Extravidin, neutravidin, a metal, histidine, and any portion of any of these structures.

17. The method of claim 1, wherein the first tag comprises a releasable moiety.

18. The method of claim 1, wherein the first solid support and the second solid support each is independently selected from the group consisting of a polymer bead, an agarose bead, a polystyrene bead, an acrylamide bead, a solid core bead, a porous bead, a paramagnetic bead, glass bead, controlled pore bead, a microtitre well, a cyclo-olefin copolymer substrate, a membrane, a plastic substrate, nylon, a Langmuir-Blodgett film, glass, a germanium substrate, a silicon substrate, a silicon wafer chip, a flow through chip, a microbead, a polytetrafluoroethylene substrate, a polystyrene substrate, a gallium arsenide substrate, a gold substrate, and a silver substrate.

19. The method of claim 1, wherein the method has a limit of detection (LOD) selected from the group consisting of 630 fM, 530 fM and 90 fM.

20. The method of claim 1, wherein the method is capable of detecting the target molecule FGF7 in a test sample with an LOD of 90 fM.

* * * * *